United States Patent
Amit et al.

(10) Patent No.: US 12,060,575 B2
(45) Date of Patent: *Aug. 13, 2024

(54) METHODS OF EXPANDING EMBRYONIC STEM CELLS IN A SUSPENSION CULTURE

(71) Applicant: Technion Research & Development Foundation Limited, Haifa (IL)

(72) Inventors: Michal Amit, Yuvalim (IL); Joseph Itskovitz-Eldor, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 683 days.

This patent is subject to a terminal disclaimer.

(21) Appl. No.: 17/178,279

(22) Filed: Feb. 18, 2021

(65) Prior Publication Data
US 2021/0189331 A1 Jun. 24, 2021

Related U.S. Application Data

(60) Division of application No. 15/814,432, filed on Nov. 16, 2017, now Pat. No. 10,968,427, which is a division of application No. 14/720,853, filed on May 25, 2015, now Pat. No. 9,834,749, which is a continuation of application No. 12/309,817, filed as application No. PCT/IL2007/000970 on Aug. 2, 2007, now Pat. No. 9,040,297.

(60) Provisional application No. 60/840,692, filed on Aug. 29, 2006, provisional application No. 60/834,795, filed on Aug. 2, 2006.

(51) Int. Cl.
C12N 5/0735 (2010.01)
C12N 5/00 (2006.01)

(52) U.S. Cl.
CPC ......... *C12N 5/0606* (2013.01); *C12N 5/0031* (2013.01); *C12N 5/0037* (2013.01); *C12N 5/0043* (2013.01); *C12N 2501/115* (2013.01); *C12N 2501/15* (2013.01); *C12N 2501/2306* (2013.01); *C12N 2501/235* (2013.01); *C12N 2533/12* (2013.01); *C12N 2533/90* (2013.01)

(58) Field of Classification Search
None
See application file for complete search history.

(56) References Cited

U.S. PATENT DOCUMENTS

| | | | |
|---|---|---|---|
| 5,418,159 A | 5/1995 | Gough et al. | |
| 6,107,543 A | 8/2000 | Sims et al. | |
| 6,245,566 B1 | 6/2001 | Gearhart et al. | |
| 6,576,464 B2 | 6/2003 | Gold et al. | |
| 7,250,294 B2 | 1/2007 | Carpenter et al. | |
| 7,413,902 B2 | 8/2008 | Bodnar et al. | |
| 7,413,904 B2 | 8/2008 | Gold et al. | |
| 7,432,104 B2 | 10/2008 | Mitalipova et al. | |
| 7,452,718 B2 | 11/2008 | Gold et al. | |
| 7,455,983 B2 | 11/2008 | Xu et al. | |
| 7,473,555 B2 | 1/2009 | Mandalam et al. | |
| 7,504,257 B2 | 3/2009 | Reubinoff et al. | |
| 7,560,281 B2 | 7/2009 | Carpenter et al. | |
| 7,638,328 B2 | 12/2009 | Eriksson et al. | |
| 7,641,897 B2 | 1/2010 | Weissman et al. | |
| 7,824,670 B2 | 11/2010 | Haggiag et al. | |
| 7,851,167 B2 | 12/2010 | Xu | |
| 7,892,835 B2 | 2/2011 | Akaike et al. | |
| 7,897,389 B2 | 3/2011 | Gold et al. | |
| 7,951,591 B2 | 5/2011 | Robl et al. | |
| 8,067,233 B2 | 11/2011 | Totey et al. | |
| 8,252,585 B2 | 8/2012 | Carpenter | |
| 8,252,586 B2 | 8/2012 | Carpenter et al. | |
| 8,318,486 B2 | 11/2012 | Amit et al. | |
| 8,563,311 B2 | 10/2013 | Amit et al. | |
| 8,597,947 B2 | 12/2013 | Reubinoff | |
| 8,637,311 B2 | 1/2014 | Mandalam et al. | |
| 8,697,444 B2 | 4/2014 | Schoonjans | |
| 8,722,405 B2 | 5/2014 | Tryggvason et al. | |
| 9,040,297 B2 | 5/2015 | Amit et al. | |
| 9,404,079 B2 | 8/2016 | Amit et al. | |
| 9,834,749 B2 | 12/2017 | Amit et al. | |
| 10,385,312 B2 | 8/2019 | Amit et al. | |
| 10,968,427 B2 | 4/2021 | Amit et al. | |
| 2002/0127715 A1 | 9/2002 | Benvenisty et al. | |
| 2002/0168763 A1 | 11/2002 | Yan et al. | |
| 2003/0064503 A1 | 4/2003 | Abujadayel | |

(Continued)

FOREIGN PATENT DOCUMENTS

| AU | 2000072431 | 5/2001 |
|---|---|---|
| AU | 2001011128 | 7/2001 |

(Continued)

OTHER PUBLICATIONS

John et al. Analysis and Isolation of Embryonic Mammalian Neurons by Fluorescence-Activated Cell Sorting. The Journal of Neuroscience (1986) 6(5) 1492-1512 (Year: 1986).*
Embryonic Period (Weeks 3-8). University of Michigan Medical School. accessed at (https://www.med.umich.edu/lrc/coursepages/m1/embryology/embryo/05embryonicperiod.htm on Nov. 7, 2023) (Year: 2000).*

(Continued)

*Primary Examiner* — Arthur S Leonard
*Assistant Examiner* — Briana N Ebbinghaus

(57) ABSTRACT

A method of expanding and maintaining human embryonic stem cells (ESCs) in an undifferentiated state by culturing the ESCs in a suspension culture under culturing conditions devoid of substrate adherence is provided. Also provided are a method of deriving ESC lines in the suspension culture and methods of generating lineage-specific cells from ESCs which were expanded in the suspension culture of the present invention.

19 Claims, 25 Drawing Sheets
(24 of 25 Drawing Sheet(s) Filed in Color)
Specification includes a Sequence Listing.

(56) References Cited

U.S. PATENT DOCUMENTS

| | | |
|---|---|---|
| 2003/0119107 A1 | 6/2003 | Dang et al. |
| 2003/0153082 A1 | 8/2003 | Bhatia |
| 2003/0166272 A1 | 9/2003 | Abujadayel |
| 2003/0211603 A1 | 11/2003 | Earp et al. |
| 2003/0224411 A1 | 12/2003 | Stanton et al. |
| 2004/0009593 A1 | 1/2004 | Keirstead et al. |
| 2004/0014211 A1 | 1/2004 | Ogle et al. |
| 2004/0077985 A1 | 4/2004 | Rudd |
| 2004/0110286 A1 | 6/2004 | Bhatia |
| 2004/0137612 A1 | 7/2004 | Baksh et al. |
| 2004/0180347 A1 | 9/2004 | Stanton et al. |
| 2004/0191901 A1 | 9/2004 | Assady et al. |
| 2004/0229350 A1 | 11/2004 | Strelchenko et al. |
| 2005/0032207 A1 | 2/2005 | Wobus et al. |
| 2005/0054093 A1 | 3/2005 | Haas |
| 2005/0095703 A1 | 5/2005 | Semb et al. |
| 2005/0095708 A1 | 5/2005 | Pera et al. |
| 2005/0101014 A1 | 5/2005 | Keirstead et al. |
| 2005/0118713 A1 | 6/2005 | Strelchenko et al. |
| 2005/0153444 A1 | 7/2005 | Mandalam et al. |
| 2005/0153445 A1 | 7/2005 | Mandalam et al. |
| 2005/0164383 A1 | 7/2005 | Reubinoff et al. |
| 2005/0210537 A1 | 9/2005 | Dominko et al. |
| 2005/0214938 A1 | 9/2005 | Gold et al. |
| 2005/0220761 A1 | 10/2005 | Haggiag et al. |
| 2005/0227352 A1 | 10/2005 | Xie |
| 2005/0227353 A1 | 10/2005 | Mummery |
| 2005/0260591 A1 | 11/2005 | Ward et al. |
| 2006/0030040 A1 | 2/2006 | Yang et al. |
| 2006/0057720 A1 | 3/2006 | Xu et al. |
| 2006/0063253 A1 | 3/2006 | Maciag et al. |
| 2006/0134636 A1 | 6/2006 | Stanton et al. |
| 2006/0182724 A1 | 8/2006 | Riordan |
| 2006/0223179 A1 | 10/2006 | Thomson et al. |
| 2006/0252150 A1 | 11/2006 | Cheng |
| 2006/0286544 A1 | 12/2006 | Mandal et al. |
| 2007/0053890 A1 | 3/2007 | Rosic-Kablar et al. |
| 2007/0111306 A1 | 5/2007 | Salli et al. |
| 2007/0231898 A1 | 10/2007 | Keirstead et al. |
| 2007/0248945 A1 | 10/2007 | McLaughlin et al. |
| 2007/0249044 A1 | 10/2007 | Desai et al. |
| 2007/0280989 A1 | 12/2007 | Shahar et al. |
| 2007/0298453 A1 | 12/2007 | Murdoch et al. |
| 2008/0070303 A1 | 3/2008 | West et al. |
| 2008/0076176 A1 | 3/2008 | Dominko et al. |
| 2008/0171385 A1 | 7/2008 | Bergendahl et al. |
| 2008/0182328 A1 | 7/2008 | Snyder et al. |
| 2008/0193421 A1 | 8/2008 | Kruse et al. |
| 2008/0241919 A1 | 10/2008 | Parsons et al. |
| 2008/0274125 A1 | 11/2008 | Guehenneux |
| 2008/0311607 A1 | 12/2008 | Geng et al. |
| 2009/0029461 A1 | 1/2009 | Choo et al. |
| 2009/0104695 A1 | 4/2009 | Shushan et al. |
| 2009/0136559 A1 | 5/2009 | Athanasiou et al. |
| 2009/0148876 A1 | 6/2009 | Dodge |
| 2009/0155218 A1 | 6/2009 | Hayek et al. |
| 2009/0291496 A1 | 11/2009 | Racey et al. |
| 2010/0047906 A1 | 2/2010 | Totey et al. |
| 2010/0068806 A1 | 3/2010 | Laine et al. |
| 2010/0069251 A1 | 3/2010 | Kim et al. |
| 2010/0093091 A1 | 4/2010 | Reubinoff et al. |
| 2010/0120145 A1 | 5/2010 | Brunner et al. |
| 2010/0221829 A1 | 9/2010 | Amit et al. |
| 2011/0039332 A1 | 2/2011 | Sakurada et al. |
| 2011/0300114 A1 | 12/2011 | Priller et al. |
| 2011/0311977 A1 | 12/2011 | Mandal et al. |
| 2012/0122209 A1 | 5/2012 | Reubinoff et al. |
| 2012/0148537 A1 | 6/2012 | Chan et al. |
| 2012/0282691 A1 | 11/2012 | Qian et al. |
| 2012/0322146 A1 | 12/2012 | Carpenter et al. |
| 2013/0084563 A1 | 4/2013 | Amit et al. |
| 2013/0102023 A1 | 4/2013 | Smith et al. |
| 2013/0130375 A1 | 5/2013 | Rudy-Reil |
| 2013/0252329 A1 | 9/2013 | Amit et al. |
| 2013/0316445 A1 | 11/2013 | Beardsley et al. |
| 2015/0252326 A1 | 9/2015 | Amit et al. |
| 2016/0319241 A1 | 11/2016 | Amit et al. |
| 2018/0066227 A1 | 3/2018 | Amit et al. |
| 2019/0316082 A1 | 10/2019 | Amit et al. |

FOREIGN PATENT DOCUMENTS

| | | |
|---|---|---|
| AU | 2002237681 | 6/2002 |
| AU | 2002313670 | 1/2003 |
| AU | 2004294835 | 6/2005 |
| AU | 2009213101 | 10/2009 |
| AU | 2014201623 | 5/2014 |
| CA | 2248555 | 9/1997 |
| CA | 2409698 | 11/2001 |
| CA | 2434760 | 5/2002 |
| CA | 2447015 | 11/2002 |
| CA | 2451486 | 1/2003 |
| CA | 2453068 | 1/2003 |
| CA | 2453438 | 1/2003 |
| CA | 2468335 | 6/2003 |
| CA | 2469483 | 6/2003 |
| CA | 2470539 | 6/2003 |
| CA | 2508880 | 7/2004 |
| CA | 2524611 | 11/2004 |
| CA | 2559854 | 9/2005 |
| CA | 2573437 | 2/2006 |
| CA | 2640644 | 11/2013 |
| EP | 1809739 | 7/2007 |
| EP | 2267116 | 12/2010 |
| GB | 2379447 | 3/2003 |
| GB | 2392674 | 3/2004 |
| GB | 2393733 | 4/2004 |
| GB | 2393734 | 4/2004 |
| GB | 2394723 | 5/2004 |
| GB | 2427873 | 1/2007 |
| GB | 2431165 | 4/2007 |
| HK | 1075673 | 2/2009 |
| HK | 1103106 | 7/2009 |
| HK | 1055765 | 9/2010 |
| IL | 141742 | 3/2002 |
| IL | 152741 | 6/2003 |
| IL | 159324 | 6/2004 |
| IL | 159578 | 6/2004 |
| IL | 159580 | 6/2004 |
| IL | 160403 | 7/2004 |
| IL | 177324 | 12/2006 |
| IL | 178006 | 12/2006 |
| IL | 180447 | 6/2007 |
| WO | WO 97/33995 | 9/1997 |
| WO | WO 99/01763 | 1/1999 |
| WO | WO 99/02552 | 1/1999 |
| WO | WO 99/20740 | 4/1999 |
| WO | WO 99/20741 | 4/1999 |
| WO | WO 00/070021 | 11/2000 |
| WO | WO 02/31123 | 4/2002 |
| WO | WO 02/44343 | 6/2002 |
| WO | WO 02/086104 | 10/2002 |
| WO | WO 03/000868 | 1/2003 |
| WO | WO 03/004605 | 1/2003 |
| WO | WO 03/006950 | 1/2003 |
| WO | WO 03/014359 | 2/2003 |
| WO | WO 03/020920 | 3/2003 |
| WO | WO 03/050249 | 6/2003 |
| WO | WO 03/050250 | 6/2003 |
| WO | WO 03/095628 | 11/2003 |
| WO | WO 2004/031369 | 4/2004 |
| WO | WO 2004/044158 | 5/2004 |
| WO | WO 2004/050826 | 6/2004 |
| WO | WO 2004/055155 | 7/2004 |
| WO | WO 2004/111210 | 12/2004 |
| WO | WO 2005/065354 | 7/2005 |
| WO | WO 2006/017370 | 2/2006 |
| WO | WO 2006/020889 | 2/2006 |
| WO | WO 2006/070370 | 7/2006 |
| WO | WO 2007/002086 | 1/2007 |
| WO | WO 2007/002210 | 1/2007 |
| WO | WO 2007/026353 | 3/2007 |
| WO | WO 2007/122233 | 11/2007 |
| WO | WO 2008/007082 | 1/2008 |

(56) References Cited

FOREIGN PATENT DOCUMENTS

| WO | WO 2008/015682 | 2/2008 |
|---|---|---|
| WO | WO 2008/054819 | 5/2008 |
| WO | WO 2008/148105 | 12/2008 |

OTHER PUBLICATIONS

Kassem et al. Mesenchymal Stem Cells: Cell Biology and Potential Use in Therapy. Basic & Clinical Pharmacology & Toxicology ( 2004) 95 (5). 209-214) (Year: 2004).*
Pan et al. Stem cell pluripotency and transcription factor Oct4. Cell Research (2002) 12. 321-329 (Year: 2002).*
Official Action Dated Jan. 12, 2022 from US Patent and Trademark Office Re. U.S. Appl. No. 16/454,168. (44 pages).
GenBank GenBnak Overview, Printed from Website, 2, 2022.
Zhang et al. "Enhacement of Oligodendrocyte Differentiation from Murine Embryonic Stem Cells by an Activator of gp 130 Signaling", Stem Cells, 22(3):344-354, May 2004.
Advisory Action Before the Filing of An Appeal Brief Dated Jul. 6, 2017 From the US Patent and Trademark Office Re. U.S. Appl. No. 14/720,853. (4 pages).
Advisory Action Before the Filing of An Appeal Brief Dated Jul. 9, 2012 From the US Patent and Trademark Office Re. U.S. Appl. No. 12/309,817.
Applicant-Initiated Interview Summary Dated Jan. 11, 2016 From the US Patent and Trademark Office Re. U.S. Appl. No. 13/909,128.
Communication Pursuant to Article 94(3) Dated Jan. 15, 2020 From the European Patent Office Rc. Application No. 18186556.9. (4 Pages).
Communication Pursuant to Article 94(3) EPC Dated Mar. 2, 2016 From the European Patent Office Re. Application No. 13185969.6.
Communication Pursuant to Article 94(3) EPC Dated Apr. 11, 2017 From the European Patent Office Re. Application No. 06766237.9. (5 Pages).
Communication Pursuant to Article 94(3) EPC Dated Jul. 28, 2014 From the European Patent Office Re. Application No. 07790025.6.
Communication Pursuant to Article 94(3) EPC Dated Sep. 28, 2011 From the European Patent Office Re. Application No. 07790025.6.
Communication Relating to the Results of the Partial International Search Dated Jan. 9, 2008 From the International Searching Authority Re.: Application No. PCT/IL2007/000970.
European Search Report and the European Search Opinion Dated Sep. 12, 2014 From the European Patent Office Re. Application No. 13185969.6.
European Search Report and the European Search Opinion Dated Nov. 13, 2018 From the European Patent Office Re. Application No. 18186556.9. (10 Pages).
European Search Report and the European Search Opinion Dated Apr. 18, 2018 From the European Patent Office Re. Application No. 17197313.4. (7 Pages).
Examination Report Dated Mar. 27, 2012 From the Intellectual Property Office of Singapore Issued by the Austrian Patent Office, Service and Information Center (TRF) on Feb. 20, 2012 Re. Application No. 200801730-3.
Examination Report Dated Jan. 30, 2014 From the Intellectual Property Office of Singapore Issued by the Austrian Patent Office Re. Application No. 201200039-4.
Examiner's Report Dated Aug. 29, 2011 From the Australian Government IP Australia Re. Application No. 2006286149.
Final Official Action Dated Aug. 20, 2020 from the US Patent and Trademark Office Re. U.S. Appl. No. 15/814,432. (5 pages).
International Preliminary Report on Patentability Dated Feb. 3, 2009 From the International Bureau of WIPO Re. Application No. PCT/IL2007/000970.
International Preliminary Report on Patentability Dated Apr. 9, 2009 From the International Bureau of WIPO Re. Application No. PCT/IL2006/000998.

International Search Report Dated Jun. 13, 2008 From the International Searching Authority Re. Application No. PCT/IL2007/000970.
International Searching Report and the Written Opinion Dated Jun. 4, 2008 From the International Searching Authority Re. Application No. PCT/IL2006/00998.
Notice Of Allowance Dated Jul. 28, 2017 From the US Patent and Trademark Office Re. U.S. Appl. No. 14/720,853. (9 pages).
Notice of Non-Compliant Amendment Dated Sep. 2, 2015 From the US Patent and Trademark Office Re. U.S. Appl. No. 13/909,128.
Official Action Dated Sep. 5, 2018 From the US Patent and Trademark Office Re. U.S. Appl. No. 15/209,776. (19 pages).
Official Action Dated Apr. 6, 2020 From the US Patent and Trademark Office Re. U.S. Appl. No. 15/814,432. (14 Pages).
Official Action Dated Dec. 6, 2012 From the US Patent and Trademark Office Re. U.S. Appl. No. 12/309,817.
Official Action Dated May 9, 2013 From the US Patent and Trademark Office Re. U.S. Appl. No. 12/309,817.
Official Action Dated Aug. 11, 2011 From the US Patent and Trademark Office Re. U.S. Appl. No. 11/991,077.
Official Action Dated Mar. 13, 2012 From the US PAtent and Trademark Office Re. U.S. Appl. No. 11/991,077.
Official Action Dated Feb. 14, 2014 From the US Patent and Trademark Office Re. U.S. Appl. No. 12/309,817.
Official Action Dated Oct. 15, 2015 From the US Patent and Trademark Office Re. U.S. Appl. No. 13/909,128.
Official Action Dated Apr. 17, 2017 from the US Patent and Trademark Office Re. U.S. Appl. No. 14/720,853. (7 pages).
Official Action Dated Oct. 18, 2011 From the US Patent and Trademark Office Re. U.S. Appl. No. 12/309,817.
Official Action Dated Mar. 22, 2018 From the US Patent and Trademark Office Re. U.S. Appl. No. 15/209,776. (97 pages).
Official Action Dated Oct. 24, 2012 From the US PAtent and Trademark Office Re. U.S. Appl. No. 11/991,077.
Official Action Dated May 25, 2011 From the US PAtent and Trademark Office Re. U.S. Appl. No. 11/991,077.
Official Action Dated Aug. 26, 2016 From the US Patent and Trademark Office Re. U.S. Appl. No. 14/720,853.
Official Action Dated Mar. 26, 2012 From the US Patent and Trademark Office Re. U.S. Appl. No. 12/309,817.
Official Action Dated Sep. 26, 2019 From the US Patent and Trademark Office Re. U.S. Appl. No. 15/814,432. (33 pages).
Partial European Search Report Dated Mar. 20, 2014 From the European Patent Office Re. Application No. 13185969.6.
Patent Examination Report Dated Jan. 15, 2014 From the Australian Government, IP Australia Re. Application No. 2012262726.
Patent Examination Report Dated Aug. 22, 2014 From the Australian Government, IP Australia Re. Application No. 2012262726.
Patent Examination Report Dated Nov. 25, 2016 From the Australian Government, IP Australia Re. Application No. 2015203310. (4 Pages).
Search Report and Written Opinion Dated Apr. 3, 2013 From the Intellectual Property Office of Singapore Issued by the Austrian Patent Office on Mar. 1, 2013 Re. Application No. 201200039-4.
Search Report and Written Opinion Dated Jan. 26, 2010 Received From the Intellectual Property Office of Singapore on Aug. 16, 2010 Issued by the Austrian Patent Office, Service and Information Center (TRF) Re. Application No. 200801730-3.
Second Supplementary European Search Report and the European Search Opinion Dated Apr. 20, 2011 From the European Patent Office Re. Application No. 06766237.9.
Second Written Opinion Dated Aug. 5, 2011 From the Austrian Patent Office on Behalf of the Intellectual Property Office of Singapore Re. Application No. 200801730-3.
Supplementary European Search Report and the European Search Opinion Dated Jul. 23, 2010 From the European Patent Office Re. Application No. 06766237.9.
Written Opinion Dated Jun. 13, 2008 From the International Searching Authority Rc. Application No. PCT/IL2007/000970.
Amit et al. "Clonally Derived Human Embryonic Stem Cell Lines Maintain Pluripotency and Proliferative Potential for Prolonged Periods of Culture", Developmental Biology, 227: 271-278, 2000.

(56) References Cited

OTHER PUBLICATIONS

Amit et al. "Dynamic Suspension Culture for Scalable Expansion of Undifferentiated Human Pluripotent Stem Cells", Nature Protocols, XP008146753, 6(5): 572-579, May 1, 2011.

Amit et al. "Feeder Layer- and Serum-Free Culture of Human Embryonic Stem Cells", Biology of Reproduction, XP002466324, 70(3): 837-845, Jan. 1, 2004. Abstract, p. 837-838, ES Cell Culture.

Amit et al. "Feeder-Free Culture of Human Embryonic Stem Cells", Methods in Enzymology, XP009105807, 420(3): 37-49, Jan. 1, 2006.

Amit et al. "Human Feeder Layers for Human Embryonic Stem Cells", Biology of Reproduction, 68: 2150-2156, 2003.

Amit et al. "Suspension Culture of Undifferentiated Human Embryonic and Induced Pluripotent Stem Cells", Stem Cell Reviews and Reports, 6(2): 248-259, Apr. 30, 2010.

Cheng et al. "Human Adult Marrow Cells Support Prolonged Expansion of Human Embryonic Stem Cells in Culture", Stem Cells, 21: 131-142, 2003.

Cowan et al. "Derivation of Embryonic Stem-Cell Lines From Human Blastocysts", The New England Journal of Medicine, 350(13): 1353-1356, 2004.

Daheron et al. "LIF/STAT3 Signaling Fails to Maintain Self-Renewal of Human Embryonic Stem Cells", Stem Cells, 22: 770-778, 2004.

Hovatta et al. "A Culture System Using Human Foreskin Fibroblasts as Feeder Cells Allows Production of Human Embryonic Stem Cells".

Humphrey et al. "Maintenance of Pluripotency in Human Embryonic Stem Cells is STAT3 Independent", Stem Cells, XP002463152, 22(4): 522-530, Jan. 1, 2004.

Klimanskaya et al. "Human Embryonic Stem Cells Derived Without Feeder Cells", The Lancet, 365: 1636-1641, Mar. 7, 2005. p. 1636, Methods.

Kollet et al. "The Soluble Interleukin-6 (IL-6) Receptor/IL-6 Fusion Protein Enhances In Vitro Maintenance and Proliferation of Human CD34+CD38-/Low Cells Capable of Repopulating Severe Combined Immunodeficiency Mice", Blood, 94(3): 923-931, Aug. 1, 1999.

Levenstein et al. "Basic FGF Support of Human Embryonic Stem Cell Self-Renewal", Stem Cells, 24(3): 568-574, Mar. 2006.

Ludwig et al. "Derivation of a Human Embryonic Stem Cells in Defined Conditions", Nature Biotechnology, 24(2): 185-187, Feb. 2006.

Mallon et al. "Toward Xeno-Free Culture of Human Embryonic Stem Cells", International Journal of Biochemistry and Cell Biology, 38: 1063-1075, Jan. 23, 2006.

Nichols et al. "Derivation of Germline Competent Embryonic Stem Cells With a Combination of Interleukin-6 and Soluble Interleukin-6 Receptor", Experimental Cell Research, 215(1): 237-239, Nov. 1994.

Niwa et al. "Self-Renewal of Pluripotent Embryonic Stem Cells is Mediated Via Activation of STAT3", Genes & Development, 12: 2048-2060, 1998.

Ueda et al. "Establishment of Rat Embryonic Stem Cells and Making of Chimera Rats", PLoS one 3(7):2 e2800, 1-9, Jul. 2008.

Van der Jeught et al. "Application of Small Molecules Favoring Naive Pluripotency During Human Embryonic Stem Cell Derivation", Cellular Reprogramming, XP055224755, 17(3): 170-180, Jun. 1, 2015.

Xu et al. "Basic Fibroblast Growth Factor Supports Undifferentiated Human Embryonic Stem Cell Growth Without Conditioned Medium", Stem Cells, 23: 315-323, 2005. Abstract, p. 316, hES Culture.

Xu et al. "Feeder-Free Growth of Undifferentiated Human Embryonic Stem Cells", Nature Biotechnology, XP002672078, 19(10): 971-974, Oct. 2001.

Yamanishi et al. "Roles of Transforming Growth Factor Beta in Inhibition of Androgen-Induced Growth of Shionogi Carcinoma Cells in Serum-Free Medium", Cancer Research, 50: 6179-6183, Oct. 1, 1990.

Yoshida et al. "Maintenance of the Pluripotential Phenotype of Embryonic Stem Cells Through Direct Activation of GP130 Signalling Pathways", Mechanisms of Development, 45: 163-171, 1994.

Zur Nieden et al. "Embryonic Stem Cells Remain Highly Pluripotent Following Long Term Expansion as Aggregates in Suspension Bioreactors", Journal of Biotechnology, 129: 421-432, 2007.

* cited by examiner

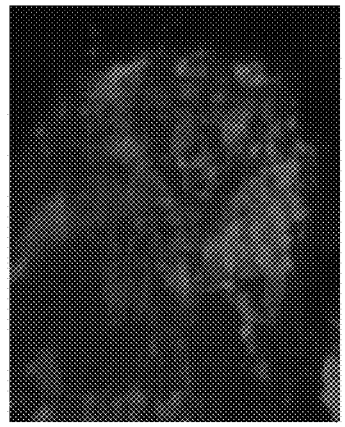
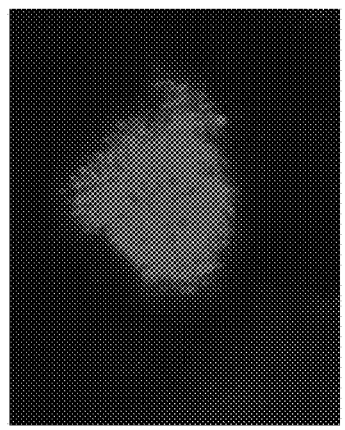
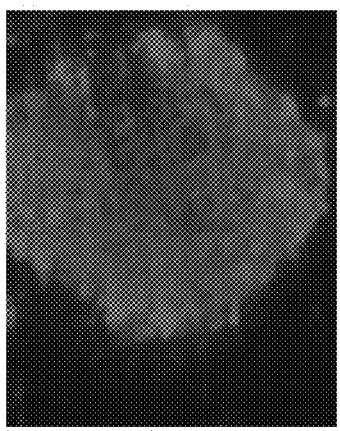
Fig. 2c
Fig. 2b
Fig. 2a

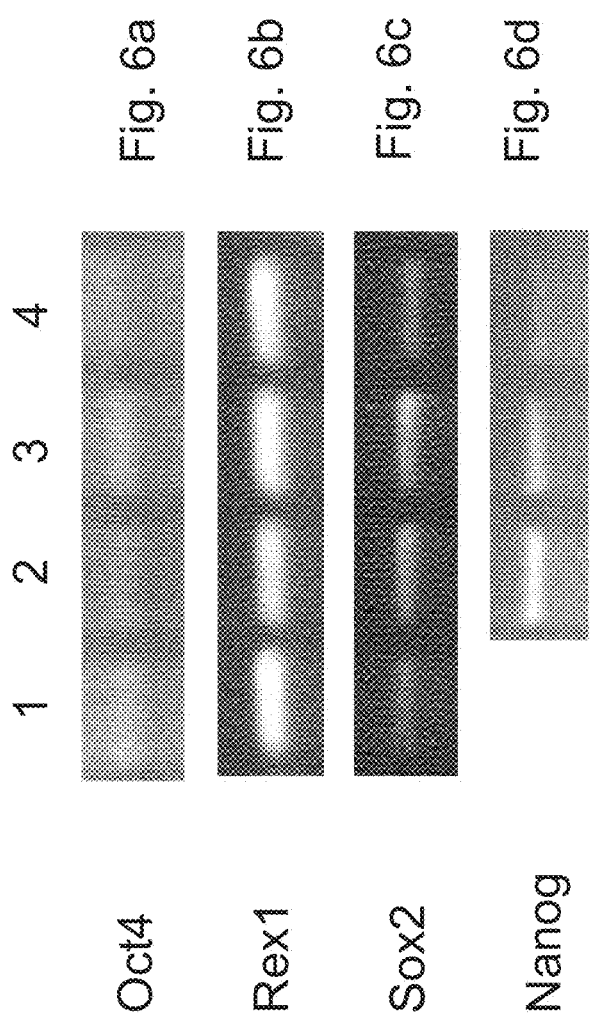

Fig. 8a
Fig. 8b
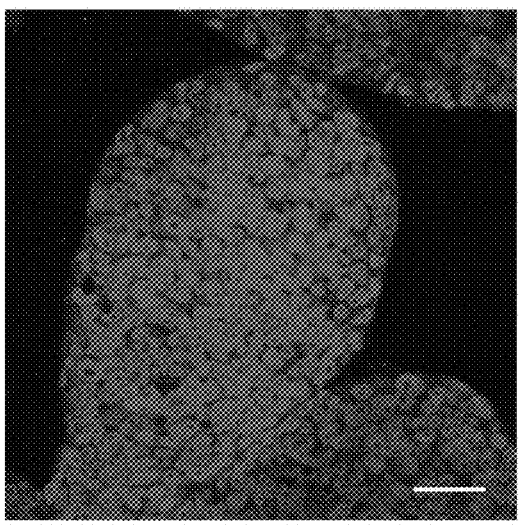
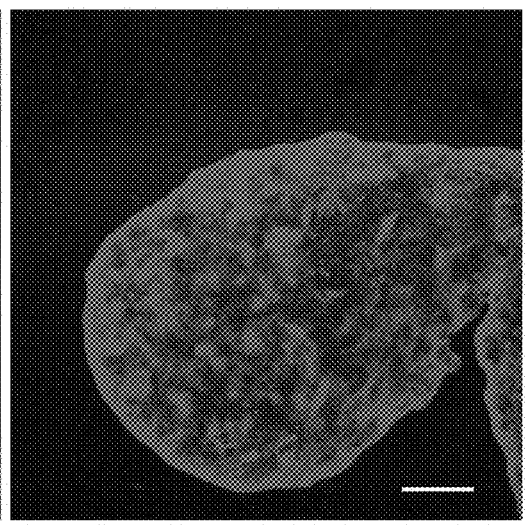
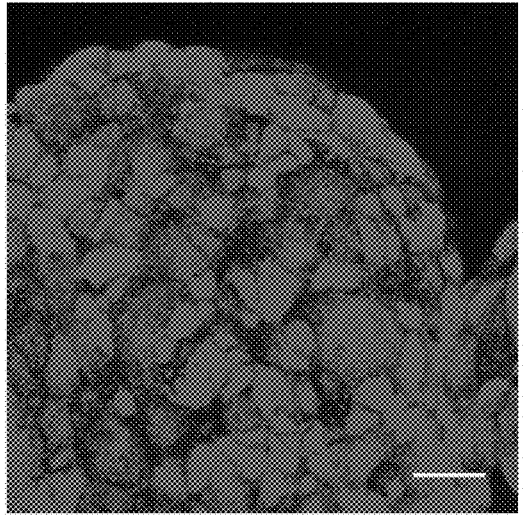
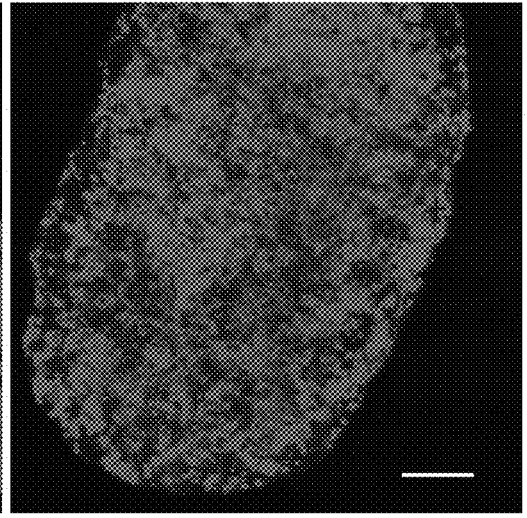
Fig. 8c
Fig. 8d

Fig. 12a
Fig. 12b
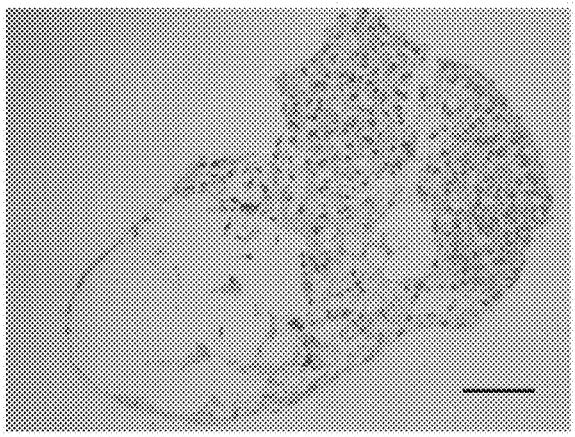
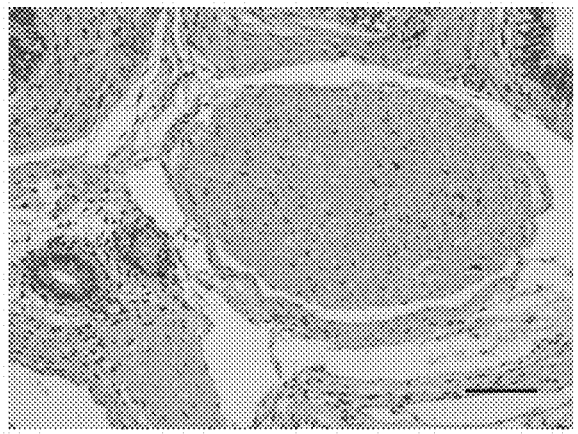
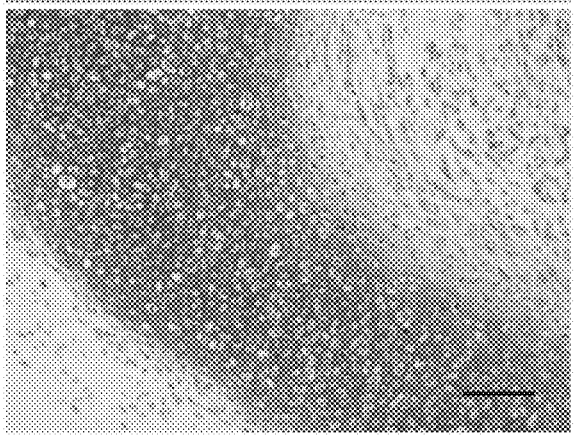
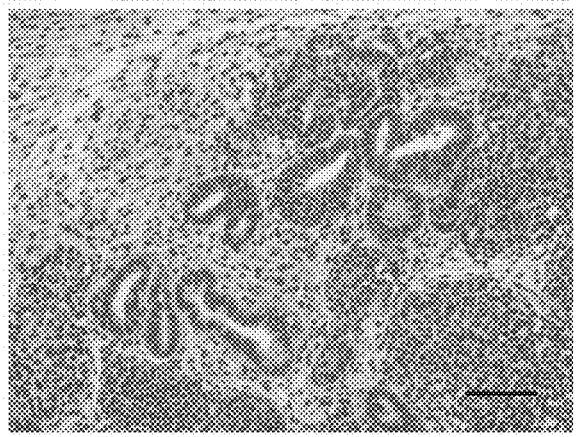
Fig. 12c
Fig. 12d

Fig. 13a
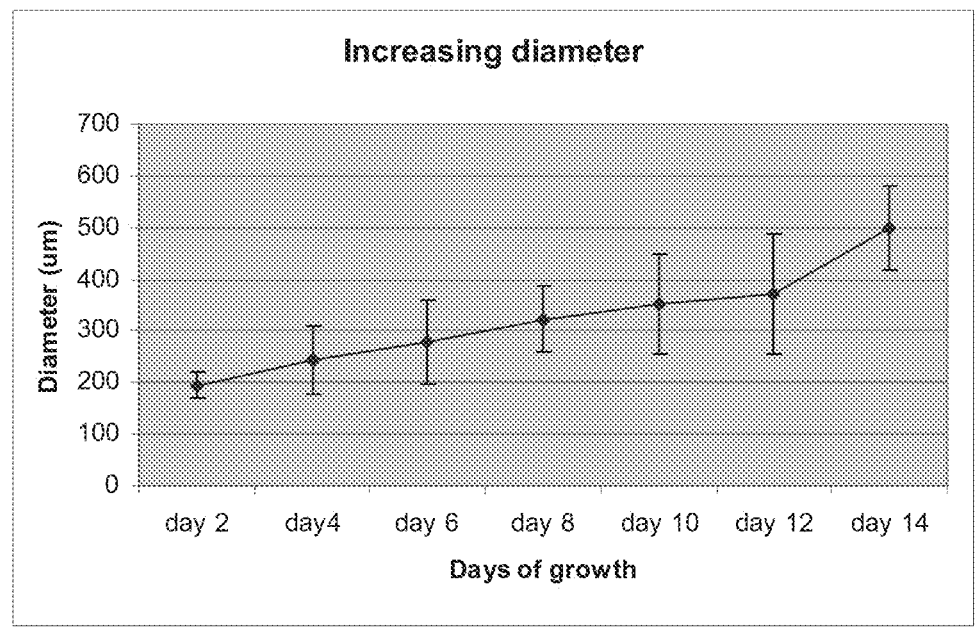
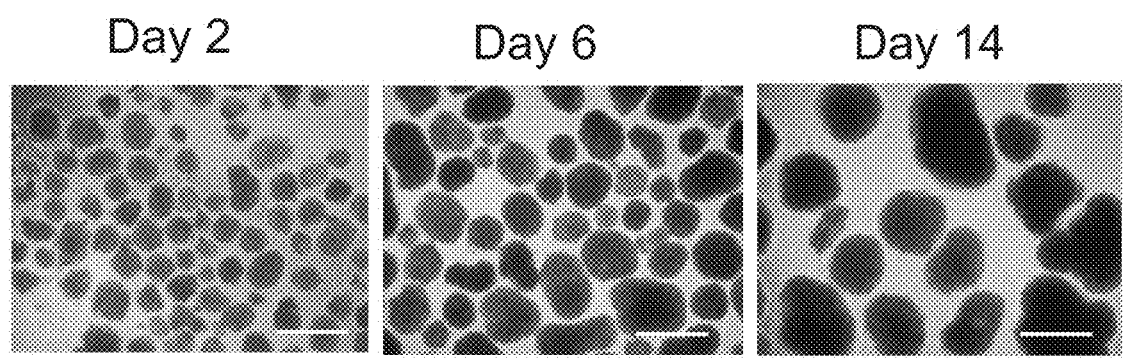
Day 2     Day 6     Day 14
Fig. 13b     Fig. 13c     Fig. 13d

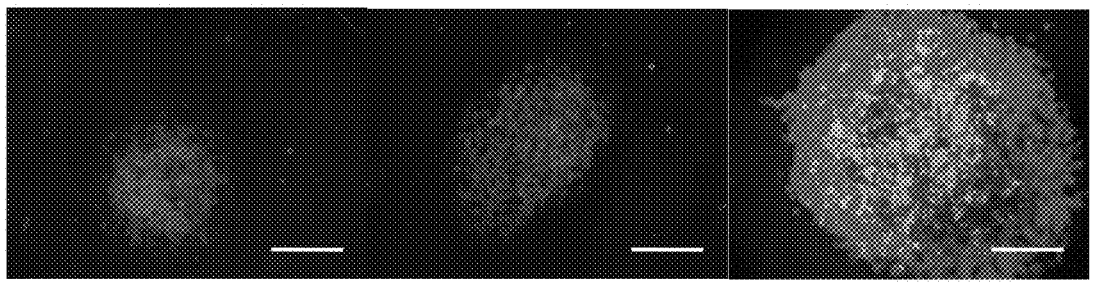

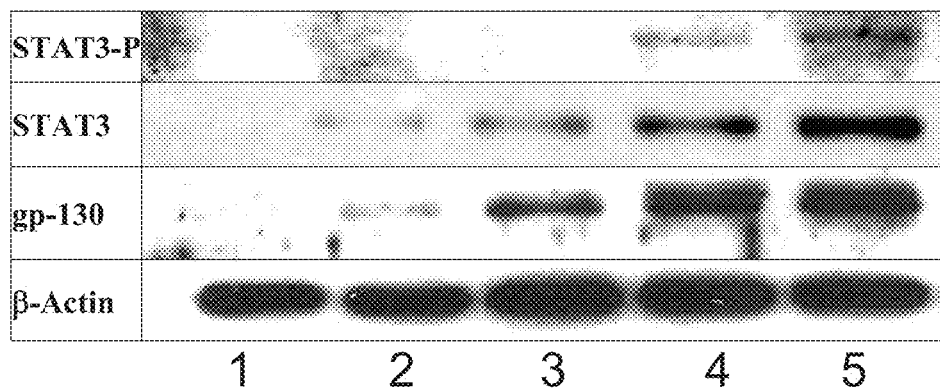
Fig. 15a
Fig. 15b
Fig. 15c
Fig. 15d
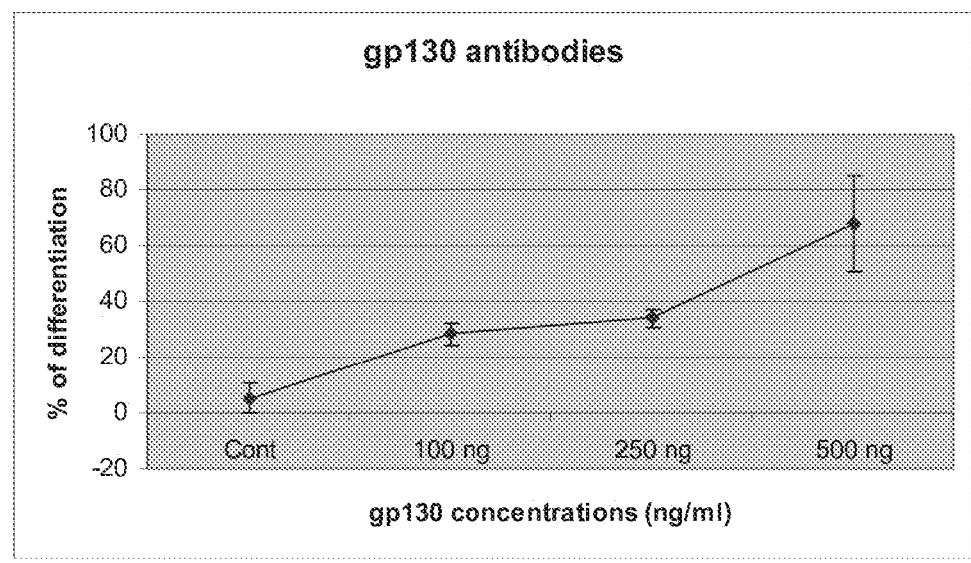
Fig. 16
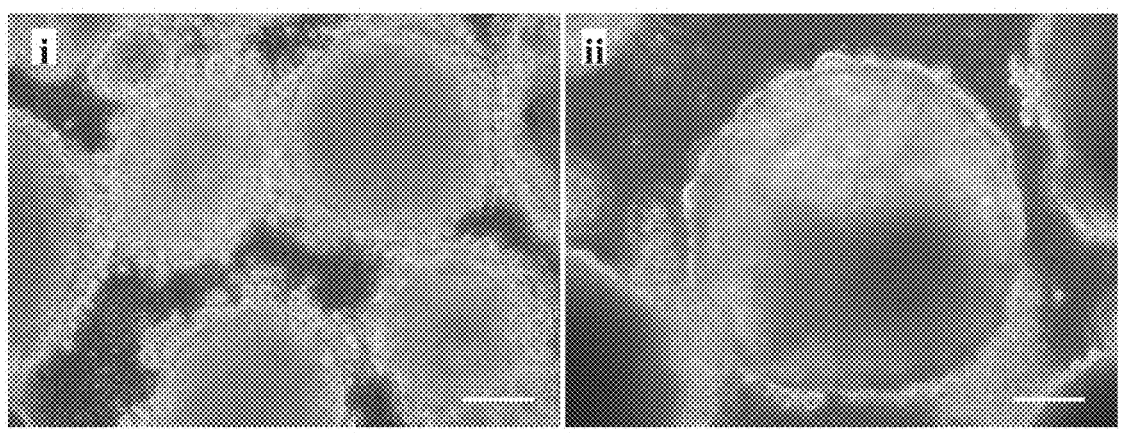
Fig. 17a   Fig. 17b

METHODS OF EXPANDING EMBRYONIC STEM CELLS IN A SUSPENSION CULTURE

RELATED APPLICATIONS

This application is a division of U.S. patent application Ser. No. 15/814,432 filed on Nov. 16, 2017, which is a is a division of U.S. patent application Ser. No. 14/720,853 filed on May 25, 2015, now U.S. Pat. No. 9,834,749 which is a continuation of U.S. patent application Ser. No. 12/309,817 filed on Aug. 14, 2009, now U.S. Pat. No. 9,040,297, which is a National Phase of PCT Patent Application No. PCT/IL2007/000970 having International Filing Date of Aug. 2, 2007, which claims the benefit of U.S. Provisional Patent Application Nos. 60/840,692 filed on Aug. 29, 2006 and 60/834,795 filed on Aug. 2, 2006. The contents of the above applications are all incorporated by reference as if fully set forth herein in their entirety.

SEQUENCE LISTING STATEMENT

The ASCII file, entitled 86470SequenceListing.txt, created on Feb. 18, 2021 comprising 16,521 bytes, submitted concurrently with the filing of this application is incorporated herein by reference.

FIELD AND BACKGROUND OF THE INVENTION

The present invention relates to a method of expanding and maintaining embryonic stem cells (ESCs) in an undifferentiated state in a suspension culture, and more particularly, to methods of using such ESCs for the generation of lineage-specific cells which can be used for cell-based therapy.

Human embryonic stem cells (hESCs) are proliferative, undifferentiated stem cells capable of differentiating into cells of all three embryonic germ layers. As such, hESCs hold promise for various applications including cell-based therapy, pharmaceutical screening, identification of drug targets and cell-based compound delivery which require almost indefinite amounts of proliferating, yet pluripotent hESCs.

To facilitate the exploitation of hESCs in both cell-based therapy and use in the pharmaceutical industry for drug screening, identification of drug targets and cell-based compound delivery, hESCs cultures should be scaled-up and optimized. However, culturing of hESCs on any of the currently available 2-dimensional (2-D) culturing systems (i.e., feeder layers or feeder-free matrices) limits the expansion capacity of the cells. On the other hand, when ESCs are removed from their feeder layers or feeder-free matrices and transferred to common suspension cultures, the cells loose their undifferentiated state and rapidly differentiate (Thomson et al., 1998). Thus, culturing of hESCs in suspension in Petri dishes usually results in the formation of aggregates containing differentiating cells termed embryoid bodies (EBs) [Itskovitz-Eldor et al, 2000].

To overcome such limitations, Fok and Zandstra (Fok E Y, and Zandstra P W, Stem Cells. 2005, 23: 1333-42) developed stirred-suspension cultures in which the ESCs are attached to glass microcarriers. However, although ESCs cultured under such conditions exhibited typical ESC expression patterns and retained the developmental potential of the starting cell population, the technical difficulties associated with adherence and dissociation of the ESCs from the microcarrier surface limit the robustness potential of such a culturing method. Another study by Gerecht-Nir and Itskovitz-Eldor (disclosed in PCT/IL03/01017) describes a dynamic culturing system for differentiating embryoid bodies or expanding ESCs under non-differentiation conditions. In this system, ESCs are seeded in a bioreactor designed to exert random gravity forces. However, PCT/IL03/01017 does not teach non-dynamic suspension culture systems. Another study by Cormier J. et al. (Tissue engineering 12: 3233-3245, 2006) describes culturing for 6 days of mouse embryonic stem cells (mESCs) in a suspension culture in the presence of leukemia inhibitory factor (LIF) and bovine serum under constant agitation. In a later publication (Zur Nieden N I, et al., 2007; J. of Biotechnology 129: 421-432) the authors reported that mESCs cultured in suspension under static conditions and using trypsin for passaging every 2 days exhibited a sharp decrease in the expression of undifferentiated markers such as Oct-4 and failed to maintain pluripotency as detected by the expression of early ectodermal and endodermal differentiation markers. In addition, the doubling time of the mESCs that were cultured in the dynamic or static suspension cultures was only 15 hours (Zur Nieden., et al., Supra), which may lead to chromosomal instability and abnormality (Cowan C A., et al., 2004, N. Engl. J. Med. 350: 1353-1356). In addition, in contrast to mESCs, it is known that LIF cannot maintain human ESCs in an undifferentiated state (Thomson et al, 1998; Reubinof et al, 2000). Thus, to date, continuous culturing of undifferentiated human ESCs in suspension under conditions devoid of substrate adherence (e.g., a carrier) was never demonstrated.

There is thus a widely recognized need for, and it would be highly advantageous to have, a method of obtaining a scalable culture of hESCs devoid of the above limitations.

SUMMARY OF THE INVENTION

According to one aspect of the present invention there is provided a method of expanding and maintaining human embryonic stem cells in an undifferentiated state, the method comprising culturing the embryonic stem cells in a suspension culture under culturing conditions devoid of substrate adherence and which allow expansion of the embryonic stem cells in the undifferentiated state, thereby expanding and maintaining the embryonic stem cells in the undifferentiated state.

According to another aspect of the present invention there is provided a method of deriving an embryonic stem cell line, the method comprising: (a) obtaining an embryonic stem cell from a pre-implantation stage blastocyst, post-implantation stage blastocyst and/or a genital tissue of a fetus; and (b) culturing the embryonic stem cell in a suspension culture, under culturing conditions which allow expansion of the embryonic stem cells in an undifferentiated state; thereby deriving the embryonic stem cell line.

According to yet another aspect of the present invention there is provided a method of generating lineage-specific cells from human embryonic stem cells, the method comprising: (a) culturing the human embryonic stem cells in a suspension culture under culturing conditions which allow expansion of the human embryonic stem cells in an undifferentiated state to thereby obtain expanded, undifferentiated human embryonic stem cells; and (b) subjecting the expanded, undifferentiated human embryonic stem cells to culturing conditions suitable for differentiating and/or expanding lineage specific cells; thereby generating the lineage-specific cells from the human embryonic stem cells.

According to still another aspect of the present invention there is provided a method of generating embryoid bodies from human embryonic stem cells, the method comprising: (a) culturing the human embryonic stem cells in a suspension culture under culturing conditions which allow expansion of the human embryonic stem cells in an undifferentiated state to thereby obtain expanded, undifferentiated human embryonic stem cells; and (b) subjecting the expanded, undifferentiated human embryonic stem cells to culturing conditions suitable for differentiating the human embryonic stem cells to embryoid bodies; thereby generating the embryoid bodies from the human embryonic stem cells.

According to an additional aspect of the present invention there is provided a method of generating lineage-specific cells from human embryonic stem cells, the method comprising: (a) culturing the human embryonic stem cells in a suspension culture under culturing conditions which allow expansion of the human embryonic stem cells in an undifferentiated state to thereby obtain expanded, undifferentiated human embryonic stem cells; (b) subjecting the expanded, undifferentiated human embryonic stem cells to culturing conditions suitable for differentiating the expanded, undifferentiated human embryonic stem cells to embryoid bodies; and (c) subjecting cells of the embryoid bodies to culturing conditions suitable for differentiating and/or expanding lineage specific cells; thereby generating the lineage-specific cells from the human embryonic stem cells.

According to yet an additional aspect of the present invention there is provided a culture medium comprising a soluble interleukin-6 receptor (sIL6R) and soluble interleukin-6 (IL6), wherein the sIL6R is present at a concentration of at least 10 nanogram per milliliter (ng/ml).

According to still an additional aspect of the present invention there is provided a culture medium comprising at least 2000 units per milliliter (u/ml) leukemia inhibitor factor (LIF).

According to a further aspect of the present invention there is provided a cell culture comprising cells and the culture medium of the present invention.

According to yet a further aspect of the present invention there is provided a cell culture comprising human embryonic stem cells and a culture medium which comprises at least 1000 u/ml of leukemia inhibitor factor (LIF).

According to further features in preferred embodiments of the invention described below, the culture medium is capable of maintaining the human embryonic stem cells in an undifferentiated state.

According to still further features in the described preferred embodiments the cells are embryonic stem cells.

According to still further features in the described preferred embodiments the embryonic stem cell is a human embryonic stem cell.

According to still further features in the described preferred embodiments the embryonic stem cell is a primate embryonic stem cell.

According to still further features in the described preferred embodiments the culture medium is capable of maintaining the embryonic stem cells in an undifferentiated state.

According to still further features in the described preferred embodiments, the expansion comprises obtaining at least $9 \times 10^{15}$ cells from a single embryonic stem cell following 3 months.

According to still further features in the described preferred embodiments culturing is effected under conditions devoid of substrate adherence.

According to still further features in the described preferred embodiments the suspension culture is serum-free, serum replacement-free, xeno-free, feeder-free and protein carrier-free.

According to still further features in the described preferred embodiments the medium comprises a TGFβ isoform.

According to still further features in the described preferred embodiments a medium of the suspension culture comprises an IL6RIL6 chimera.

According to still further features in the described preferred embodiments culturing is effected under xeno-free conditions.

According to still further features in the described preferred embodiments the TGFβ isoform is a TGFβ isoform 1 (TGFβ$_1$).

According to still further features in the described preferred embodiments the TGFβ isoform is a TGFβ isoform 3 (TGFβ$_3$).

According to still further features in the described preferred embodiments the TGFβ$_1$ is present at a concentration of at least 0.06 ng/ml.

According to still further features in the described preferred embodiments the TGFβ$_1$ is present at a concentration of 0.12 ng/ml.

According to still further features in the described preferred embodiments the TGFβ$_3$ is present at a concentration of at least 0.5 ng/ml.

According to still further features in the described preferred embodiments the TGFβ$_3$ is present at a concentration of 2 ng/ml.

According to still further features in the described preferred embodiments the medium further comprises basic fibroblast growth factor (bFGF).

According to still further features in the described preferred embodiments the bFGF is present at a concentration of at least 2 ng/ml.

According to still further features in the described preferred embodiments the bFGF is present at a concentration of at least 4 ng/ml.

According to still further features in the described preferred embodiments the IL6RIL6 chimera is present at a concentration of at least 25 ng/ml.

According to still further features in the described preferred embodiments the sIL6R is present at a concentration of 15-30 ng/ml.

According to still further features in the described preferred embodiments the medium comprises a soluble interleukin-6 receptor (sIL6R), wherein the sIL6R is present at a concentration of 15-30 ng/ml.

According to still further features in the described preferred embodiments the medium further comprises soluble interleukin-6 (IL6).

According to still further features in the described preferred embodiments the medium comprises leukemia inhibitor factor (LIF), wherein the LIF is present at a concentration of at least 2000 units per milliliter (u/ml).

According to still further features in the described preferred embodiments the medium comprises leukemia inhibitor factor (LIF), wherein the LIF is present at a concentration of at least 1000 units per milliliter (u/ml).

According to still further features in the described preferred embodiments the medium further comprises serum or serum replacement.

According to still further features in the described preferred embodiments the serum or serum replacement is present at a concentration of at least 10%.

According to still further features in the described preferred embodiments the method further comprising isolating lineage specific cells following step (b).

According to still further features in the described preferred embodiments isolating lineage specific cells is effected by a mechanical separation of cells, tissues and/or tissue-like structures contained within the embryoid bodies.

According to still further features in the described preferred embodiments isolating lineage specific cells is effected by subjecting the embryoid bodies to differentiation factors to thereby induce differentiation of the embryoid bodies into lineage specific differentiated cells.

According to still further features in the described preferred embodiments the protein carrier is albumin.

According to still further features in the described preferred embodiments the embryonic stem cells cultured in the suspension culture exhibit normal chromosomal karyotype following at least 2 passages.

According to still further features in the described preferred embodiments the embryonic stem cells cultured in the suspension culture exhibit normal chromosomal karyotype following at least 14 passages.

According to still further features in the described preferred embodiments the embryonic stem cells cultured in the suspension culture exhibit a doubling time of at least 20 hours.

According to still further features in the described preferred embodiments the undifferentiated state is maintained for at least 5 passages in culture.

According to still further features in the described preferred embodiments the undifferentiated state is maintained for at least 15 passages in culture.

According to still further features in the described preferred embodiments the culturing conditions are non-dynamic culturing conditions.

According to still further features in the described preferred embodiments maintaining the embryonic stem cells in an undifferentiated state is effected in a suspension culture.

The present invention successfully addresses the shortcomings of the presently known configurations by providing a method of expanding and maintaining embryonic stem cells in an undifferentiated state in a suspension culture.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

IN THE DRAWINGS

Figure 1A:
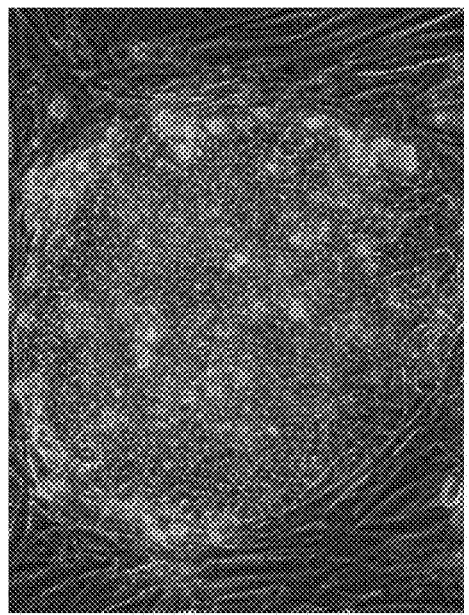
Figure 1B:
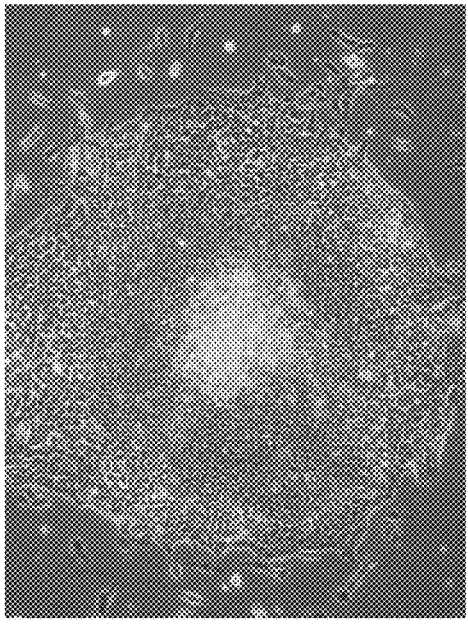
Figure 1C:
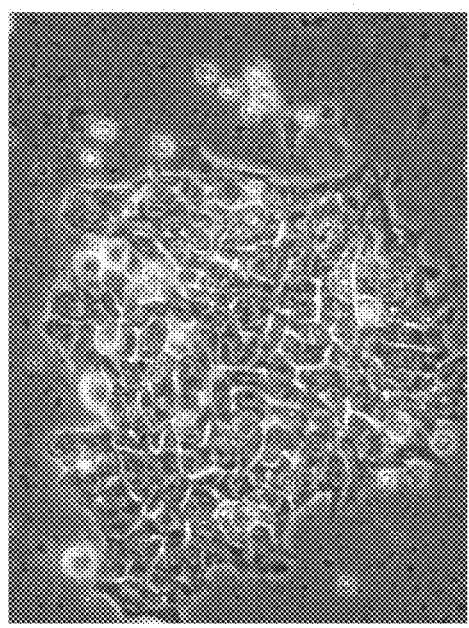
Figure 1D:
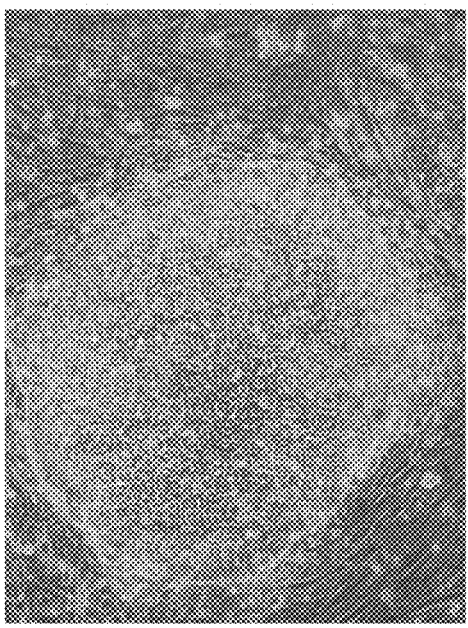

FIGS. 1a-1d are photomicrographs depicting the morphology of undifferentiated hES colonies and hES single cells grown in various culture systems in the presence of the TGFβ-containing culture media. FIG. 1a—I4 hESCs cultured for 28 passages on a Matrigel™ matrix in the presence of the D1 medium; FIG. 1b—I4 hESCs cultured for 9 passages on MEFs in the presence of the HA16 medium; FIG. 1c—I4 hESCs cultured for 20 passages on foreskins fibroblasts in the presence of the D2 medium; FIG. 1d—I4 hESCs cultured for 11 passages on a human fibronectin matrix in the presence of the D2 medium. Note the undifferentiated morphology after prolonged culturing with the unique serum-free, serum replacement-free and protein carrier-free TGFβ-containing media types. Magnifications were ×15 for FIGS. 1a-1d.

FIGS. 2a-2c are photomicrographs depicting undifferentiated hES colonies stained with surface markers specific to the hESC undifferentiated stage. I4 hESCs were cultured for 36 passages on a Matrigel™ matrix in the presence of the D1 medium and stained with TRA-1-60 (FIG. 2a), SSEA4 (FIG. 2b) and TRA-1-81 (FIG. 2c); Magnifications were ×20 for FIGS. 2a-2c.

Figure 3B:
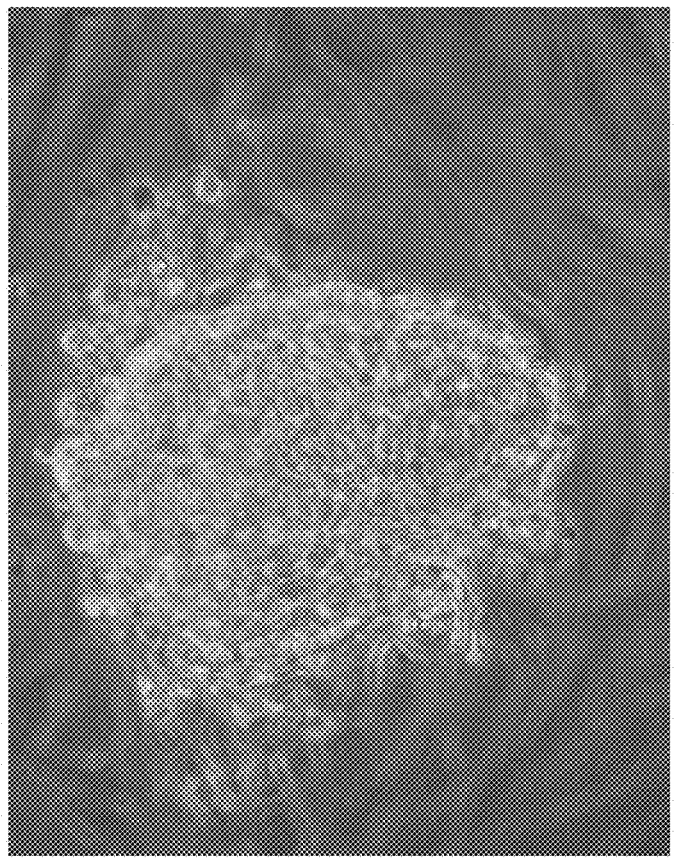
Figure 3A:
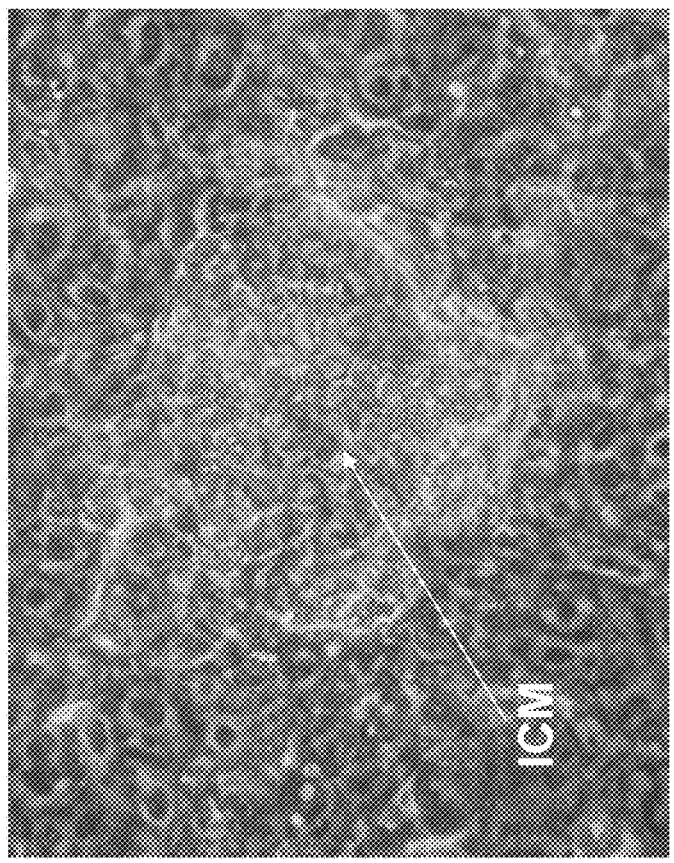

FIGS. 3a-3b are photomicrographs depicting the derivation of a new hESC line under xeno-free conditions on foreskin fibroblasts using the HA16 medium. FIG. 3a—the cultured embryo at first passage (p-1), arrow points at the inner cell mass (ICM); FIG. 3b—the isolated ICM at passage 2 (p-2). Magnifications were ×20 for FIGS. 3a-3b.

Figure 4C:
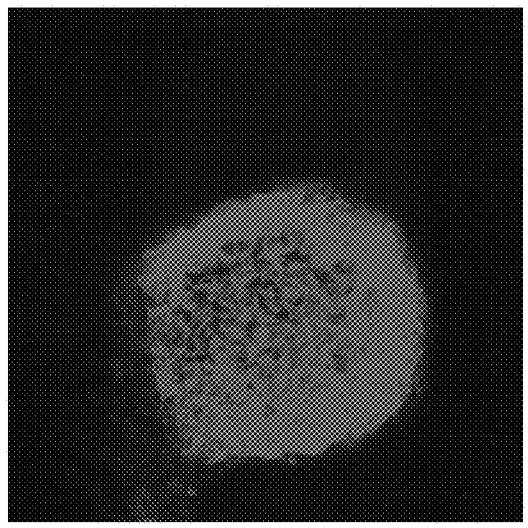
Figure 4B:
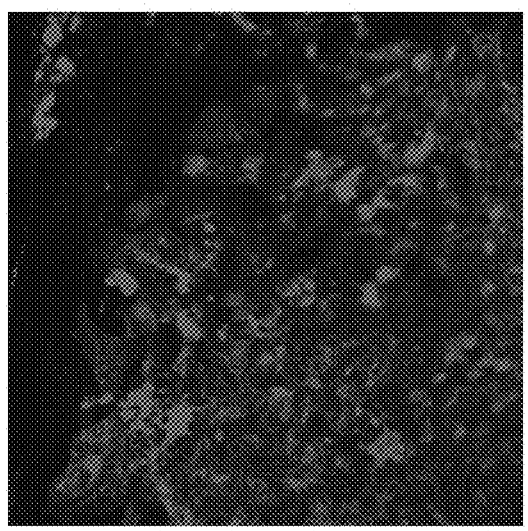
Figure 4A:
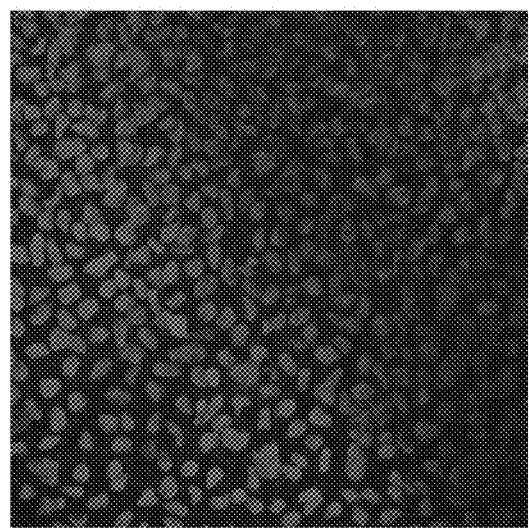

FIGS. 4a-4c are photomicrograph depicting immunostaining of hESCs cultured for three passages in suspension in the presence of the D2 medium. Shown is the expression of Oct4 (FIG. 4a), TRA-1-60 (FIG. 4b) and TRA-1-81 (FIG. 4c); Magnifications were ×63 for FIGS. 4a-4c.

Figure 5A:
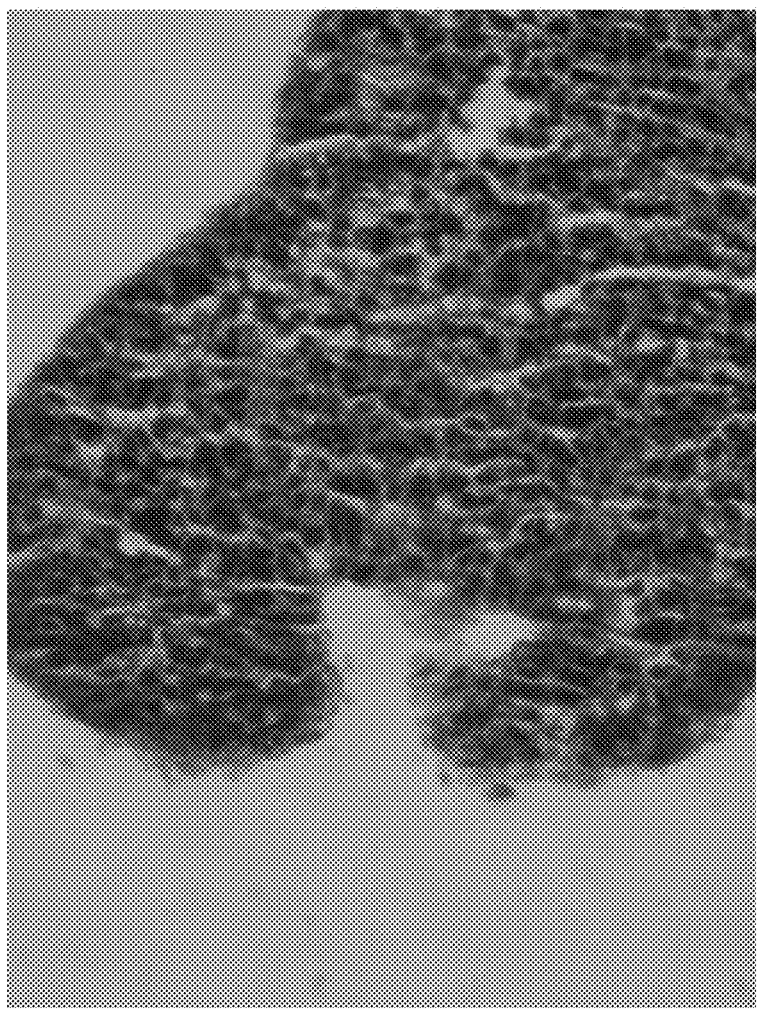
Figure 5C:
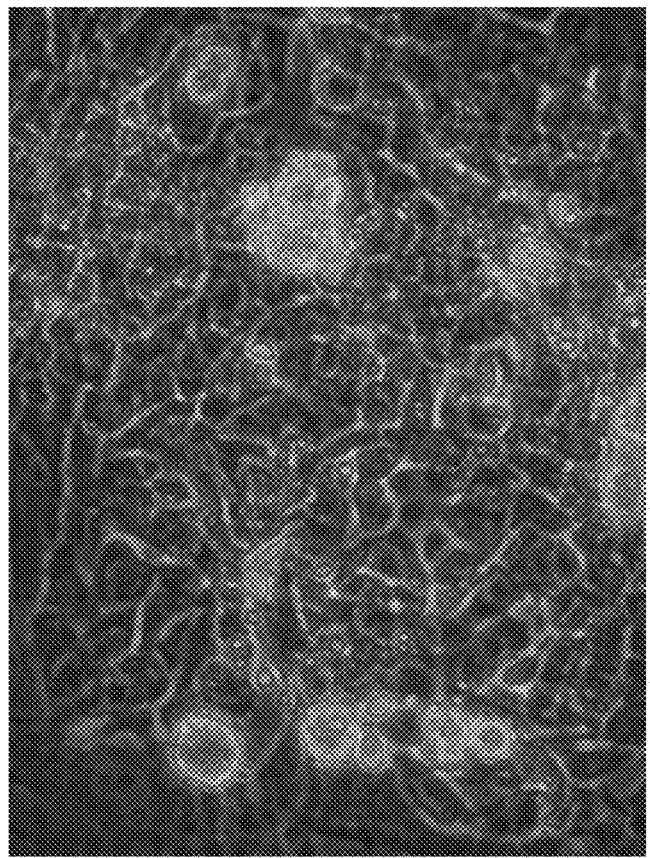
Figure 5B:
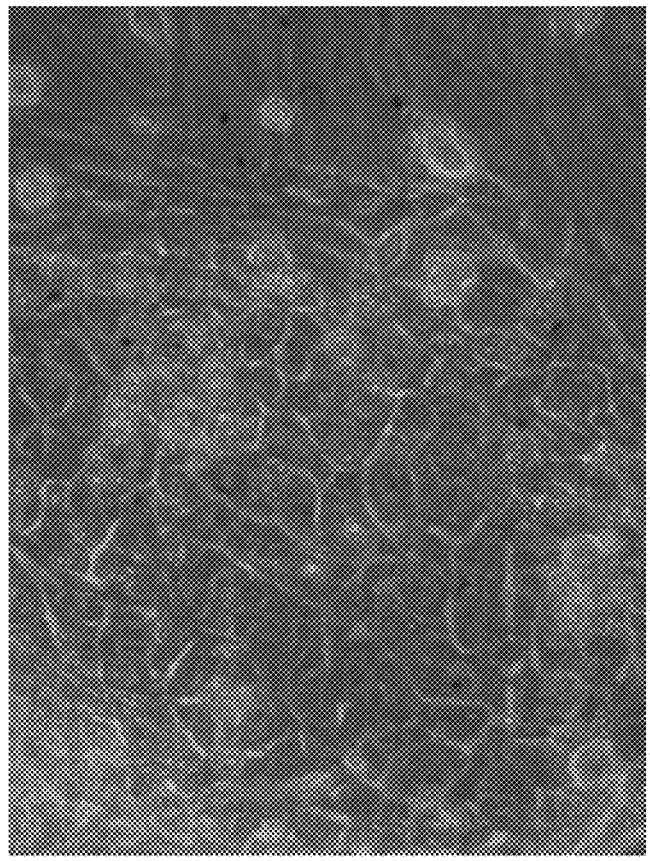
Figure 5D:
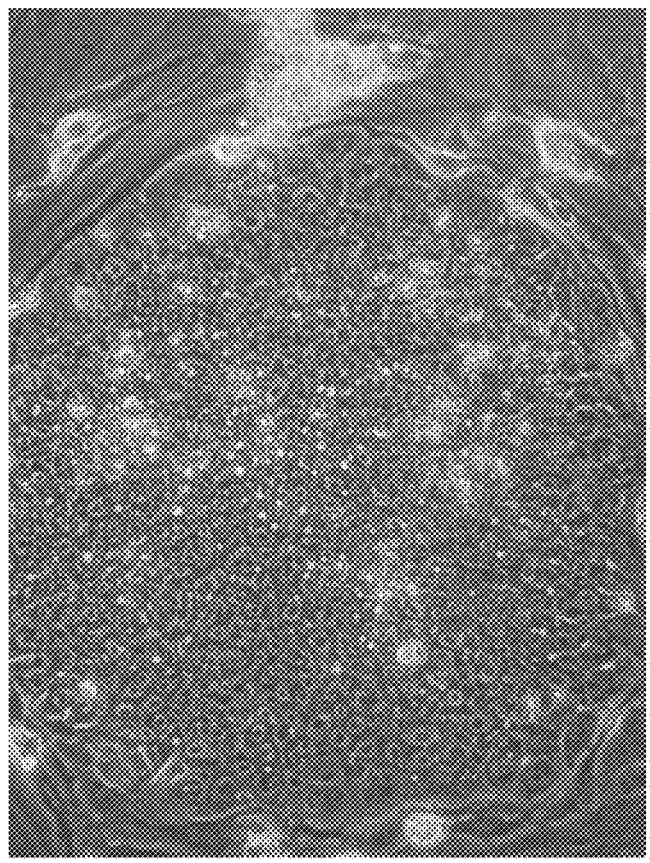
Figure 5E:
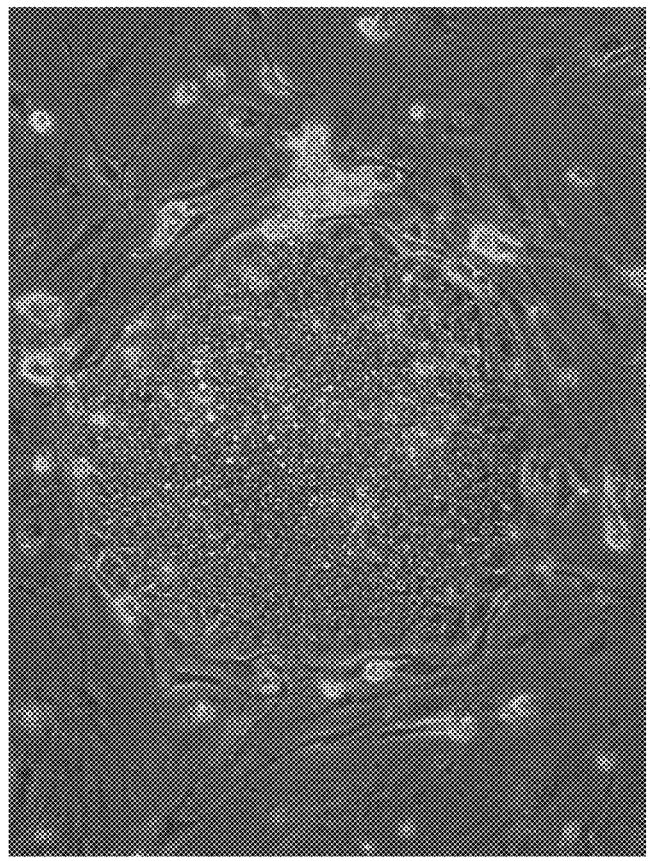
Figure 5G:
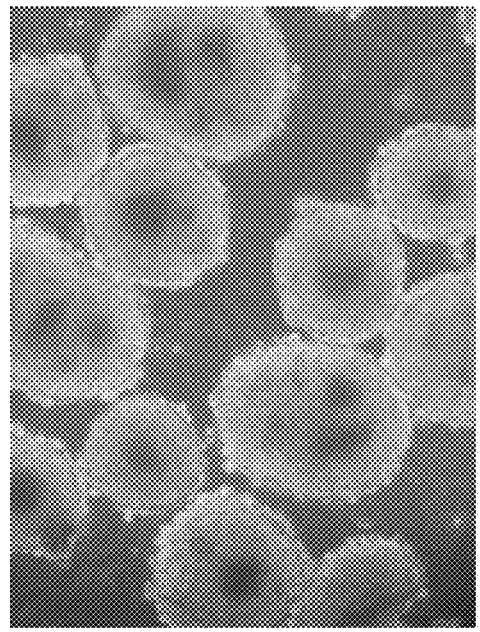
Figure 5F:
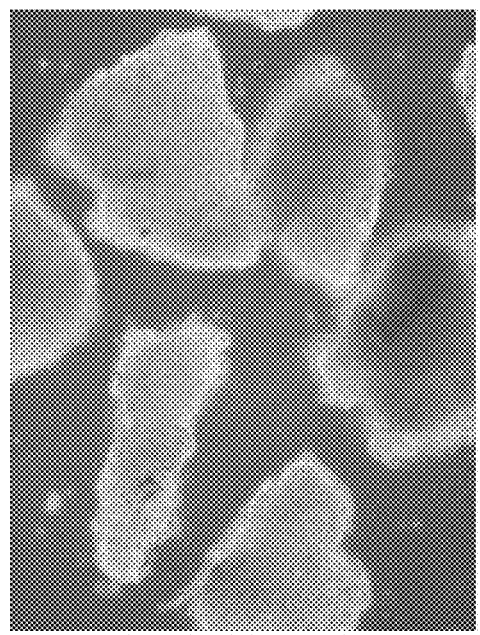

FIGS. 5a-5g are photomicrographs depicting histological sections and morphology of suspended hESCs culture. FIG. 5a-Histology of a hESC clump (the I4 hESC line) cultured for 3 passages in suspension in the presence of the D1 medium and stained with H&E. Note that the hESC clump is homogeneous, containing small cells with large nuclei typical for hESCs morphology. Magnification was X 20. FIGS. 5b-5c—I4 hESCs were cultured for 3 passages in suspension in the presence of the D2 medium and were then re-cultured on MEFs. Shown is the morphology of the colonies (as photographed using an inverted microscope) after re-culturing on MEFs (magnification ×15 for FIGS. 5b-5c). Note the typical undifferentiated morphology of the hESCs. FIGS. 5d-5e—I4 hESCs were cultured for 16 passages in suspension in the presence of the CM100F medium and were then re-cultured on MEFs. Shown is the morphology of colonies after re-culturing on MEFs. Note the typical undifferentiated morphology of the hESCs. Magnification X15 for FIGS. 5d-5e. FIGS. 5f-g—I4 hESCs were cultured for 7 passages in suspension in the presence of the HA19 medium (FIG. 5f) or for 10 passages in the presence of the CM100F medium (FIG. 5g). Magnification ×10 for FIGS. 5f-5g.

FIGS. 6a-6d are RT-PCR analyses depicting the expression of representative genes of the undifferentiated state of hESCs cultured in suspension in the presence of the HACM100, CM100F or the HA19 medium. Lane 1—I-4 hESCs cultured for 1 passage in suspension in the presence of the HACM100 medium (serum or serum replacement-free, IL6RIL6-containing medium). Lane 2—I-4 hESCs cultured for 1 passage in suspension in the presence of the CM100F medium (IL6RIL6 and serum replacement-containing medium). Lane 3—I-4 hESCs cultured for 7 passages in suspension in the presence of the HA19 medium (serum or serum replacement-free, protein carrier-free, $TGF\beta_3$-containing medium). Lane 4—I-4 hESCs cultured for 2 passages in suspension in the presence of the HA19 medium and then re-cultured on MEFs for additional 6 passages. FIG. 6a—Oct4; FIG. 6b—Rex1; FIG. 6c—Sox2; FIG. 6d—Nanog; RT mix were tested and found negative for all tested genes. All samples were tested for β-actin and were found evenly positive.

Figure 7A:
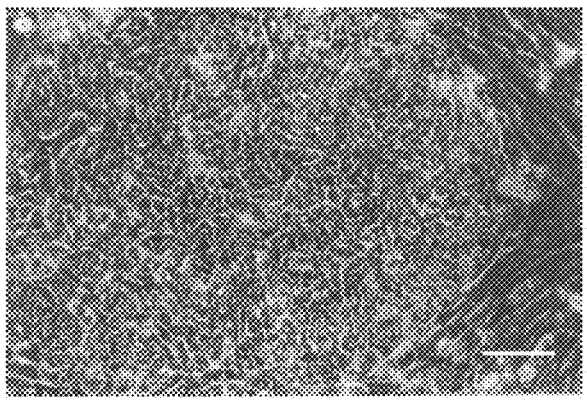
Figure 7B:
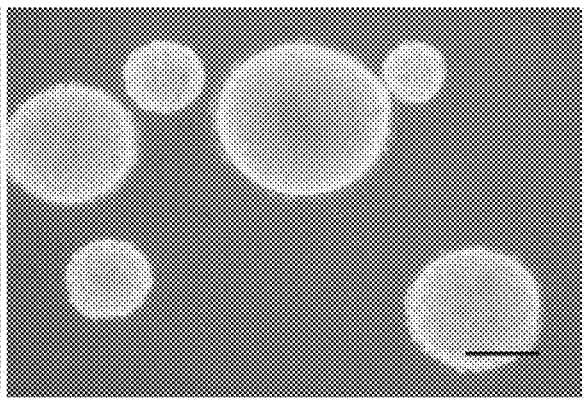
Figure 7C:
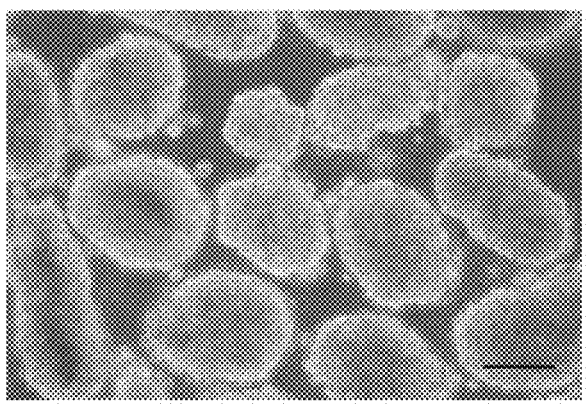
Figure 7D:
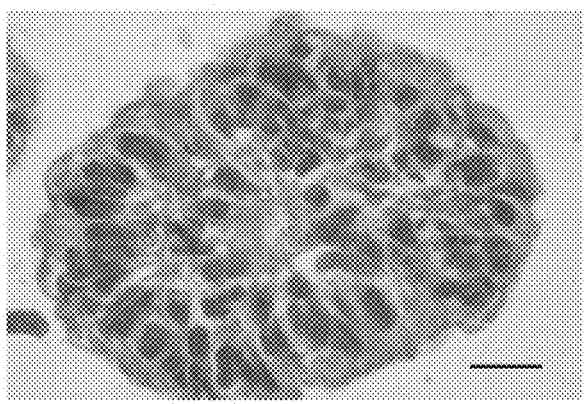
Figure 7E:
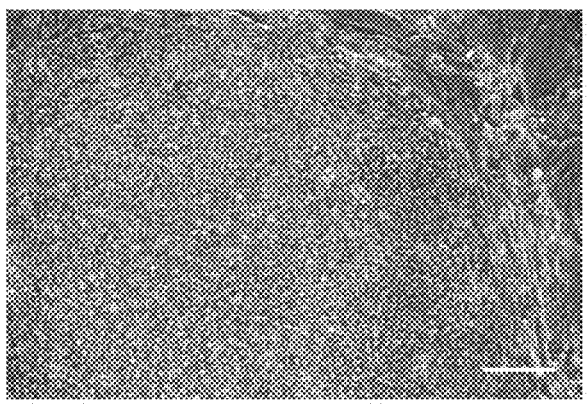
Figure 7F:
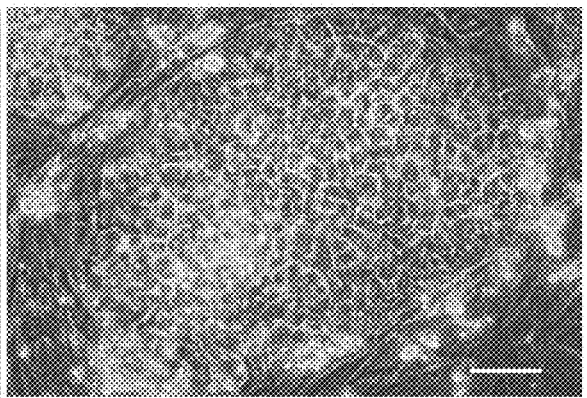

FIGS. 7a-7f are photomicrographs depicting the morphology of hESCs cultured in suspension under non-dynamic conditions (i.e., static culture) or 2-dimensional (2D) cultures in the presence of the CM100F medium (including the IL6RIL6 chimera) (unless stated otherwise). FIG. 7a-Phase contrast image of an undifferentiated hESC colony from 13 cell line cultured for 12 passages on human fibronectin (a 2-D culture). Bar 200 μM; FIG. 7b—Image of neurosphere-like structures representing a differentiation "background" occurring in up to 5% of 16 hES cells when cultured in suspension. Bar 300 μM; FIG. 7c—Undifferentiated 13 hES cells, cultured in suspension for 43 passages. Bar 300 μM; FIG. 7d-Histological section of a clump of undifferentiated cells from 13 hES cells cultured in suspension for 32 passages. Bar 50 μM; FIG. 7e-Phase contrast image of a hESC colony formed by 13 cells cultured for 10 passages in suspension and re-cultured on MEFs (passage one with MEFs). Bar 200 μM; FIG. 7f-A hESC colony formed by 13 cells cultured for 36 passages in suspension and re-cultured on fibronectin (passage 10). Bar 150 μM.

FIGS. 8a-8d are fluorescent immunostaining analyses depicting the expression of undifferentiated markers by hESCs cultured in suspension under non-dynamic conditions in the presence of the CM100F medium (including the IL6RIL6 chimera). FIG. 8a-hESC line I3 cultured for 42 passages in suspension and stained with anti-Oct4 antibodies. Bar 200 μM; FIG. 8b-hESC line 13 cultured for 42 passages in suspension and stained with anti-TRA-1-60 antibodies. 200 μM; FIG. 8c-hESC line I3 cultured for 32 passages in suspension and stained with anti-TRA-1-81 antibodies. 150 μM; FIG. 8d-hESC line I3 cultured for 32 passages in suspension and stained with anti-SSEA4 antibodies. 200 μM.

Figure 9:
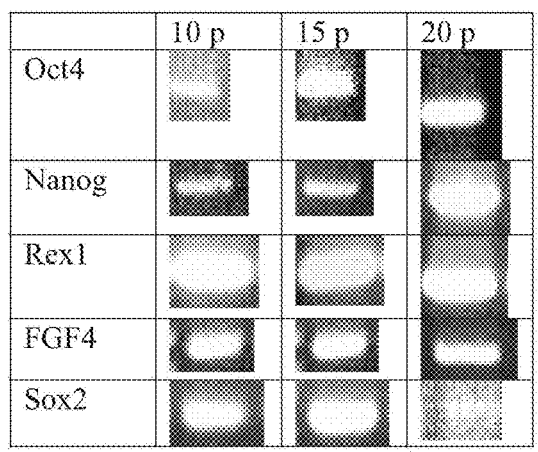

FIG. 9 depicts RT-PCR analyses demonstrating the expression of undifferentiated markers (Oct4, Nanog, Rex1, FGF4 and Sox2) in hESCs cultured in suspension under non-dynamic conditions in the presence of the CM100F medium. The I4 hESCs were cultured for 10 (10 p), 15 (15 p) and 20 (20 p) passages in suspension. Similar results were demonstrated for I3 and I6 hESCs when cultured in suspension in the same culture medium, each for 10, 15 and 20 passages (data not shown). RT mix for all genes were negative.

Figure 10A:
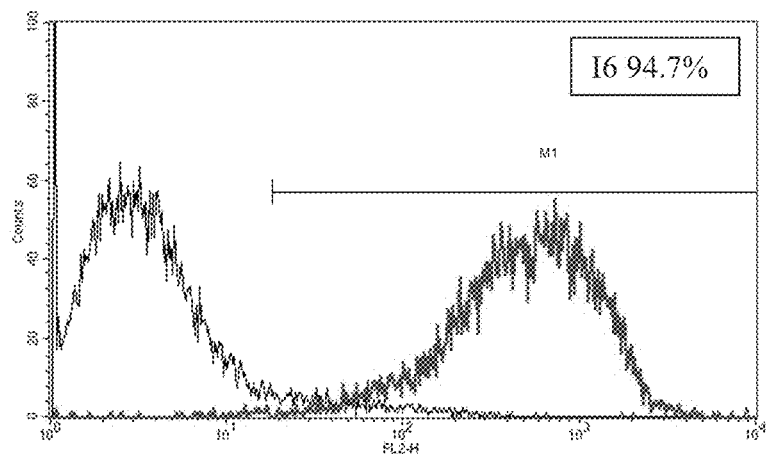
Figure 10B:
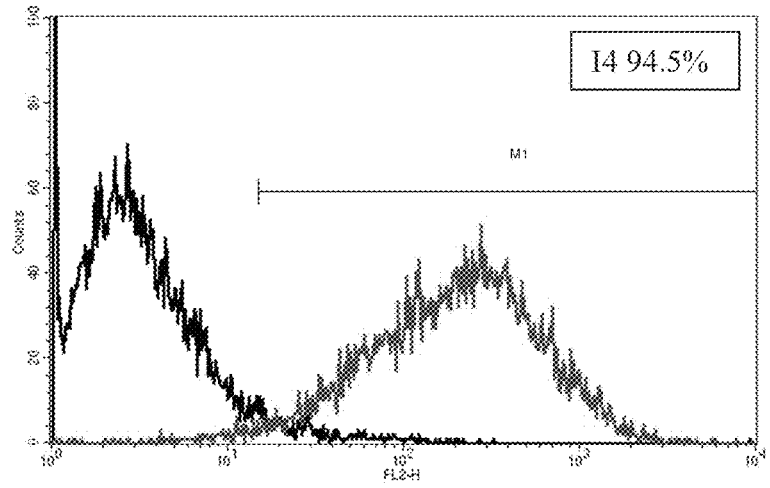
Figure 10C:
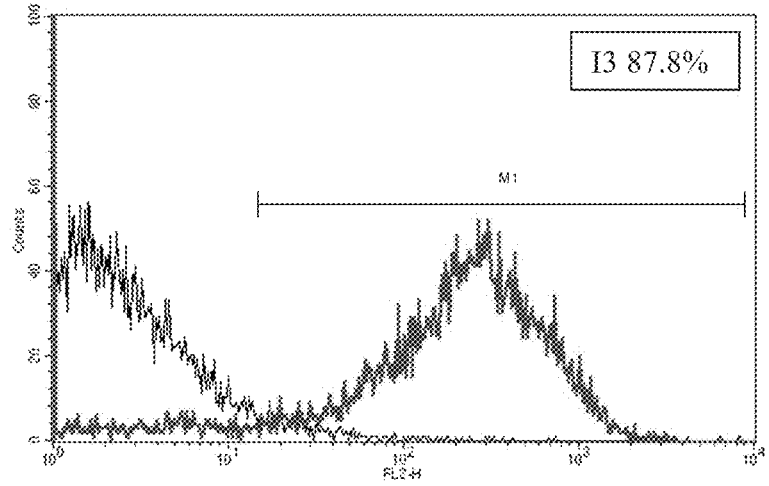

FIGS. 10a-10c are flow cytometry analyses of hESCs cultured in suspension under non-dynamic conditions in the presence of the CM100F medium and stained with SSEA4. FIG. 10a—the I6 at passage 20 in suspension; FIG. 10b—the I4 at passage 30 in suspension; FIG. 10c—the I3 at passages 34 in suspension. The percentages of SSEA4-positive cells (indicating undifferentiated cells) in each cell culture were as follows: I6, 94.7%; I4, 94.5%; I3 87.8%. It should be noted that the clumps of differentiated hESCs in the I3 culture (which consisted of 12% of the cells at passage 34) were removed from the culture and following additional 3 passages 95% of the I3 hESCs expressed the SSEA4 marker (data not shown). These results demonstrate that as in 2-D cultures it is possible to remove differentiated colonies and continue culturing of undifferentiated human ESCs.

Figure 11A:
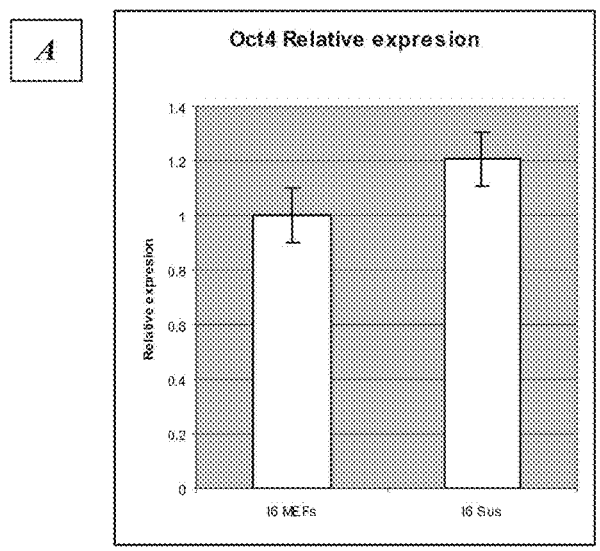
Figure 11B:
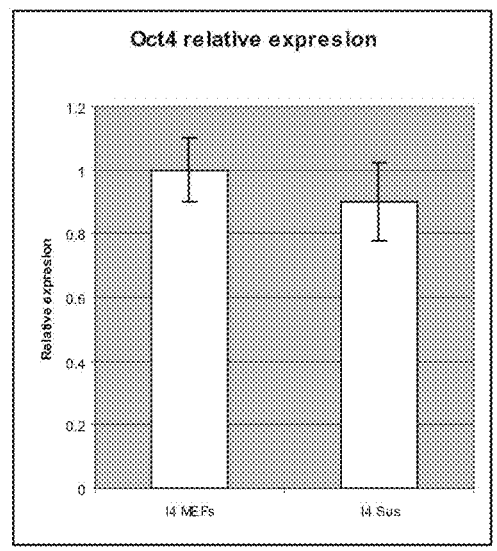

FIGS. 11a-11b are real time PCR analyses depicting relative expression of Oct4 in I6 (FIGS. 11a) and I4 (FIG. 11b) hESCs that were cultured for 10 passages in suspension under non-dynamic conditions in the presence of the CM100F medium. The expression levels were compared to cells from the same cell line cultured continuously on MEFs, which was used as calibrator. Similar results were obtained when cells cultured for 15 and 20 passages in suspension were used (data not shown).

FIGS. 12a-12d are photomicrographs depicting representative histological sections of EBs (FIG. 12a) and teratomas (FIGS. 12b-d). FIGS. 12a—14-days-old cystic EB formed by I4 hESCs cultured for 8 passages in suspension under non-dynamic conditions in the presence of the CM100F medium. Bar 200 μM. Teratomas sections formed by I4 hESCs cultured for 9 passages in suspension in the presence of the CM100F medium created tissues representing of the three embryonic germ layers, including; myelinated nerve (ectoderm) (FIG. 12b), cartilage tissue (mesoderm) (FIG. 12c), and secretory glands-like structures (endoderm) (FIG. 12d). Bar 250 μM for FIGS. 12a, and 200 μM for FIGS. 12b-12d.

Figure 13E:
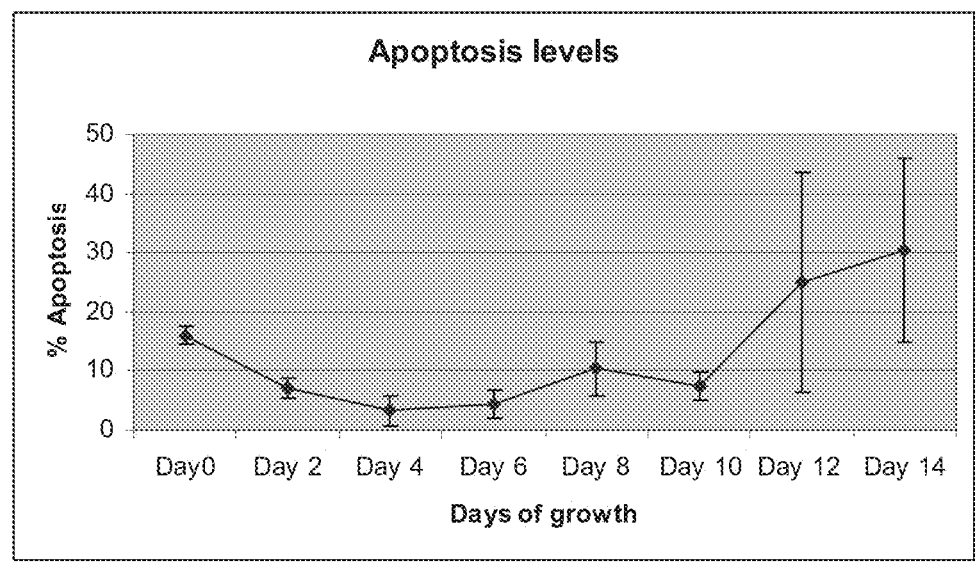

FIGS. 13a-13h depict cell growth (FIGS. 13a-d) and apoptosis (FIGS. 13e-h). I4 hESCs cultured for more than 20 passages in suspension under non-dynamic conditions in the presence of the CM100F medium were used to measure the culture system kinetics. The cells were cultured without splitting for 14 days and the following parameters were measured: increase in clumps diameter (measured in μm) during 14 days of continuous culture (FIG. 13a); clumps cultured for 2, 6 and 14 days representing the increase in size (FIGS. 13b-13d). Bar 300 μM; apoptosis percentage of cells cultured for 14 days in suspension (FIG. 13e); and apoptotic cells within clumps cultured for 2, 6 and 14 days (FIGS. 13f-13h). Note that apoptotic cells in 14 days old clumps are concentrated at the center. Bar 150 μM.

Figure 14A:
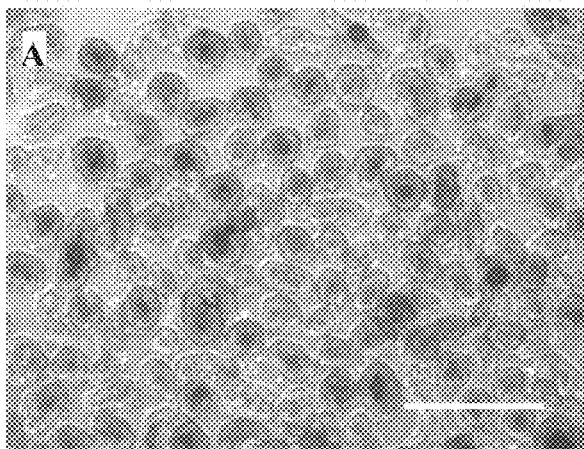
Figure 14B:
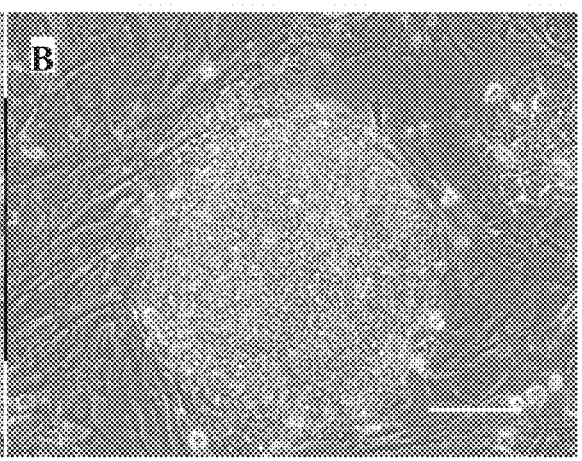
Figure 14C:
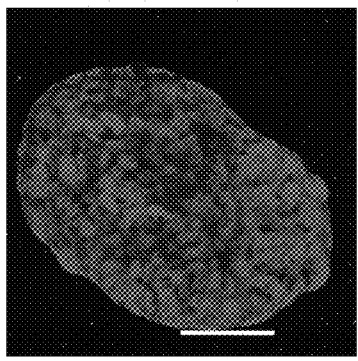
Figure 14D:
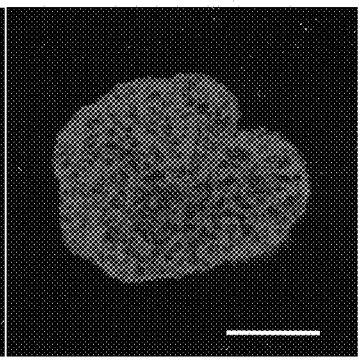
Figure 14E:
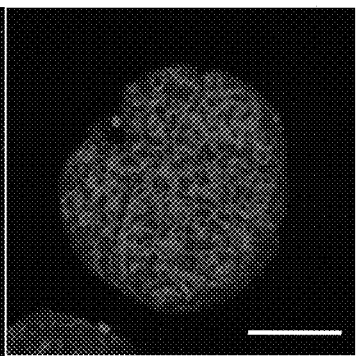
Figures 14F, 14G:
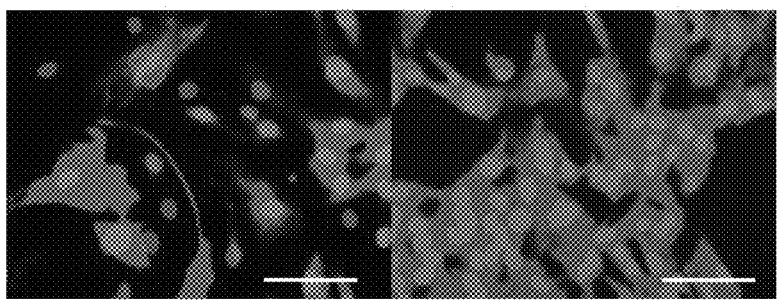
Figure 14H:
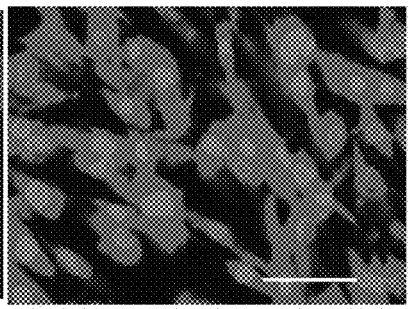

FIGS. 14a-14h are photomicrographs depicting dynamic culture using Erlenmeyer's. FIGS. 14a—I3 hESC clumps cultured for 1 month in Erlenmeyer in the presence of the CM100F medium. Bar 400 μM; FIG. 14b-colony formed by the cells of FIG. 14a after re-culturing for 1 passage (about 5 days) on MEFs. Bar 200 μM. FIGS. 14c-14e—Images of fluorescent immunostaining analyses of 13 hESCs cultured for 4 months in Erlenmeyer in the presence of the CM100F medium using Oct4 (FIG. 14c), SSEA4 (FIG. 14d), and TRA-1-60 (FIG. 14e). Note that the cultured hESCs were positively stained with Oct4, SSEA4 and TRA-1-60, markers of the undifferentiated state. Size bars 200 μM. When the cells (after 1 month of culture in Erlenmeyer) were transferred to serum containing medium they formed EBs. EB were re-plated on Gelatin and positively stained with β-tubulin (FIG. 14f), troponin (FIG. 14g), and PSA-NCAM (FIG. 14h). Size bars 100 μM.

FIGS. 15a-15d are Western blot analyses for STAT3 (FIG. 15b), phosphorylated STAT3 (FIG. 15a), gp130 (FIGS. 15c) and β-actin (control) (FIG. 15d), depicting possible involvement of the IL6RIL6 chimera in cells self-maintenance while cultured in suspension under non-dynamic conditions in the presence of the CM100F medium. Human ESCS were cultured for 24 hours in the CM100F medium without the IL6RIL6 chimera and then in CM100F with the chimera as indicated for 0, 30 minutes, 180 minutes and 24 hours. Trigger experiment demonstrated increase in proteins expression 30 minutes after retrieving the IL6RIL6 chimera, which holds after 24 hours. Lane 1-13 cultured for 44 passages in suspension in the presence of the IL6RIL6 chimera; lane 2-13 cells cultured 37 passages in suspension 24 hours after removing the chimera; lane 3-13 cells cultured 37 passages in suspension 30 minutes after the chimera was returned to the medium; lane 4-3 hours after the chimera was returned to the medium and lane 5-24 hours after the chimera was returned to the culture medium.

FIG. 16 is a graph depicting the percentages of differentiating clumps while culturing in suspension under non-dynamic conditions in the presence of the CM100F medium with increasing concentrations of anti-gp130 added to culture medium. Note the increase in cell differentiation following increasing concentrations of the anti-gp 130 antibody.

FIGS. 17a-17b are images of clumps depicting hESC clump morphology while culturing in the presence of the CM100F medium and 250 ng/ml of the anti-gp 130 antibody. FIG. 17a—depicts morphology of undifferentiated hESC clumps in the presence of the antibody. FIG. 17b—depicts morphology of differentiated hESC clump in the presence of the antibody. Bar 150 µM.

Figure 18B:
Figure 18A:
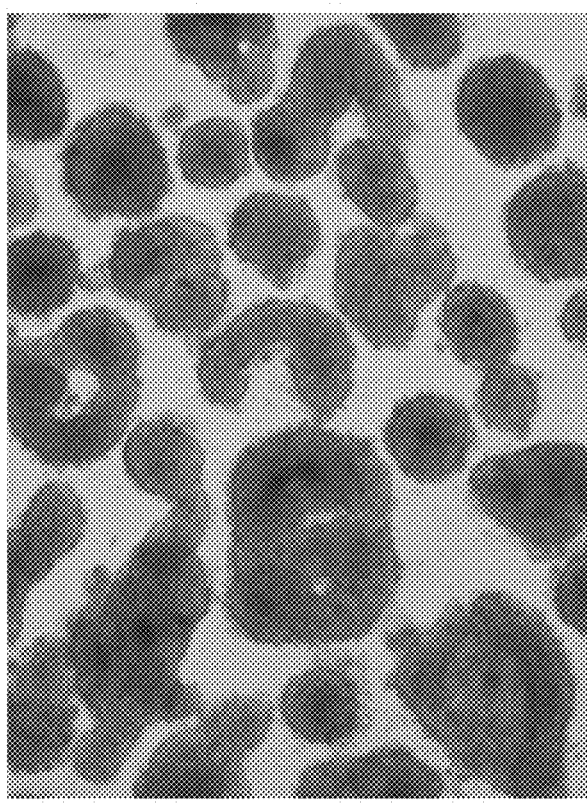
Figure 18D:
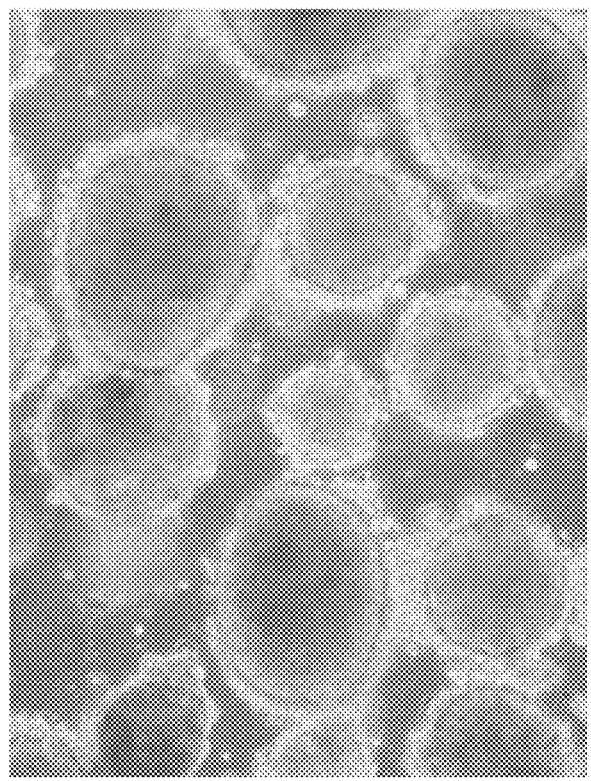
Figure 18C:
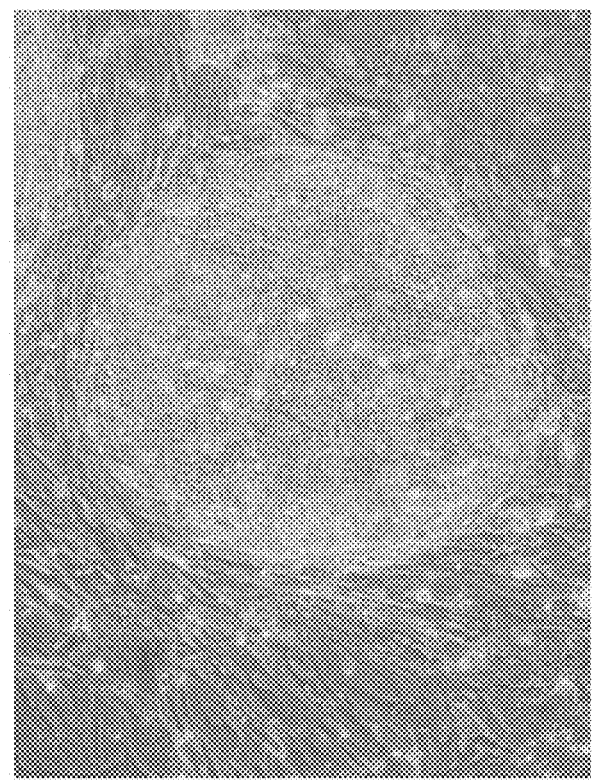
Figure 18E:
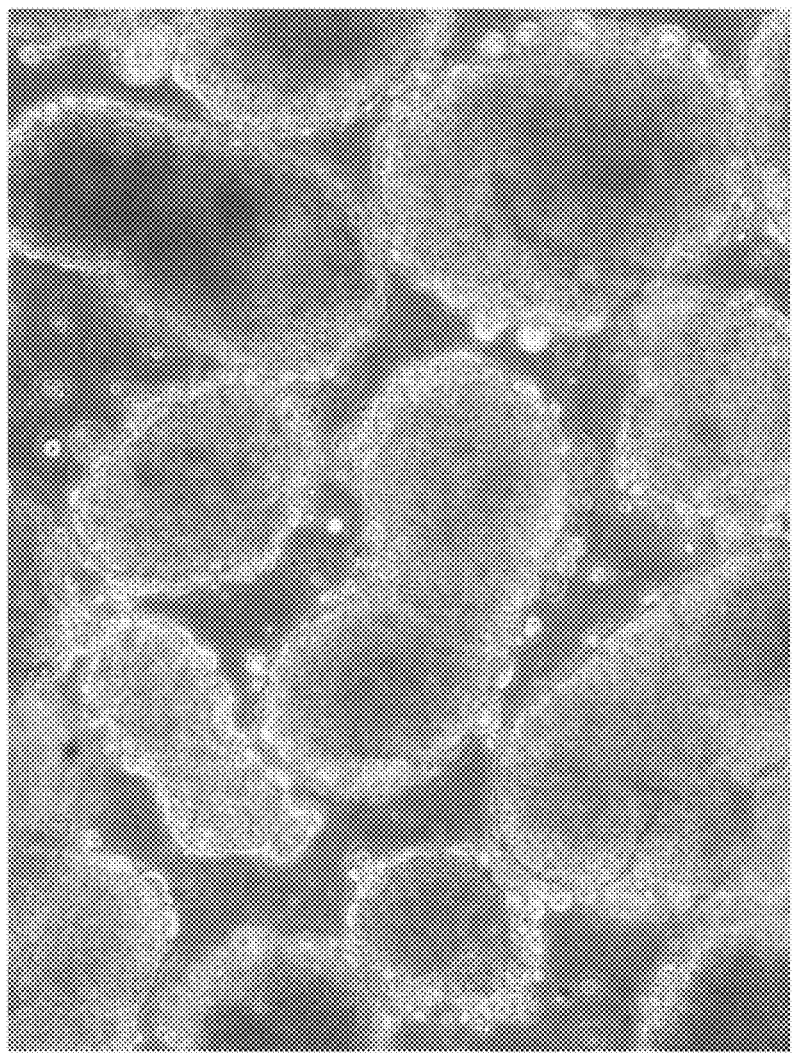

FIGS. 18a-18e depict undifferentiated human ESCs cultured in suspension (under non-dynamic conditions with the yFIL25+ (FIG. 18a), yFL1 (FIG. 18b), TLF (FIGS. 18c and e) and yFL3 (FIG. 18d) culture media. FIG. 18a-Clumps of 14 cells cultured for 16 passages in suspension with yFIL25+ medium; FIG. 18b-Clumps of 13 cells cultured for 18 passages in suspension with yFL1 medium; FIG. 18c-hESCs colony from 13 cultured with TLF on MEFs for 13 passages after 10 passages in suspension; FIG. 18d-Clumps of 13 cells cultured for 1 passage in suspension with yFL3 medium; FIG. 18e-Clumps of 14 cells cultured for 18 passages in suspension with TLF medium.

Figure 19B:
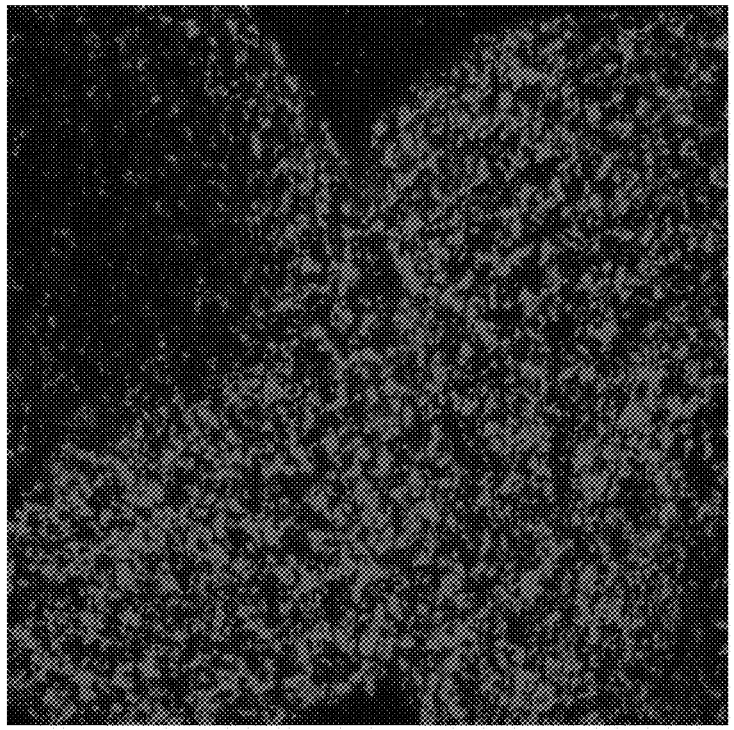
Figure 19A:
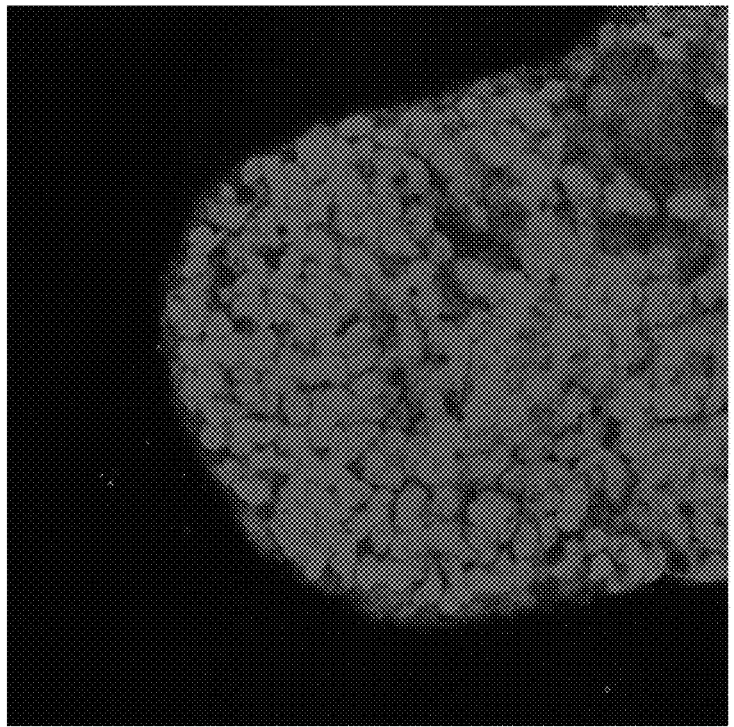
Figure 19D:
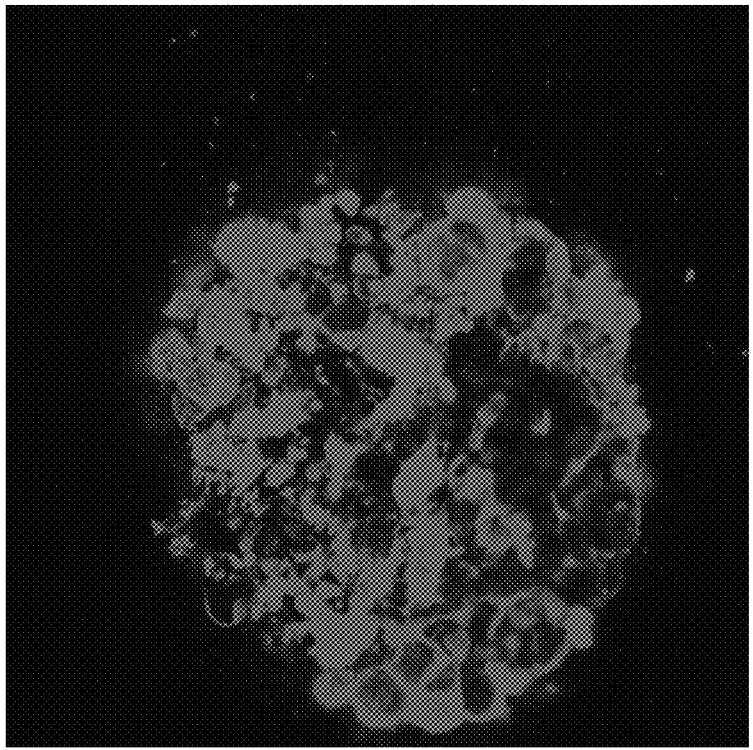
Figure 19C:
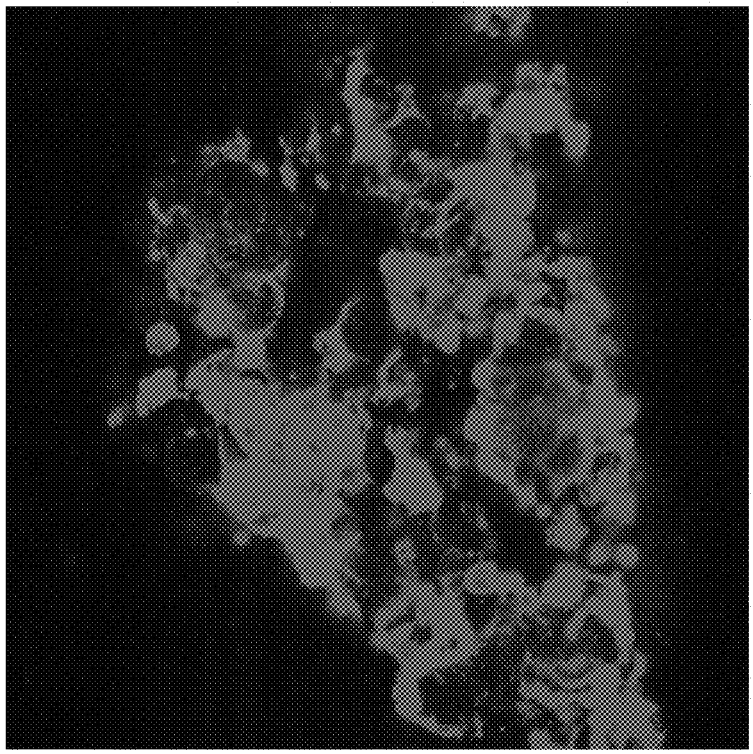

FIGS. 19a-19d are photomicrographs depicting undifferentiated human ESCs cultured under non-dynamic conditions (static) in suspension in the presence of the yFIL25+ (FIG. 19a), TLF (FIGS. 19b-19c) and yFL3 (FIG. 19d). FIG. 19a—is a photomicrograph depicting clumps of I4 hESCs cultured for 18 passages in suspension with yFIL25+ medium and stained with Oct4; FIG. 19b—is a photomicrograph depicting clumps of I4 human ESCs cultured for 31 passages in suspension with TLF medium and stained with SSEA4; FIG. 19c—is a photomicrograph depicting clumps of I4 cells cultured for 31 passages in suspension with TLF medium and stained with TRA-1-60; FIG. 19d—is a photomicrograph depicting clumps of I4 cells cultured for 18 passages in suspension with yFL3 medium and stained with TRA-1-81.

Figure 20:
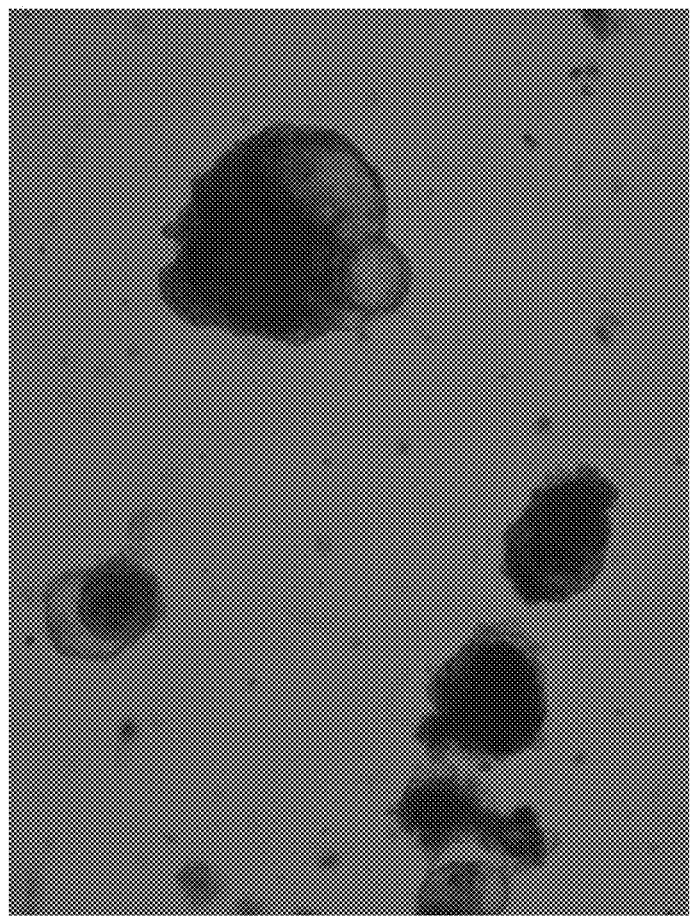

FIG. 20 is a photomicrograph depicting EBs formed from 14 human ESCs which were cultured for 24 passages in suspension under static conditions with TLF medium. For EB formation, the hESCs were transferred to serum containing medium (which is devoid of the LIF and TGFβ1).

DESCRIPTION OF SPECIFIC EMBODIMENTS OF THE INVENTION

The present invention is of a method of expanding and maintaining embryonic stem cells (ESCs) in the undifferentiated state in a suspension culture. In addition, the present invention is of methods of generating lineage-specific cells from ESCs which were expanded by the method of the present invention and which can be used cell-based therapy.

The principles and operation of the method of expanding and maintaining ESCs in a suspension culture according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

To facilitate the exploitation of hESCs in both cell-based therapy and use in the pharmaceutical industry for drug screening, identification of drug targets and cell-based compound delivery, hESCs cultures should be scaled-up and optimized. However, culturing of hESCs on any of the currently available 2-dimensional (2-D) culturing systems (i.e., feeder layers or feeder-free matrices) limits the expansion capacity of the cells. On the other hand, when ESCs are removed from their feeder layers or feeder-free matrices and transferred to common suspension cultures, the cells loose their undifferentiated state and rapidly differentiate (Thomson et al., 1998).

To overcome such limitations, Fok and Zandstra (Fok E Y, and Zandstra P W, Stem Cells. 2005, 23: 1333-42) developed stirred-suspension cultures in which the ESCs are attached to glass microcarriers. However, although ESCs cultured under such conditions exhibited typical ESC expression patterns and retained the developmental potential of the starting cell population, the technical difficulties associated with adherence and dissociation of the ESCs from the microcarrier surface limits the robustness potential of such a culturing method. Another study by Gerecht-Nir and Itskovitz-Eldor (disclosed in PCT/IL03/01017) describes a dynamic culturing system for differentiating embryoid bodies or expanding ESCs under non-differentiation conditions. In this system ESCs are seeded in a bioreactor designed to exert random gravity forces. However, PCT/IL03/01017 does not teach non-dynamic suspension culture systems. Another study by Cormier J. et al. (Tissue engineering 12: 3233-3245, 2006) describes culturing for 6 days of mouse embryonic stem cells (mESCs) in a suspension culture in the presence of leukemia inhibitory factor (LIF) and bovine serum under constant agitation. In a later publication (Zur Nieden N I, et al., 2007; J. of Biotechnology 129: 421-432) the authors reported that mESCs cultured in suspension under static conditions lost their undifferentiated and pluripotent state. In addition, the doubling time of the mESCs that were cultured in the dynamic or static suspension cultures using trypsin for passaging every 2 days was only 15 hours (Zur Nieden., et al., Supra), which may lead to chromosomal instability and abnormality (Cowan C A., et al., 2004, N. Engl. J. Med. 350: 1353-1356). In addition, in contrast to mESCs, it is known that LIF cannot maintain human ESCs in an undifferentiated state (Thomson et al, 1998; Reubinof et al, 2000). Thus, to date, continuous culturing of undifferentiated human ESCs in suspension under conditions devoid of substrate adherence (e.g., a carrier) was never demonstrated.

While reducing the present invention to practice, the present inventors have uncovered, through laborious experimentations, that hESCs can be cultured in the undifferentiated state in a suspension culture devoid of substrate adherence and that cells cultured in such conditions maintain all typical hESC characteristics including unlimited proliferation in the undifferentiated state while preserving the pluripotent capacity.

As is shown in FIGS. 4a-4c, 5a-5g, 6a-6d, 8a-8d, 9, 10a-10c, 11a-11b and 18a-18e and described in Examples 2, 3 and 4 of the Examples section which follows, hESCs cultured in a suspension culture devoid of substrate adherence in the presence of a TGF-beta [β]-containing media (e.g., the D1, D2 or HA19 medium), the IL6RIL6 chimera-containing medium (e.g., CM100F or HACM100), soluble IL6 receptor and IL6 (e.g., the yFIL25 medium), or leukemia inhibitory factor (LIF) (e.g., the yFL1, yFL2 or yFL3 media) exhibited typical hESC morphology (e.g., round cells with large nuclei; for example FIGS. 5a-g, 18a-e) and expressed hESCs-specific markers of the undifferentiated state such as Oct 4, TRA-1-60, TRA-1-81, SSEA4, Rex1, Sox2, Nanog and FGF4 (FIGS. 4a-4c, 6a-6d, 8a-8d, 9, 10a-10c, 11a-11b and data not shown). In addition, hESCs cultured in the suspension cultures maintained their pluripotent capacity as evidenced by their ability to form embryoid bodies (EBs) or teratomas containing representative tissues of all three embryonic germ layers (FIGS. 12a-d and data not shown). Thus, these results demonstrate, for the first time, a method of obtaining a scalable culture of hESCs in a defined, xeno-free medium which is suitable for cell-based therapy.

Thus, according to one aspect of the present invention there is provided a method of expanding and maintaining embryonic stem cells in an undifferentiated state. The method is effected by culturing the embryonic stem cells in a suspension culture under culturing conditions devoid of substrate adherence and which allow expansion of the embryonic stem cells in the undifferentiated state, thereby expanding and maintaining the embryonic stem cells in the undifferentiated state.

As used herein the phrase "embryonic stem cells" refers to embryonic cells which are capable of differentiating into cells of all three embryonic germ layers (i.e., endoderm, ectoderm and mesoderm), or remaining in an undifferentiated state. The phrase "embryonic stem cells" may comprise stem cells obtained from the embryonic tissue formed after gestation (e.g., blastocyst) before implantation (i.e., a pre-implantation blastocyst), extended blastocyst cells (EBCs) which are obtained from a post-implantation/pre-gastrulation stage blastocyst, and embryonic germ (EG) cells which are obtained from the genital tissue of a fetus any time during gestation, preferably before 10 weeks of gestation. Preferred embryonic stem cells according to this aspect of the present invention are of a human or primate (e.g., monkey) origin.

The embryonic stem cells of the present invention can be obtained using well-known cell-culture methods. For example, human embryonic stem cells can be isolated from human blastocysts. Human blastocysts are typically obtained from human in vivo preimplantation embryos or from in vitro fertilized (IVF) embryos. Alternatively, a single cell human embryo can be expanded to the blastocyst stage. For the isolation of human ES cells the zona pellucida is removed from a 5-7 day-old blastocyst and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 4-7 days. For further details on methods of preparing human ES cells see Thomson et al., (U.S. Pat. No. 5,843,780; Science 282: 1145, 1998; Curr. Top. Dev. Biol. 38: 133, 1998; Proc. Natl. Acad. Sci. USA 92: 7844, 1995); Bongso et al., (Hum Reprod 4: 706, 1989); and Gardner et al., (Fertil. Steril. 69: 84, 1998).

It will be appreciated that commercially available embryonic stem cells can also be used with this aspect of the present invention. Human ESCs can be purchased from the NIH human embryonic stem cells registry (http://escr.nih.gov). Non-limiting examples of commercially available embryonic stem cell lines are BG01, BG02, BG03, BG04, CY12, CY30, CY92, CY10, TE03 and TE32.

Extended blastocyst cells (EBCs) can be obtained from a blastocyst of at least nine days post fertilization at a stage prior to gastrulation. Prior to culturing the blastocyst, the zona pellucida is digested [for example by Tyrode's acidic solution (Sigma Aldrich, St Louis, MO, USA)] so as to expose the inner cell mass. The blastocysts are then cultured in vitro as whole embryos for at least nine and no more than fourteen days post fertilization (i.e., prior to the gastrulation event) using standard embryonic stem cell culturing methods. For further details of methods of obtaining EBCs see WO2006/040763 to the present inventors.

EG cells are prepared from the primordial germ cells obtained from fetuses of about 8-11 weeks of gestation (in the case of a human fetus) using laboratory techniques known to anyone skilled in the arts. The genital ridges are dissociated and cut into small chunks which are thereafter disaggregated into cells by mechanical dissociation. The EG cells are then grown in tissue culture flasks with the appropriate medium. The cells are cultured with daily replacement of medium until a cell morphology consistent with EG cells is observed, typically after 7-30 days or 1-4 passages. For additional details on methods of preparation human EG cells see Shamblott et al., Proc. Natl. Acad. Sci. USA 95: 13726, 1998 and U.S. Pat. No. 6,090,622.

It will be appreciated that embryonic stem cells in an undifferentiated state are of a distinct morphology, which is clearly distinguishable by the skilled in the art from that of differentiated cells of embryo or adult origin. Typically, undifferentiated embryonic stem cells have high nuclear/cytoplasmic ratios, prominent nucleoli and compact colony formation with poorly discernable cell junctions. Additional features of the undifferentiated state of the embryonic stem cells are further described hereinunder.

As used herein the phrase "expanding embryonic stem cells" refers to obtaining a plurality of embryonic stem cells from a single or a population of embryonic stem cells. Preferably, expanding embryonic stem cells refers also to increasing the number of embryonic stem cells over the culturing period. It will be appreciated that the number of cells which can be obtained from a single embryonic stem cell depends on the proliferation capacity of the cell. The proliferation capacity of an embryonic stem cell can be calculated by the doubling time of the cell (i.e., the time needed for a cell to undergo a mitotic division in the culture) and the period the stem cell can be maintained in the undifferentiated state while in culture (which is equivalent to the number of passages multiplied by the days between each passage).

For example, as described in Example 2 of the Examples section which follows, hESCs could be maintained in the suspension culture of the present invention for at least 80 days while being subjected to 17 serial passaging (culture splitting) which occurred every 4-6 days. Given that the hESCs cultured in suspension exhibited a doubling time of 36 hours (e.g., when cultured on the CM100F medium), a single hESC cultured under these conditions could be expanded to give rise to $2^{45}$ hESCs (i.e., $3.5 \times 10^{13}$ hESCs).

As mentioned, the method according to this aspect of the present invention is effected by culturing the embryonic stem cells in a suspension culture under culturing conditions devoid of substrate adherence and which allow expansion of the embryonic stem cells in the undifferentiated state.

As used herein the phrase "suspension culture" refers to a culture in which the embryonic stem cells are suspended in a medium rather than adhering to a surface.

Thus, the culture of the present invention is "devoid of substrate adherence" in which the embryonic stem cells are capable of expanding without adherence to an external substrate such as components of extracellular matrix, a glass microcarrier or beads.

Culturing according to this aspect of the present invention is effected by plating the stem cells in a culture vessel at a cell density which promotes cell survival and proliferation but limits differentiation. Typically, a plating density of between about $5 \times 10^4$-$2 \times 10^5$ cells per ml is used. It will be appreciated that although single-cell suspensions of stem cells are usually seeded, small clusters such as 10-200 cells may also be used.

In order to provide the ESCs with sufficient and constant supply of nutrients and growth factors while in the suspension culture, the culture medium can be replaced on a daily basis, or, at a pre-determined schedule such as every 2-3 days. For example, replacement of the culture medium can be performed by subjecting the ESC suspension culture to centrifugation for about 3 minutes at 80 g, and resuspension of the formed ESC pellet in a fresh medium. Additionally or alternatively, a culture system in which the culture medium is subject to constant filtration or dialysis so as to provide a constant supply of nutrients or growth factors to the ESCs may be employed.

Since large clusters of ESCs may cause cell differentiation, measures are taken to avoid large ESCs aggregates. Preferably, the formed ESC clumps are dissociated every 5-7 days and the single cells or small clumps of cells are either split into additional culture vessels (i.e., passaged) or remained in the same culture vessel yet with additional culture medium. For dissociation of large ESC clumps, a pellet of ESCs (which may be achieved by centrifugation as described hereinabove) or an isolated ESC clump can be subject to enzymatic digestion and/or mechanical dissociation.

Enzymatic digestion of ESC clump(s) can be performed by subjecting the clump(s) to an enzyme such as type IV Collagenase (Worthington biochemical corporation, Lakewood, NJ, USA) and/or Dispase (Invitrogen Corporation products, Grand Island NY, USA). The time of incubation with the enzyme depends on the size of cell clumps present in the suspension culture. Typically, when hESC cell clumps are dissociated every 5-7 days while in the suspension culture, incubation of 20-60 minutes with 1.5 mg/ml type IV Collagenase results in small cell clumps which can be further cultured in the undifferentiated state. Alternatively, ESC clumps can be subjected to incubation of about 25 minutes with 1.5 mg/ml type IV Collagenase followed by five minutes incubation with 1 mg/ml Dispase, essentially as described under "General Materials and Experimental Methods" of the Examples section which follows. It should be noted that passaging of human ESCs with trypsin may result in chromosomal instability and abnormalities (see for example, Mitalipova M M., et al., Nature Biotechnology, 23: 19-20, 2005 and Cowan C A et al., N. Engl. J. of Med. 350: 1353-1356, 2004), and therefore should be avoided.

Mechanical dissociation of large ESC clumps can be performed using a device designed to break the clumps to a predetermined size. Such a device can be obtained from CellArtis Goteborg, Sweden. Additionally or alternatively, mechanical dissociation can be manually performed using a needle such as a 27 g needle (BD Microlance, Drogheda, Ireland) while viewing the clumps under an inverted microscope.

Preferably, following enzymatic or mechanical dissociation of the large cell clumps, the dissociated ESC clumps are further broken to small clumps using 200 μl Gilson pipette tips (e.g., by pipetting up and down the cells).

The culture vessel used for culturing the ESC in suspension according to the method of this aspect of the present invention can be any tissue culture vessel (e.g., with a purity grade suitable for culturing ESCs) having an internal surface designed such that ESC cultured therein are unable to adhere or attach to such a surface (e.g., non-tissue culture treated cells, to prevent attachment or adherence to the surface). Preferably, in order to obtain a scalable culture, culturing according to this aspect of the present invention is effected using a controlled culturing system (preferably a computer-controlled culturing system) in which culture parameters such as temperature, agitation, pH, and $pO_2$ is automatically performed using a suitable device. Once the culture parameters are recorded, the system is set for automatic adjustment of culture parameters as needed for ESCs expansion.

It will be appreciated that culturing according to the method of this aspect of the present invention can be performed under dynamic conditions (i.e., under conditions in which the ESCs are subject to constant movement while in the suspension culture) or under non-dynamic conditions (i.e., a static culture). For non-dynamic culturing of ESCs, the ESCs can be cultured in uncoated 58 mm petri dishes (Greiner, Frickenhausen, Germany). For dynamic culturing of ESCs, the ESCs can be cultured in spinner flasks [e.g., of 200 ml to 1000 ml, for example 250 ml which can be obtained from CellSpin of Integra Biosciences, Fernwald, Germany; of 100 ml which can be obtained from Bellco, Vineland, NJ; or in 125 ml Erlenmeyer (Corning Incorporated, Corning NY, USA)] which can be connected to a control unit and thus present a controlled culturing system.

The medium used to culture the ESCs in suspension according to the method of this aspect of the present invention can be any culture medium capable of supporting the growth of ESCs while maintaining them in an undifferentiated state. Such a culture medium can be a water-based medium which includes a combination of substances such as salts, nutrients, minerals, vitamins, amino acids, nucleic acids, proteins such as cytokines, growth factors and hormones, all of which are needed for cell proliferation and are capable of maintaining the ESCs in an undifferentiated state. For example, a culture medium according to this aspect of the present invention can be a synthetic tissue culture medium such as Ko-DMEM (Gibco-Invitrogen Corporation products, Grand Island, NY, USA), DMEM/F12 (Biological Industries, Biet Haemek, Israel), Mab ADCB medium (HyClone, Utah, USA) or DMEM/F12 (Biological Industries, Biet Haemek, Israel) supplemented with the necessary additives as is further described hereinunder. Preferably, all ingredients included in the culture medium of the present invention are substantially pure, with a tissue culture grade.

Preferably, in order to obtain a well-defined, xeno-free ESC culture which can be easily scalable and is suitable for both cell based-therapy and use in the pharmaceutical industry (e.g., for drug screening, identification of drug targets and cell-based compound delivery), the culture medium used by the method of this aspect of the present invention should be well-defined (i.e., with known and constant components) and xeno-free (i.e., devoid of xeno contaminants).

Preferably, the culture medium used by the method of this aspect of the present invention is serum-free, serum replacement-free, xeno-free, feeder-free (i.e., devoid of feeder cells) and protein carrier-free.

Serum or serum replacement are usually added to most culture media which are designed for culturing stem cells, and particularly, embryonic stem cells, in order to provide the cells with the optimal environment, similar to that present in vivo (i.e., within the organism from which the cells are derived, e.g., a blastocyst of an embryo or an adult tissue of a postnatal individual). However, while the use of serum which is derived from either an animal source (e.g., bovine serum) or a human source (human serum) is limited by the significant variations in serum components between individuals and the risk of having xeno contaminants (in case of an animal serum is used), the use of the more defined composition such as the currently available serum Replacement™ (Gibco-Invitrogen Corporation, Grand Island, NY USA) may be limited by the presence of Albumax (Bovine serum albumin enriched with lipids) which is from an animal source within the composition (International Patent Publication No. WO 98/30679 to Price, P. J. et al).

A protein carrier refers to a protein which acts in the transfer of proteins or nutrients (e.g., minerals such as zinc) to the cells in the culture. Such protein carriers can be, for example, albumin (e.g., bovine serum albumin), Albumax (lipid enriched albumin) or plasmanate (human plasma isolated proteins). Since these carriers are derived from either human or animal sources their use in hESCs cultures is limited by batch-specific variations and/or exposure to pathogens. On the other hand, the recombinant human albumin, which is substantially pure and devoid of animal contaminants is highly expensive, thus not commonly used in hESCs cultures. Thus, a culture medium which is devoid of a protein carrier is highly advantageous since it enables a truly defined medium that can be manufacture from recombinant or synthetic materials.

Preferably, a culture medium which is serum-free, serum replacement-free, xeno-free, feeder-free and protein carrier-free can be a culture medium which comprises a TGFβ isoform (for non-limiting examples see the D1, D2, HA16 or HA19 culture media which are described in Examples 1 and 2 of the Examples section which follows).

As used herein the phrase "TGFβ isoform" refers to any isoform of the transforming growth factor beta (β) including TGFβ1 (e.g., *Homo sapiens* TGFβ1, GenBank Accession No. NP_000651), TGFβ2 (e.g., *Homo sapiens* TGFβ2, GenBank Accession No. NP_003229) and TGFβ3 (e.g., *Homo sapiens* TGFβ3, GenBank Accession No. NP_003230) which function through the same receptor signaling system in the control of proliferation, differentiation, and other functions in many cell types. TGFβ acts in inducing transformation and also acts as a negative autocrine growth factor. According to preferred embodiments of the present invention the TGFβ isoform which is included in the culture medium of the present invention is TGFβ1 or TGFβ3. Such TGFβ isoforms can be obtained from various commercial sources such as R&D Systems Minneapolis MN, USA.

As described in Example 2 of the Examples section which follows, the present inventors have used various culture media which contain $TGF\beta_1$ (e.g., the D1 medium which contains 0.12 ng/ml $TGF\beta_1$) or $TGF\beta_3$ (e.g., the D2 medium, the HA16 medium or the HA19 medium which contain 2 ng/ml TGF133) to successfully culture hESCs in a suspension culture and maintain them in the undifferentiated state.

Preferably, $TGF\beta_1$ which is included in the culture medium of this aspect of the present invention is present at a concentration of at least 0.06 ng/ml, more preferably, at least 0.07 ng/ml, more preferably, at least 0.08 ng/ml, more preferably, at least 0.09 ng/ml, more preferably, at least 0.1 ng/ml, more preferably, at least 0.11 ng/ml, even more preferably, at least 0.12 ng/ml.

Preferably, $TGF\beta_3$ which is included in the culture medium of this aspect of the present invention is present at a concentration of at least 0.5 ng/ml, more preferably, at least 0.6 ng/ml, more preferably, at least 0.8 ng/ml, more preferably, at least 0.9 ng/ml, more preferably, at least 1 ng/ml, more preferably, at least 1.2 ng/ml, more preferably, at least 1.4 ng/ml, more preferably, at least 1.6 ng/ml, more preferably, at least 1.8 ng/ml, even more preferably, at least 2 ng/ml.

Preferably, the TGFβ-containing culture medium of this aspect of the present invention further includes basic fibroblast growth factor (bFGF). bFGF can be obtained from any commercial supplier of tissue culture ingredients such as Invitrogen Corporation products, Grand Island NY, USA.

Preferably, the bFGF which is included in TGFβ-containing culture medium of this aspect of the present invention is present at a concentration of at least 2 ng/ml, at least 3 ng, at least 4 ng/ml, at least 5 ng/ml, at least 6 ng/ml, at least 7 ng, at least 8 ng/ml, at least 9 ng/ml, at least 10 ng/ml.

Alternatively, a culture medium which is based on the IL6RIL6 chimera and is serum or serum replacement-free, xeno-free and protein carrier-free can be also used along with the method of this aspect of the present invention.

As used herein the term "IL6RIL6" refers to a chimeric polypeptide which comprises the soluble portion of interleukin-6 receptor (IL-6-R, e.g., the human IL-6-R as set forth by GenBank Accession No. AAH89410 (SEQ ID NO: 32)) (e.g., a portion of the soluble IL6 receptors as set forth by SEQ ID NO: 33 which corresponds to amino acids 112-355 of GenBank Accession No. AAH89410 (SEQ ID NO: 32)) and the interleukin-6 (IL6) (e.g., human IL-6 as set forth by GenBank Accession No. CAG29292) or a biologically active fraction thereof (e.g., a receptor binding domain). Preferably, the IL6RIL6 chimera used by the method according to this aspect of the present invention is capable of supporting the undifferentiated growth of human embryonic stem cells, while maintaining their pluripotent capacity. It will be appreciated that when constructing the IL6RIL6 chimera the two functional portions (i.e., the IL6 and its receptor) can be directly fused (e.g., attached or translationally fused, i.e., encoded by a single open reading frame) to each other or conjugated (attached or translationally fused) via a suitable linker (e.g., a polypeptide linker). Preferably, the IL6RIL6 chimeric polypeptide exhibits a similar amount and pattern of glycosylation as the naturally occurring IL6 and IL6 receptor. For example, a suitable IL6RIL6 chimera is as set forth in SEQ ID NO:31 and in FIG. 11 of WO 99/02552 to Revel M., et al., which is fully incorporated herein by reference.

Preferably, the IL6RIL6 chimera which is included in the culture medium of this aspect of the present invention is present at a concentration of at least 25 ng/ml, preferably at least 50 ng/ml, preferably, at least 100 ng/ml, preferably, at least 200 ng/ml, preferably, at least 300 ng/ml. It should be noted that the concentration of the IL6RIL6 chimera can vary depending on the purity of the chimeric polypeptide following its synthesis or recombinant expression and those of skills in the art are capable of adjusting the optimal concentration depending on such purity.

Preferably, the IL6RIL6-containing culture medium of this aspect of the present invention includes at least 2 ng/ml bFGF, at least 3 ng/ml, at least 4 ng/ml, at least 5 ng/ml, at least 6 ng/ml, at least 7 ng, at least 8 ng/ml, at least 9 ng/ml, at least 10 ng/ml bFGF.

For example, a suitable IL6RIL6-containing culture medium which can be used for culturing the ESC in a suspension culture can be the HACM100 culture medium described under the "General Materials and Experimental Methods" and Example 2 of the Examples section which follows, which was shown capable of maintaining hESCs in an undifferentiated state for at least 1-2 passages.

Still alternatively, a culture medium which is based on soluble interleukin-6 receptor (sIL6R) [e.g., GenBank Accession No. NM_000565.2, NM_181359.1, NP_000556.1, NP_852004.1] and soluble interleukin-6 (IL6) [e.g., GenBank Accession No. NM_000600.1, NP_000591.1] (separately) can be also used along with the method of the present invention. For example, as described in Example 4 of the Examples sections which follows, a culture medium such as the yFIL25 which comprises 25 ng IL6 and 25 ng sIL6R can be used to culture, expand and maintain human ESCs in a pluripotent, proliferative and undifferentiated state for at least 19 passages. Thus, human ESCs cultured in such a culture medium expressed markers characteristics of the undifferentiated state, exhibited normal chromosomal karyotype (as tested after 14 passages) and were capable of forming EBs which included all three embryonic germ layers (pluripotent). Preferably, the sIL6R is present at a concentration of at least 10 nanogram per milliliter (ng/ml), more preferably, at least 15 ng/ml, more preferably, at least 20 ng/ml, e.g., at least 22 ng/ml, 25 ng/ml, 27 ng/ml, or 30 ng/ml. For example, sIL6R can be present at a concentration of 15-30 ng/ml, e.g., 25 ng/ml. sIL6R and IL6 can be obtained, for example, from R&D systems, Minneapolis, MN, USA.

Still alternatively, a culture medium which is based on leukemia inhibitory factor (LIF) [e.g., GenBank Accession No. NM_002309.2 (mRNA) or NP_002300.1 (protein)] can be also used along with the method of the present invention. For example, as described in Example 4 of the Examples sections which follows, a culture medium such as the yFL1, yFL2, or yFL3 can be used to culture, expand and maintain human ESCs in a pluripotent, proliferative and undifferentiated state for at least 18 passages. Thus, human ESCs cultured in such a culture medium expressed markers characteristics of the undifferentiated state, exhibited normal chromosomal karyotype (as tested after 14 passages) and were capable of forming EBs which included all three embryonic germ layers (pluripotent). Preferably, LIF is present at a concentration of at least 1000 units/ml, more preferably, at least 2000 units/ml, more preferably, at least 3000 units/ml. Human recombinant leukemia inhibitory factor (hrLIF) can be obtained from R&D Systems Minneapolis MN, USA.

Still alternatively, a culture medium which is based on leukemia inhibitory factor (LIF) [e.g., GenBank Accession No. NM_002309.2 (mRNA) or NP_002300.1 (protein)] and TGFβ1 can be used along with the method of the present invention. For example, as described in Example 4 of the Examples sections which follows, a culture medium such as the TLF medium can be used to culture, expand and maintain human ESCs in a pluripotent, proliferative and undifferentiated state for at least 31 passages. Thus, human ESCs cultured in such a culture medium expressed markers characteristics of the undifferentiated state, exhibited normal chromosomal karyotype (as tested after 18 passages) and were capable of forming EBs which included all three embryonic germ layers (pluripotent).

It will be appreciated that any of the proteinaceous factors used in the culture medium of the present invention (e.g., the IL6RIL6 chimera, bFGF, TGFβ1, TGFβ3, LIF, sIL6R and IL6) can be recombinantly expressed or biochemically synthesized. In addition, naturally occurring proteinaceous factors such as bFGF and TGFβ can be purified from biological samples (e.g., from human serum, cell cultures) using methods well known in the art.

Biochemical synthesis of the proteinaceous factors of the present invention (e.g., the IL6RIL6 chimera) can be performed using standard solid phase techniques. These methods include exclusive solid phase synthesis, partial solid phase synthesis methods, fragment condensation and classical solution synthesis.

Recombinant expression of the proteinaceous factors of the present invention (e.g., the IL6RIL6 chimera) can be generated using recombinant techniques such as described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680, Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463. Specifically, the IL6RIL6 chimera can be generated as described in PCT publication WO 99/02552 to Revel M., et al. and Chebath J., et al., 1997, which are fully incorporated herein by reference.

For example, to generate the IL6RIL6 chimera, a polynucleotide sequence encoding the IL6RIL6 chimera (e.g., the polypeptide set forth by SEQ ID NO:31) is preferably ligated into a nucleic acid construct suitable for expression in a host cell [i.e., a cell in which the polynucleotide encoding the polypeptide-of-choice (e.g., the IL6RIL6 chimera) is expressed]. Preferably, to generate an IL6RIL6 chimera with the amount and pattern of glycosylation as of the naturally occurring IL6 and IL6-R, the host cell employed is a eukaryotic host cell, more preferably a mammalian host cell such as human cell or CHO cell).

For expression in mammalian cells [e.g., CHO cells, human HEK 293 cells (ATCC CRL 1573)] a number of mammalian expression vectors can be used. Examples include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Various methods can be used to introduce the expression vector of the present invention into host cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Transformed cells are cultured under effective conditions, which allow for the expression of high amounts of the recombinant polypeptide (e.g., the IL6RIL6 chimera). Following a predetermined time in culture, recovery of the recombinant polypeptide is effected. The phrase "recovery of the recombinant polypeptide" used herein refers to collecting the whole fermentation medium containing the polypeptide and need not imply additional steps of separation or purification.

Thus, polypeptides of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

The polypeptide of the present invention (e.g., the IL6RIL6 chimera) is preferably retrieved in "substantially pure" form. As used herein, the phrase "substantially pure" refers to a purity that allows for the effective use of the polypeptide of the present invention (e.g., the IL6RIL6 chimera) in maintaining the human embryonic stem cells in an undifferentiated state while in culture.

Although currently less preferred, other culture media which comprise the IL6RIL6 chimera but also include serum or serum Replacement™ (e.g., the CM100F medium or similar media with other concentrations of the IL6RIL6 chimera such as 200 or 300 ng/ml as described in the Examples section which follows) can be used by the method of this aspect of the present invention. In this case the serum (e.g., human serum) or serum Replacement™ can be provided at various concentrations, such as a concentration of at least 10%, e.g., a concentration of at least 15%, at least 20%, at least 25% or at least 30%.

Serum Replacement™ includes albumin or albumin substitutes, amino acids, vitamins, transferrins or transferrin substitutes, antioxidants, insulin or insulin substitutes, collagen precursors and trace elements (International Patent Publication No. WO 98/30679 to Price, P. J. et al). To provide animal-free culture conditions the albumin or albumin substitutes are preferably derived from a human source and/or are prepared using recombinant techniques in host cells as described hereinabove.

When cultured according to the method of this aspect of the present invention, embryonic stem cell growth is monitored to determine their differentiation state. The differentiation state can be determined using various approaches including, for example, morphological evaluation (e.g., as shown in FIGS. 5a-g) and/or detection of the expression pattern of typical markers of the undifferentiated state using immunological techniques such as flow cytometry for membrane-bound markers, immunohistochemistry or immunofluorescence for extracellular and intracellular markers and enzymatic immunoassay, for secreted molecular markers. For example, immunofluorescence employed on hESCs cultured according to the method of this aspect of the present invention revealed the expression of Oct4, stage-specific embryonic antigen (SSEA) 4, the tumour-rejecting antigen (TRA)-1-60 and TRA-1-81 (FIGS. 4a-c and data not shown). Additionally, the level of transcripts of specific undifferentiation markers (e.g., Oct 4, Nanog, Sox2 and Rex1 as shown in FIGS. 6a-d) or differentiation markers (e.g., albumin, glucagons, α-cardiac actin, β-globulin, Flk1, AC133 and neurofilament) can be detected using RNA-based techniques such as RT-PCR analysis and/or cDNA microarray analysis.

Determination of ES cell differentiation can be also effected via measurements of alkaline phosphatase activity. Undifferentiated human ES cells have alkaline phosphatase activity which can be detected by fixing the cells with 4% paraformaldehyde and developing with the Vector Red substrate kit according to manufacturer's instructions (Vector Laboratories, Burlingame, California, USA).

Preferably, the embryonic stem cells cultured in any of the suspension culture media described hereinabove exhibit normal chromosomal karyotype following at least 1 passage, preferably, following at least 2 passages, preferably, following at least 3 passages, preferably, following at least 4 passages, preferably, following at least 5 passages, preferably, following at least 7 passages, preferably, following at least 10 passages, preferably, following at least 12 passages, preferably, following at least 15 passages, preferably, following at least 20 passages, preferably, following at least 25 passages, preferably, following at least 30 passages (e.g., hESCs exhibited normal karyotype following at least 14, 18, 23 or 36 passages), thus representing genetically stable human ESC lines.

Preferably, the embryonic stem cells cultured in any of the suspension culture media described hereinabove exhibit a doubling time of at least 20 hours, more preferably, a doubling time which is between 20 to 40 hours (e.g., about 36 hours), thus representing a non-tumorigenic, genetically stable human ESCs.

It should be noted that the present invention provides, for the first time, a cell culture which comprises embryonic stem cells and a culture media which comprises the soluble interleukin-6 receptor (sIL6R) and interleukin-6 (IL6) (separately) wherein the soluble IL6R is present at a concentration of at least 10 (ng/ml) (e.g., 25 ng/ml), and whereas the culture medium being capable of maintaining the embryonic stem cells in an undifferentiated state for at least 5 passages (see Example 4 of the Examples section which follows, which demonstrates undifferentiated hESCs following 19 passages).

Similarly, the present invention provides, for the first time, a cell culture which comprises human embryonic stem cells and a culture media which comprises LIF (at a concentration of at least 1000 u/ml), wherein the culture medium being capable of maintaining the human ESCs in an undifferentiated state for at least 18 passages (see Example 4 of the Examples section which follows).

It will be appreciated, that the newly defined suspension culture described hereinabove can be also used to derive new hESC lines in a complete, xeno-free, scalable culture system.

Thus, according to another aspect of the present invention there is provided a method of deriving an embryonic stem cell line. The method is effected by (a) obtaining an embryonic stem cell from a pre-implantation stage blastocyst, post-implantation stage blastocyst and/or a genital tissue of a fetus; and (b) culturing the embryonic stem cell in a suspension culture, under culturing conditions which allow expansion of the embryonic stem cells in an undifferentiated state, thereby deriving the embryonic stem cell line.

The term "deriving" as used herein refers to generating an embryonic stem cell line from at least one embryonic stem cell.

As used herein the phrase "embryonic stem cell line" refers to embryonic stem cells which are derived from a single or a group of embryonic stem cells of a single organism (e.g., a single human blastocyst), and which are characterized by the ability to proliferate in culture while maintaining the undifferentiated state and the pluripotent capacity.

Obtaining an embryonic stem cell from a pre-implantation stage blastocyst, post-implantation stage blastocyst and/or a genital tissue of a fetus can be performed using methods known in the art, as described hereinabove and in the "General Materials and Experimental Methods" of the Examples section which follows. Briefly, the zona pellucida is removed from a 5-7 day-old blastocyst using Tyrode's acidic solution (Sigma, St Louis MO, USA), the trophoblast layer is specifically removed either by immunosurgery or mechanically using 27 g needles and the exposed ICM is either directly cultured in a suspension culture with a suitable culture medium (e.g., the CM100F, HA16 or D2 medium) for 4-10 days (in case a preimplantation blastocyst is used) or subject to in vitro implantation by culturing the ICM for 6-8 days (to obtain cells of a 13 day-old blastocyst in case a post-implantation/pre-gastrulation blastocyst is used) on feeder layers or a feeder-free culturing system which allow implantation of the blastocyst to the surface, following which the implanted cells are isolated and further cultured in suspension as described hereinunder. When using the genital tissue of a fetus, the genital ridges are dissociated and cut into small chunks which are thereafter disaggregated into cells by mechanical dissociation. The single cell EG cells are then cultured in suspension culture with a suitable culture medium (e.g., the CM100F, HA16 or D2 medium) for 4-10 days.

Once obtained the ESCs are further cultured in suspension under conditions which allow expansion of the embryonic stem cells in the undifferentiated state, essentially as described hereinabove.

Preferably, the cell culture of the present invention is characterized by at least 40%, at least 50%, at least 60%, more preferably at least 70%, more preferably at least 80%, most preferably at least 85% of undifferentiated embryonic stem cells.

It will be appreciated that an established embryonic stem cell line can be subject to freeze/thaw cycles without hampering the proliferative capacity of the cells in the undifferentiated state while preserving their pluripotent capacity. For example, as is shown in the Examples section which follows, using 15% SR and 10% DMSO, hESCs were successfully frozen and thawed.

As described in Example 2 of the Examples section which follows, hESCs which were expanded and maintained in the suspension culture described hereinabove are pluripotent (i.e., capable of differentiating into all cell types of the three embryonic germ layers, the ectoderm, the endoderm and the mesoderm) as evidenced in vitro (by the formation of EBs). Thus, hESCs cultured according to the teachings of the present invention can be used as a source for generating differentiated, lineage-specific cells. Such cells can be obtained directly from the ESCs by subjecting the ESCs to various differentiation signals (e.g., cytokines, hormones, growth factors) or indirectly, via the formation of embryoid bodies and the subsequent differentiation of cells of the EBs to lineage-specific cells.

Thus, according to yet an additional aspect of the present invention there is provided a method of generating embryoid bodies from embryonic stem cells. The method is effected by (a) culturing the embryonic stem cells in a suspension culture under culturing conditions which allow expansion of the embryonic stem cells in an undifferentiated state to thereby obtain expanded, undifferentiated embryonic stem cells; and (b) subjecting the expanded, undifferentiated embryonic stem cells to culturing conditions suitable for differentiating the embryonic stem cells to embryoid bodies; thereby generating the embryoid bodies from the embryonic stem cells.

As used herein the phrase "embryoid bodies" refers to morphological structures comprised of a population of ESCs, extended blastocyst cells (EBCs) and/or embryonic germ cells (EGCs) which have undergone differentiation. EBs formation initiates following the removal of differentiation blocking factors from ES cell cultures. In the first step of EBs formation, ESCs proliferate into small masses of cells which then proceed with differentiation. In the first phase of differentiation, following 1-4 days in culture for human ESCs, a layer of endodermal cells is formed on the outer layer of the small mass, resulting in "simple EBs". In the second phase, following 3-20 days post-differentiation, "complex EBs" are formed. Complex EBs are characterized by extensive differentiation of ectodermal and mesodermal cells and derivative tissues.

Thus, the method of this aspect of the present invention involves the culturing of ESCs in a suspension culture using any of the culture media described hereinabove in order to obtain expanded, undifferentiated embryonic stem cells and then subjecting the expanded, undifferentiated ESCs to culturing conditions suitable for differentiating the ESCs to embryoid bodies. Such culturing conditions are substantially devoid of differentiation inhibitory factors which were employed during step (a), e.g., a TGFβ isoform or the IL6RIL6 chimera.

For EBs formation, the ESCs are transferred from the suspension cultures which include a culture medium capable of maintaining the ESCs in an undifferentiated state to a suspension culture in the presence of a culture medium containing serum or serum replacement and being devoid of differentiation-inhibitory factors, essentially as described in the "General Materials and Experimental Methods" of the Examples section which follows. For example, a culture medium suitable for EBs formation may include a basic culture medium (e.g., Ko-DMEM or DMEM/F12) supplemented with 20% FBSd (HyClone, Utah, USA), 1 mM L-glutamine, 0.1 mM β-mercaptoethanol, and 1% non-essential amino acid stock.

Monitoring the formation of EBs can be effected by morphological evaluations (e.g., histological staining as described in Example 2) and determination of expression of differentiation-specific markers [using e.g., immunological techniques or RNA-based analysis (e.g., RT-PCR, cDNA microarray)]. Non-limiting examples of differentiation-specific markers of all three embryonic germ layers include albumin and glucagon (typical of the embryonic endoderm), α-cardiac actin, β-globulin and Flk1 (typical of the embryonic mesoderm), and AC133 and neurofilament (NFH) (typical of the embryonic ectoderm).

It will be appreciated that in order to obtain lineage-specific cells from the EBs, cells of the EBs can be further subjected to culturing conditions suitable for lineage-specific cells.

Preferably, the method of this aspect of the present invention further includes step (c): subjecting cells of the embryoid bodies to culturing conditions suitable for differentiating and/or expanding lineage specific cells; thereby generating the lineage-specific cells from the embryonic stem cells.

As used herein the phrase "culturing conditions suitable for differentiating and/or expanding lineage specific cells" refers to a combination of a culture system, e.g., feeder cell layers, feeder-free matrix or a suspension culture and a culture medium which are suitable for the differentiation and/or expansion of specific cell lineages derived from cells of the EBs. Non-limiting examples of such culturing conditions are further described hereinunder.

Preferably, the method of this aspect of the present invention further includes isolating lineage specific cells following step (b).

As used herein, the phrase "isolating lineage specific cells" refers to the enrichment of a mixed population of cells in a culture with cells predominantly displaying at least one characteristic associated with a specific lineage phenotype. It will be appreciated that all cell lineages are derived from the three embryonic germ layers. Thus, for example, hepatocytes and pancreatic cells are derived from the embryonic endoderm, osseous, cartilaginous, elastic, fibrous connective tissues, myocytes, myocardial cells, bone marrow cells, vascular cells (namely endothelial and smooth muscle cells), and hematopoietic cells are differentiated from embryonic mesoderm and neural, retina and epidermal cells are derived from the embryonic ectoderm.

According to one preferred embodiment of the present invention, isolating is effected by sorting of cells of the EBs via fluorescence activated cell sorter (FACS).

Methods of isolating EB-derived-differentiated cells via FACS analysis are known in the art. According to one method, EBs are disaggregated using a solution of Trypsin and EDTA (0.025% and 0.01%, respectively), washed with 5% fetal bovine serum (FBS) in phosphate buffered saline (PBS) and incubated for 30 minutes on ice with fluorescently-labeled antibodies directed against cell surface antigens characteristics to a specific cell lineage. For example, endothelial cells are isolated by attaching an antibody directed against the platelet endothelial cell adhesion molecule-1 (PECAM1) such as the fluorescently-labeled PECAM1 antibodies (30884X) available from PharMingen (PharMingen, Becton Dickinson Bio Sciences, San Jose, CA, USA) as described in Levenberg, S. et al., (Endothelial cells derived from human embryonic stem cells. Proc. Natl. Acad. Sci. USA. 2002. 99: 4391-4396). Hematopoietic cells are isolated using fluorescently-labeled antibodies such as CD34-FITC, CD45-PE, CD31-PE, CD38-PE, CD90-FITC, CD117-PE, CD15-FITC, class I-FITC, all of which IgG1 are available from PharMingen, CD133/1-PE (IgG1) (available from Miltenyi Biotec, Auburn, CA), and glycophorin A-PE (IgG1), available from Immunotech (Miami, FL). Live cells (i.e., without fixation) are analyzed on a FACScan (Becton Dickinson Bio Sciences) by using propidium iodide to exclude dead cells with either the PC-LYSIS or the CELL-QUEST software. It will be appreciated that isolated cells can be further enriched using magnetically-labeled second antibodies and magnetic separation columns (MACS, Miltenyi) as described by Kaufman, D. S. et al., (Hematopoietic colony-forming cells derived from human embryonic stem cells. Proc. Natl. Acad. Sci. USA. 2001, 98: 10716-10721).

According to yet an additional preferred embodiment of the present invention, isolating is effected by a mechanical separation of cells, tissues and/or tissue-like structures contained within the EBs.

For example, beating cardiomyocytes can be isolated from EBs as disclosed in U.S. Pat. Appl. No. 20030022367 to Xu et al. Four-day-old EBs of the present invention are transferred to gelatin-coated plates or chamber slides and are allowed to attach and differentiate. Spontaneously contracting cells, which are observed from day 8 of differentiation, are mechanically separated and collected into a 15-mL tube containing low-calcium medium or PBS. Cells are dissociated using Collagenase B digestion for 60-120 minutes at 37° C., depending on the Collagenase activity. Dissociated cells are then resuspended in a differentiation KB medium (85 mM KCl, 30 mM $K_2HPO_4$, 5 mM $MgSO_4$, 1 mM EGTA, 5 mM creatine, 20 mM glucose, 2 mM $Na_2ATP$, 5 mM pyruvate, and 20 mM taurine, buffered to pH 7.2, Maltsev et al., Circ. Res. 75:233, 1994) and incubated at 37° C. for 15-30 minutes. Following dissociation cells are seeded into chamber slides and cultured in the differentiation medium to generate single cardiomyocytes capable of beating.

According to still additional preferred embodiments of the present invention, isolating is effected by subjecting the EBs to differentiation factors to thereby induce differentiation of the EBs into lineage specific differentiated cells.

Following is a non-limiting description of a number of procedures and approaches for inducing differentiation of EBs to lineage specific cells.

To differentiate the EBs of the present invention into neural precursors, four-day-old EBs are cultured for 5-12 days in tissue culture dishes including DMEM/F-12 medium with 5 mg/ml insulin, 50 mg/ml transferrin, 30 nM selenium chloride, and 5 mg/ml fibronectin (ITSFn medium, Okabe, S. et al., 1996, Mech. Dev. 59: 89-102). The resultant neural precursors can be further transplanted to generate neural cells in vivo (Brüstle, O. et al., 1997. In vitro-generated neural precursors participate in mammalian brain development. Proc. Natl. Acad. Sci. USA. 94: 14809-14814). It will be appreciated that prior to their transplantation, the neural precursors are trypsinized and triturated to single-cell suspensions in the presence of 0.1% DNase.

EBs of the present invention can differentiate to oligodendrocytes and myelinate cells by culturing the cells in modified SATO medium, i.e., DMEM with bovine serum albumin (BSA), pyruvate, progesterone, putrescine, thyroxine, triiodothryonine, insulin, transferrin, sodium selenite, amino acids, neurotrophin 3, ciliary neurotrophic factor and Hepes (Bottenstein, J. E. & Sato, G. H., 1979, Proc. Natl. Acad. Sci. USA 76, 514-517; Raff, M. C., Miller, R. H., & Noble, M., 1983, Nature 303: 390-396]. Briefly, EBs are dissociated using 0.25% Trypsin/EDTA (5 min at 37° C.) and triturated to single cell suspensions. Suspended cells are plated in flasks containing SATO medium supplemented with 5% equine serum and 5% fetal calf serum (FCS). Following 4 days in culture, the flasks are gently shaken to suspend loosely adhering cells (primarily oligodendrocytes), while astrocytes are remained adhering to the flasks and further producing conditioned medium. Primary oligodendrocytes are transferred to new flasks containing SATO medium for additional two days. Following a total of 6 days in culture, oligospheres are either partially dissociated and resuspended in SATO medium for cell transplantation, or completely dissociated and a plated in an oligosphere-conditioned medium which is derived from the previous shaking step [Liu, S. et al., (2000). Embryonic stem cells differentiate into oligodendrocytes and myelinate in culture and after spinal cord transplantation. Proc. Natl. Acad. Sci. USA. 97: 6126-6131].

For mast cell differentiation, two-week-old EBs of the present invention are transferred to tissue culture dishes including DMEM medium supplemented with 10% FCS, 2 mM L-glutamine, 100 units/ml penicillin, 100 mg/ml streptomycin, 20% (v/v) WEHI-3 cell-conditioned medium and 50 ng/ml recombinant rat stem cell factor (rrSCF, Tsai, M. et al., 2000. In vivo immunological function of mast cells derived from embryonic stem cells: An approach for the rapid analysis of even embryonic lethal mutations in adult mice in vivo. Proc Natl Acad Sci USA. 97: 9186-9190). Cultures are expanded weekly by transferring the cells to new flasks and replacing half of the culture medium.

To generate hemato-lymphoid cells from the EBs of the present invention, 2-3 days-old EBs are transferred to gas-permeable culture dishes in the presence of 7.5% $CO_2$ and 5% $O_2$ using an incubator with adjustable oxygen content. Following 15 days of differentiation, cells are harvested and dissociated by gentle digestion with Collagenase (0.1 unit/mg) and Dispase (0.8 unit/mg), both are available from F.Hoffman-La Roche Ltd, Basel, Switzerland. CD45-positive cells are isolated using anti-CD45 monoclonal antibody (mAb) M1/9.3.4.HL.2 and paramagnetic microbeads (Miltenyi) conjugated to goat anti-rat immunoglobulin as described in Potocnik, A. J. et al., (Immunology Hemato-lymphoid in vivo reconstitution potential of subpopulations derived from in vitro differentiated embryonic stem cells. Proc. Natl. Acad. Sci. USA. 1997, 94: 10295-10300). The isolated CD45-positive cells can be further enriched using a single passage over a MACS column (Miltenyi).

It will be appreciated that the culturing conditions suitable for the differentiation and expansion of the isolated lineage specific cells include various tissue culture media, growth factors, antibiotic, amino acids and the like and it is within the capability of one skilled in the art to determine which conditions should be applied in order to expand and differentiate particular cell types and/or cell lineages.

Additionally or alternatively, lineage specific cells can be obtained by directly inducing the expanded, undifferentiated ESCs to culturing conditions suitable for the differentiation of specific cell lineage.

In addition to the lineage-specific primary cultures, EBs of the present invention can be used to generate lineage-specific cell lines which are capable of unlimited expansion in culture.

Cell lines of the present invention can be produced by immortalizing the EB-derived cells by methods known in the art, including, for example, expressing a telomerase gene in the cells (Wei, W. et al., 2003. Mol Cell Biol. 23: 2859-2870) or co-culturing the cells with NIH 3T3 hph-HOX11 retroviral producer cells (Hawley, R. G. et al., 1994. Oncogene 9: 1-12).

It will be appreciated that since the lineage-specific cells or cell lines obtained according to the teachings of the present invention are developed by differentiation processes similar to those naturally occurring in the human embryo they can be further used for human cell-based therapy and tissue regeneration.

Thus, the present invention envisages the use of the expanded and/or differentiated lineage-specific cells or cell lines of the present invention for treating a disorder requiring cell replacement therapy.

For example, oligodendrocyte precursors can be used to treat myelin disorders (Repair of myelin disease: Strategies and progress in animal models. Molecular Medicine Today. 1997. pp. 554-561), chondrocytes or mesenchymal cells can be used in treatment of bone and cartilage defects (U.S. Pat. No. 4,642,120) and cells of the epithelial lineage can be used in skin regeneration of a wound or burn (U.S. Pat. No. 5,716,411).

For certain disorders, such as genetic disorders in which a specific gene product is missing [e.g., lack of the CFTR gene-product in cystic fibrosis patients (Davies J C, 2002. New therapeutic approaches for cystic fibrosis lung disease. J. R. Soc. Med. 95 Suppl 41:58-67)], ESC-derived cells are preferably manipulated to over-express the mutated gene prior to their administration to the individual. It will be appreciated that for other disorders, the ESC-derived cells should be manipulated to exclude certain genes.

Over-expression or exclusion of genes can be effected using knock-in and/or knock-out constructs [see for example, Fukushige, S. and Ikeda, J. E.: Trapping of mammalian promoters by Cre-lox site-specific recombination. DNA Res 3 (1996) 73-50; Bedell, M. A., Jerkins, N. A. and Copeland, N. G.: Mouse models of human disease. Part I: Techniques and resources for genetic analysis in mice. Genes and Development 11 (1997) 1-11; Bermingham, J. J., Scherer, S. S., O'Connell, S., Arroyo, E., Kalla, K. A., Powell, F. L. and Rosenfeld, M. G.: Tst-1/Oct-6/SCIP regulates a unique step in peripheral myelination and is required for normal respiration. Genes Dev 10 (1996) 1751-62].

In addition to cell replacement therapy, the lineage specific cells of the present invention can also be utilized to prepare a cDNA library. mRNA is prepared by standard techniques from the lineage specific cells and is further reverse transcribed to form cDNA. The cDNA preparation can be subtracted with nucleotides from embryonic fibroblasts and other cells of undesired specificity, to produce a subtracted cDNA library by techniques known in the art.

The lineage specific cells of the present invention can be used to screen for factors (such as small molecule drugs, peptides, polynucleotides, and the like) or conditions (such as culture conditions or manipulation) that affect the differentiation of lineage precursor to terminally differentiated cells. For example, growth affecting substances, toxins or potential differentiation factors can be tested by their addition to the culture medium.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., Ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (Eds.) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., Ed. (1994); "Culture of Animal Cells—A Manual of Basic Technique" by Freshney, Wiley-Liss, N.Y. (1994), Third Edition; "Current Protocols in Immunology" Volumes I-III Coligan J. E., Ed. (1994); Stites et al. (Eds.), "Basic and Clinical Immunology" (8th Edition), Appleton & Lange, Norwalk, CT (1994); Mishell and Shiigi (Eds.), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., Ed. (1984); "Nucleic Acid Hybridization" Hames, B. D., and Higgins S. J., Eds. (1985); "Transcription and Translation" Hames, B. D., and Higgins S. J., Eds. (1984); "Animal Cell Culture" Freshney, R. I., Ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

ESC culture—Human embryonic stem cell (hESC) lines 1-6, 14 and 1-3 [Amit&Itskovitz-Eldor, 2002] were cultured with inactivated mouse embryonic fibroblasts (MEFs) for 40-60 passages in a "basic hESC culture medium" consisting of 85% DMEM/F12 (Biological Industries, Biet Haemek, Israel) supplemented with 15% serum replacement (SR), 2 mM L-glutamine, 0.1 mM β-mercaptoethanol, 1% non-essential amino acid stock, and 4 ng/ml basic fibroblast growth factor (bFGF) (all but mentioned are from Gibco Invitrogen Corporation products, Grand Island NY, USA). This basic culture medium was used for the routine culture of hESCs in 2D culture with MEFs as control.

Tested media on the feeder layer, feeder-free or suspension cultures—The tested medium were as follows:

TGF β-Containing Media (i) D1 medium—Mab ADCB medium (HyClone, Utah, USA) supplemented with 2 mM L-glutamine (Invitrogen Corporation products, Grand Island NY, USA), 0.12 ng/ml TGFβ$_1$ (from R&D Systems Minneapolis MN, USA), and 10 ng/ml bFGF (Invitrogen Corporation products, Grand Island NY, USA).

(ii) D2 medium—Mab ADCB medium (HyClone, Utah, USA) supplemented with 2 mM L-glutamine (Invitrogen Corporation products, Grand Island NY, USA), 2 ng/ml TGFβ$_3$ and 10 ng/ml bFGF (Invitrogen Corporation products, Grand Island NY, USA).

(iii) HA16 medium—96% DMEM/F12 (Biological Industries, Biet Haemek, Israel) supplemented with 1:1000 dilution of the ITS Premix [the ITS premix is a X1000 stock solution obtained from BD Biosciences, Bedford, MA, USA and consists of 12.5 mg Insulin, 12.5 mg Transferrin and 12.5 mg Selenius acid], 2 mM L-glutamine, 2 ng/ml TGFβ$_3$ (from R&D Systems Minneapolis MN, USA), 4 ng/ml bFGF, 500 ng/ml ascorbic acid (Sigma, Steinheim, Germany), and a 1:1000 dilution of a lipid mixture (Sigma Cat. No. L5146, Steinheim, Germany) (all but those otherwise specified were obtained from Gibco Invitrogen Corporation products, Grand Island NY, USA).

(iv) HA19 medium—96% DMEM/F12 (Biological Industries, Beth Haemek, Israel) supplemented with 1:1000 dilution of the ITS premix (BD Biosciences, Bedford, MA, USA), 2 mM L-glutamine, 2 ng/ml TGFβ$_3$ (from R&D Systems Minneapolis MN, USA), 4 ng/ml bFGF, 500 ng/ml ascorbic acid (Sigma, Steinheim, Germany), a 1:1000 dilution of a lipid mixture (Sigma Cat. No. L5146, Steinheim, Germany) and a 1:100 dilution of Simfronic 68 (Pluronic F-68 solution, P5556 from Sigma, Steinheim, Germany, the stock is 10%, the F-68 in culture is provided at a concentration of 0.1%) (Sigma, Steinheim, Germany) (all but those otherwise specified were obtained from Gibco Invitrogen Corporation products, Grand Island NY, USA).

IL6RIL6 Chimera-Containing Media (i) CM100F medium—85% DMEM/F12 (Biological Industries, Biet Haemek, Israel) supplemented with 15% serum replacement (SR), 2 mM L-glutamine, 0.1 mM β-mercaptoethanol, 1% non-essential amino acid stock, 4 ng/ml basic fibroblast growth factor (bFGF) and 100 ng/ml IL6RIL6 chimera (a kind gift from Prof. Revel M, the Weizmann Inst. Rehovot, Israel; Chebath J, et al., 1997 and WO 99/02552 to Revel M., et al. SEQ ID NO:31) (all but those otherwise specified were obtained from Gibco Invitrogen Corporation products, Grand Island NY, USA). As a control, the same culture media was used with the removal of the growth factors (except for bFGF which remained in the control culture medium) and the IL6RIL6 chimera.

(ii) HACM100 medium—96% DMEM/F12 (Biological Industries, Biet Haemek, Israel) supplemented with a 1:1000 dilution of the ITS premix (BD Biosciences, Bedford, MA, USA), 2 mM L-glutamine, 4 ng/ml bFGF, 500 ng/ml ascorbic acid (Sigma, Steinheim, Germany), a 1:1000 dilution of a lipid mixture (Sigma Cat. No. L5146, Steinheim, Germany) and 100 ng/ml of IL6RIL6 chimera.

(iii) CM6 medium—85% Ko-DMEM (or 85% DMEM/F12, Biological Industries, Biet Haemek, Israel), supplemented with 15% serum replacement (SR), 2 mM L-glutamine, 0.1 mM β-mercaptoethanol, 1% non-essential amino acid stock, and 4 ng/ml bFGF, 0.3 ng/ml Interleukin-6 (IL6) and 0.5 ng/ml IL6 soluble receptor (both from R&D Systems Minneapolis MN, USA) (all Gibco Invitrogen Corporation products, Grand Island NY, USA).

(iv) "IL6-IL-6 receptor (IL6RIL6) chimera"—85% Ko-DMEM, supplemented with 15% serum replacement (SR), 2 mM L-glutamine, 0.1 mM β-mercaptoethanol, 1% non-essential amino acid stock, 4 ng/ml bFGF and 50 ng/ml, 100 ng/ml, 200 ng/ml or 300 ng/ml of IL6RIL6 chimera (Chebath J, et al., 1997 and WO 99/02552 to Revel M., et al. SEQ ID NO:31) (all Gibco Invitrogen Corporation products, Grand Island NY, USA). When used with 100 ng/ml of the IL6RIL6 chimera, this medium is also called CM100.

(v) Control medium—85% Ko-DMEM, supplemented with 15% serum replacement (SR), 2 mM L-glutamine, 0.1 mM β-mercaptoethanol, 1% non-essential amino acid stock, 4 ng/ml bFGF (all Gibco Invitrogen Corporation products, Grand Island NY, USA).

Feeder layers or feeder-free culturing systems—To test the ability of various culture media to support the growth of hESC in an undifferentiated yet pluripotent state the hESCs were transferred to several culture systems:

(i) Fibronectin feeder-free culture system—50 μg per 10 cm² fibronectin-covered plates (human plasma fibronectin, Chemicon International, Temecula CA, USA);

(ii) Matrigel™ feeder-free culture system—Matrigel™ (BD Biosciences, Bedfrod, MA, USA);

(iii) MEFs—mouse embryonic fibroblast feeder layer system;

(iv) Foreskins fibroblasts—foreskin fibroblasts feeder layer system.

Passaging of hESCs on feeder layers or feeder-free culturing systems—Cells were passaged every four to six days using 1.5 mg/ml type IV collagenase (Worthington biochemical corporation, Lakewood, NJ, USA). Cells were frozen in liquid nitrogen using a freezing solution consisting of 10% DMSO (Sigma, St Louis MO, USA), 40% human serum (HyClone, Utah, USA) and 50% DMEM/F12 (Biological Industries, Beit Haemek, Israel).

Culture in suspension—To examine the possibility of using the TGFβ-containing medium which is devoid of serum, serum replacement and albumin for scalable culture of hESCs in suspension, hESCs were cultured in suspension in 58 mm petri dishes (Greiner, Frickenhausen, Germany) in a cell density of $5\times10^4$-$2\times10^5$ cells/ml. The HA16 medium was supplemented with 0.1% F68 (Sigma, St. Louis, MO, USA) for the suspended culture. The culture medium in the suspension culture was changed on a daily basis. The basic media used for culturing hESCs in suspension (which can be further supplemented with the additive and growth factors as described hereinabove) were DMEM, ko-DMEM, DMEM/F12, MabADCB or NCTC medium.

"Passaging" of hESCs in suspension culture—The cells were passage every 5-7 days using either 30-60 minute incubation with 1.5 mg/ml type IV Collagenase (Worthington biochemical corporation, Lakewood, NJ, USA) or 25 minutes incubation with 1.5 mg/ml type IV Collagenase followed by five minutes incubation with 1 mg/ml Dispase (Invitrogen Corporation products, Grand Island NY, USA), and further broken into small clumps using 200 μl Gilson pipette tips. Alternatively, the cells were passaged mechanically using 27 g needles.

Following continuous culturing under these conditions the cells were tested for hESC characteristics.

RT PCR analysis—Total RNA was isolated from hESCs grown for 10-15 passages in the suspension culture using Tri-Reagent (Sigma, St. Louis MO, USA), according to the manufacturer's instructions. cDNA was synthesized from 1 μg total RNA using MMLV reverse transcriptase RNase H minus (Promega, Madison WI, USA). PCR reactions included denaturation for 5 minutes at 94° C. followed by repeated cycles of 94° C. for 30 seconds, annealing for 30 seconds at an annealing temperature as specified in Table 1, hereinbelow and extension at 72° C. for 30 seconds. PCR primers and reaction conditions used are described in Table 1, hereinbelow. PCR products were size-fractionated using 2% agarose gel electrophoresis. DNA markers were used to confirm the size of the resultant fragments.

TABLE 1

| RT-PCR conditions | | | |
|---|---|---|---|
| Gene product (Accession number) | Forward (F) and reverse (R) primers (SEQ ID NO:) | Reaction Condition | Size (bp) |
| Oct-4 (S81255) | F: 5'-GAGAACAATGAGAACCTTCAGGA (SEQ ID NO: 1)<br>R: 5'-TTCTGGCGCCGGTTACAGAACCA (SEQ ID NO: 2) | 30 cycles at 60° C. in 1.5 mM $MgCl_2$ | 219 |
| Albumin (AF542069) | F: 5'-TGCTTGAATGTGCTGATGACAGGG (SEQ ID NO: 3)<br>R: 5'- AAGGCAAGTCAGCAGCCATCTCAT (SEQ ID NO: 4) | 35 cycles at 60° C. in 1.5 mM $MgCl_2$ | 302 |
| α-fetoprotein (BC027881) | F: 5'-GCTGGATTGTCTGCAGGATGGGGAA (SEQ ID NO: 5)<br>R: 5'-TCCCCTGAAGAAAATTGGTTAAAAT (SEQ ID NO: 6) | 30 cycles at 60° C. in 1.5 mM $MgCl_2$ | 216 |
| NF-68KD (NFH (AY156690; X15307; X15309) | F: 5'-GAGTGAAATGGCACGATACCTA (SEQ ID NO: 7)<br>R: 5'-TTTCCTCTCCTTCTTCACCTTC (SEQ ID NO: 8) | 30 cycles at 60° C. in 2 mM $MgCl_2$ | 473 |
| α-cardiac actin (NM_005159) | F: 5'-GGAGTTATGGTGGGTATGGGTC (SEQ ID NO: 9)<br>R: 5'-AGTGGTGACAAAGGAGTAGCCA (SEQ ID NO: 10) | 35 cycles at 65° C. in 2 mM $MgCl_2$ | 486 |

TABLE 1-continued

RT-PCR conditions

| Gene product (Accession number) | Forward (F) and reverse (R) primers (SEQ ID NO:) | Reaction Condition | Size (bp) |
|---|---|---|---|
| β-Actin (NM_001101) | F: 5'-ATCTGGCACCACACCTTCTACAATGAGCTGCG (SEQ ID NO: 11)<br>R: 5'-CGTCATACTCCTGCTTGCTGATCCACATCTGC (SEQ ID NO: 12) | 35 cycles at 62° C. in 1.5 mM $MgCl_2$ | 838 |
| Sox2 (Z31560) | F: 5'CCCCCGGCGGCAATAGCA (SEQ ID NO: 13)<br>R: 3'TCGGCGCCGGGGAGATACAT (SEQ ID NO: 14) | 35 cycles at 60° C. in 1.5 mM $MgCl_2$ | 448 |
| Rex1 (AF450454) | F: 5'GCGTACGCAAATTAAAGTCCAGA (SEQ ID NO: 15)<br>R: 3' CAGCATCCTAAACAGCTCGCAGAAT (SEQ ID NO: 16) | 35 cycles at 56° C. in 1.5 mM $MgCl_2$ | 306 |
| CX43 (NM_000165) | F: 5'TACCATGCGACCAGTGGTGCGCT (SEQ ID NO: 17)<br>R: 3'GAATTCTGGTTATCATCGGGGAA (SEQ ID NO: 18) | 35 cycles at 61° C. in 1.5 mM $MgCl_2$ | 295 |
| FGF4 (NM_002007) | F: 5'CTACAACGCCTACGAGTCCTACA (SEQ ID NO: 19)<br>R: 3' GTTGCACCAGAAAAGTCAGAGTTG (SEQ ID NO: 20) | 35 cycles at 52° C. in 1.5 mM $MgCl_2$ | 370 |
| Glucagon (X03991) | F: 5' CTCAGTGATCCTGATCAGATGAACG (SEQ ID NO: 21)<br>R: 3' AGTCCCTGGCGGCAAGATTATCAAG (SEQ ID NO: 22) | 35 cycles at 65° C. in 1.5 mM $MgCl_2$ | 370 |
| β-globulin (V00499) | F: 5' ACCTGACTCCTGAGGAGAAGTCTGC (SEQ ID NO: 23)<br>R: 3' TAGCCACACCAGCCACCACTTTCTG (SEQ ID NO: 24) | 35 cycles at 65° C. in 1.5 mM $MgCl_2$ | 410 |
| Flk1 (NM_002253) | F: 5' ATGCACGGCATCTGGGAATC (SEQ ID NO: 25)<br>R: 3' GCTACTGTCCTGCAAGTTGCTGTC (SEQ ID NO: 26) | 35 cycles at 65° C. in 1.5 mM $MgCl_2$ | 437 |
| AC133 (NM_006017) | F: 5' CAGTCTGACCAGCGTGAAAA (SEQ ID NO: 27)<br>R: 3' GGCCATCCAAATCTGTCCTA (SEQ ID NO: 28) | 35 cycles at 65° C. in 1.5 mM $MgCl_2$ | 200 |
| Nanog (NG_004095) | F: 5' ACTAACATGAGTGTGGATCC (SEQ ID NO: 29)<br>R: 3' TCATCTTCACACGTCTTCAG (SEQ ID NO: 30) | 35 cycles at 61° C. in 1.5 mM $MgCl_2$ | 800 |

Table 1: RT-PCR primers and PCR conditions are provided along with the GenBank Accession numbers of the amplified transcripts.

Immunohistochemistry—Undifferentiated hESCs grown in the tested culture system were fixed with 4% paraformaldehyde and exposed to the primary antibodies (1:50) overnight at 4° C. Stage-specific embryonic antigen (SSEA) 1, 3 and 4 (Hybridoma Bank, IA, USA), tumor recognition antigen (TRA) 1-60 and TRA1-81 (Chemicon International, Temecula CA, USA) and Oct 4 (Santa Cruz Biotechnology, Santa Cruz, CA, USA) were used as primary antibodies. Cys 3 conjugated antibodies (Chemicon International, Temecula CA, USA) were used as secondary antibodies (1:200 dilution).

Karyotype analysis—Karyotype analysis (G-banding) was performed on at least 20 cells from each sample, two samples per test, as previously described [Amit et al, 2003]. Karyotypes were analyzed and reported according to the "International System for Human Cytogenetic Nomenclature" (ISCN).

EB formation from hESCs cultured in suspension—For the formation of EBs, one to three 58 mm petri dishes (Greiner, Frickenhausen, Germany) containing ESCs in suspension cultures were transferred to new 58 mm petri dishes containing EBs-differentiation medium consisting of 80% DMEM/F12 (Biological Industries, Beit Haemek, Israel), supplemented with 20% FBSd (HyClone, Utah, USA), and 1 mM L-glutamine (Invitrogen Corporation, Grand Island NY, USA). Alternatively, prior to their transfer to the EB-differentiation medium, the ESCs were subject to treatment with 1 mg/ml type IV collagenase and further broken into small clumps using 1000 μl Gilson pipette tips. 10 day-old EBs were harvested for RNA isolation and histological examination.

EB formation from hESCs cultured on 2-D (feeder free or feeder layers)—For the formation of EBs, one three confluent wells were used in a six-well plate (30 cm²). ESCs were removed from their culture dish using 1 mg/ml type IV collagenase, further broken into small clumps using 1000 µl Gilson pipette tips, and cultured in suspension in 58 mm petri dishes (Greiner, Frickenhausen, Germany). EBs were grown in differentiation medium consisting of 80% DMEM/F12 (Biological Industries, Beit Haemek, Israel), supplemented with 20% FBSd (HyClone, Utah, USA), and 1 mM L-glutamine (Invitrogen Corporation, Grand Island NY, USA).

Teratoma formation—For teratoma formation, cells cultured in the offered culture methods for more than 15 passages, were injected into the rear leg muscle of 4-week-old male SCID-beige mice (two mice for each tested culture system). Cell numbers ranged from $5 \times 10^6$ cells to $10^7$ cells per injection. Three to eight to 12 weeks after injection the mice were sacrificed and the resulting teratomas examined histologically.

Derivation of New hESC Lines in a Suspension Culture with the TGF β-Containing Medium Devoid of Serum, Serum Replacement and Albumin Blastocyst cultivation—Zygotes were donated by couples undergoing pre-implantation genetic diagnosis (PGD) or in vitro fertilization (IVF) at Cornell Medical College, NY, who signed informed consent forms. The couples underwent the traditional IVF procedure after ovarian stimulation with gonadotropins and oocyte retrieval. Zygotes were cultured to the blastocyst stage according to IVF laboratory standard protocol: under oil using specialized C1/C2 media for insemination, growth and blastocyst development (Cornell).

Derivation of hESC lines in a suspension culture—Following the removal of the zona pellucida using Tyrode's acidic solution (Sigma, St Louis MO, USA), the trophoblast layer is specifically removed either by immunosurgery or mechanically using 27 g needles. The exposed ICM is further cultured in suspension culture with a suitable culture medium (e.g., the CM100F, HA16 or D2) for 4-10 days. Initially, the cells are mechanically split using 27 g needles.

Derivation of hESC lines on foreskin fibroblasts—After digestion of the zona pellucida by Tyrode's acidic solution (Sigma, St Louis MO, USA) or its mechanical removal, the exposed blastocysts were placed in whole on a mitotically inactivated foreskin fibroblasts feeder layer (line F21 which was cultured in an animal free medium since its derivation until used). For the derivation and initial passages, cells were grown in the D2 or HA16 culture medium. The cells were initially passaged mechanically every four to ten days.

Example 1

Culturing Human Embryonic Stem Cell on Feeder-Free Culture Systems with a Medium Containing TGF-Beta Isoforms and being Devoid of Serum, Serum Replacement and Albumin Experimental Results In this study the ability of few medium combinations, HA16, HA19, D1, D2, and CM100 to support undifferentiated and prolonged culture of hESCs in different culture conditions was examined. The basic medium, D1 or D2, is a commercial medium design for industrial and clinical proposes for the culture of hybridomas in suspension. The medium is free from animal, serum products and proteins. HA16 and HA19 are based on defined materials only. The CM100 medium contains the IL6RIL6 chimera and serum replacement.

The effect of two isoforms of TGFβ, $TGFβ_1$ and $TGFβ_3$, in supporting hESCs undifferentiated culture, was examined. Initially, two measures were used to estimate the ability of hESCs to grow in several culture systems, namely percentage of differentiation and rate of growth. The culture system used were: (1) feeder layer-free method based on fibronectin or Matrigel™ which are the most used matrices; (2) MEF, and (3) foreskin fibroblast. Based on these two parameters, the media supplemented with $TGFβ_3$, D2, HA16 and HA19, were found to be the most suitable to support undifferentiated hESC proliferation in all tested culture methods. Culture medium supplemented with 10 ng/ml bFGF only, failed to support hESC prolonged culture, in all the tested culture conditions. Although 60% of the hESCs remained at the undifferentiated stage in these conditions for a few passages, the proliferation rate was low and with each passage the number of surviving hESCs decreased and the percentage of background differentiation was increased.

D1 medium on a feeder layer-free system is capable of maintaining all hESCs features along with high proliferation rate—When cultured in the feeder layer-free systems in the presence of the D1 medium, which is supplemented with $TGFβ_1$, the hESCs maintained all hESCs features including high proliferation rates. When cultured on the tested feeder layers in the presence of the D1 medium, the hESCs demonstrated a relatively high background differentiation rate of 20% and low proliferation abilities as compared to hESCs cultured at the same feeder layers systems with the D2 HA19 or HA16 medium.

D1, D2 and HA16 media in feeder layer-free are capable of maintaining hESCs in a proliferative, undifferentiated state, with chromosomal stability and pluripotency—Human ESCs grown in the presence of the D1, D2 or HA16 medium in feeder-layer free conditions were cultured continuously for up to 53, 24 or 10 passages, respectively, while maintaining their ESC features, including undifferentiated proliferation, chromosomal stability (as test by karyotype analysis, not shown) and pluripotency. The background differentiation rates were found to be less than 10%, which is similar to the differentiation rates occurring when hESCs are cultured in the traditional culture system based on MEFs as the feeder layer and medium supplemented with serum replacement and 4 ng/ml bFGF [Amit et al, 2000]. Examples of undifferentiated colonies cultured with D1, D2 or HA16 medium in feeder-layer free conditions and with the D2 or HA16 medium with the tested feeder layers are illustrated in FIGS. 1a-d.

hESCs cultured on feeder layer-free systems in the presence of the D1 or the D2 medium are devoid of autofeeder—Interestingly, when the hESCs were cultured in either the D1 or D2 medium on the feeder layer-free system the cells did not differentiate at the periphery of the colonies and did not form an outgrowth of feeder-like cells (also called "autofeeder") (FIG. 1d), as described in other reports on feeder layer-free culture methods for hESCs (Xu et al, 2001). No morphological differences could be observed between colonies grown in the feeder layer-free culture system and those grown with feeder layers (FIGS. 1a-d). Correspondingly, morphological features remained unchanged on a single-cell level, rendering cells small and round, and exhibiting high nucleus-to-cytoplasm ratio, with a notable presence of one to three nucleoli and typical spacing between the cells (FIGS. 1a-d).

The D1, D2 or HA16 media are capable of maintaining hESCs with normal population doubling—Similar to cells grown on MEFs, cells cultured with D2 or HA16 medium in all tested culture methods, and the D1 medium in the feeder layer-free systems, were passaged routinely every four to six days, at the same ratio of ½ or ⅓, indicating a similar population doubling time as of hESCs grown on MEFs. The cells were passage at the same seeding efficiency of about 1 million cells per 10 cm$^2$, with the same viability rate of over 95%. Using 40% human serum and 10% DMSO, cells were successfully frozen and thawed.

Karyotype analysis revealed normal karyotype of hESCs grown with the D1, D2, CM100 or HA16 media—15 passages and more after transferring the cells into the tested environments, karyotype analysis was performed by Giemsa banding on two separate cultures, representing the four medium conditions, D1, D2, CM100 and HA16 at the different culture methods. At least 20 cells were tested from each sample, 40 cells from each medium combination. All examined cells were found to sustain normal karyotype of 46,XX for cell lines 13 and 14 and 46,XY for cell line 16 (data not shown). Overall, these results suggest that the cells' karyotype remains stable in the tested conditions, similarly to ESCs grown with MEFs using traditional methods (Amit et al, 2000).

hESCs cultured with the D1, D2 or HA16 express typical cell surface markers—Several surface markers typical of primate undifferentiated ES cells were examined using immunofluorescent staining (Thomson et al, 1995, 1996, 1998). hESCs cultured with the D1, D2 or HA16 medium for more than 20 passages, while using the tested culture conditions, were found to be strongly positive to surface markers TRA-1-60 (FIG. 2a), SSEA4 (FIG. 2b), TRA-1-81 (FIG. 2c) and Oct 4 (data not shown). As in other primate ES cells, staining with SSEA3 was weak and negative for SSEA1 (data not shown).

hESCs cultured with the D1, D2 or HA16 medium are pluripotent as tested by EBs formation in vitro—The developmental potential of the cells after prolonged culture in the tested culture methods was examined in vitro by the formation of embryoid bodies (EBs). After more than 15, 20 and 30 passages in medium D1, D2 and HA16, respectively, hESCs formed EBs similar to those created by hESCs grown on MEFs (not shown). Within these EBs, stem cells differentiated into cell types representative of the three embryonic germ layers as described for EBs formed from hESCs cultured on other culture systems (Itskovitz-Eldor et al, 2000).

EBs formed from the hESCs cultured on the D1, D2 or HA16 medium are capable of differentiating into the ectoderm, endoderm and mesoderm cell lineages—While undifferentiated cells cultured in the tested medium, feeder layers and matrices, expressed undifferentiated genetic markers such as Oct 4, Nanog, Sox2, Rex1, Cx43 and FGF4 (not shown) [Bhattacharya et al, 2004], cells harvested from 10 day-old EBs expressed genes such as albumin and glucagon (endoderm), α-cardiac actin, β-globulin and Flk1 (mesoderm), and AC133 and neurofilament (ectoderm) as demonstrated by RT-PCR analysis (data not shown).

hESCs cultured with the D1, D2 or HA16 medium are pluripotent as tested by teratomas formation in vivo—The cells pluripotency was also tested in vivo by teratomas formation. hESCs cultured for over 12 passages in the HA16, D1 or D2 medium, in the tested culture systems formed teratomas following their injection into SCID-Beige mice. Within these teratomas, hESCs differentiated to representative tissues of the three embryonic germ layers including; cartilage, muscle, bone and fat (mesoderm), stratified epithelium, melanin containing epithelium (ectoderm), and kidney like structure (endoderm and mesoderm), and epithelium of endoderm origin (data not shown). Teratomas formation rates of 90%, and the number of injected cells were identical to those demonstrated by cells cultured using traditional methods (Amit et al, 2000).

The HA16 and D2 media are suitable for derivation of hESC line on foreskin fibroblast feeder layers in a complete xeno-free system—The medium combinations of the present invention were also tested for the ability to support hESC line derivation. Using the HA16 or D2 medium on foreskin fibroblasts as a supportive layer, new hESC lines were successfully derived and maintained for at least 2 passages (in the presence of the D2 medium) or at least 18 passages (in the presence of the HA16 medium). The hESC line derived on foreskin in the presence of the HA16 culture medium demonstrated stem cells morphology at passage 18 (and the culture is still ongoing), normal XY karyotype and pluripotency as evidenced by the formation of EBs (FIGS. 3a-b and data not shown). The growth and success rates were similar to those obtained while using traditional culture methods. Since the used foreskin fibroblasts line, F21, were derived without any animal products, this new hESC lines were derived under complete xeno-free conditions. Thus, the new hESC lines exhibit typical hESC morphology and proliferation rates, normal karyotype and pluripotency as evidenced by the formation of EB s.

Altogether, these results demonstrate that hESCs cells subjected to prolonged culture in the tested culture systems demonstrated all hESCs features including; pluripotency, chromosomal stability, expression of specific genes and surface markers and indefinite proliferation as undifferentiated cells.

Example 2

The TGFβ-Containing or IL6RIL6-Containing Culture Medium are Capable of Supporting Culturing of hESCs in Cell Suspension Since the new TGFβ-containing culture medium which is described in Example 1, hereinabove, is designed for massive cell culture (low protein content), suitable for industrial and clinical proposes cell production, the ability of D1, D2, HA19 and HA16 media to support suspension culture of undifferentiated hESCs was examined. In addition, the ability of a medium containing the IL6RIL6 chimera, such as the CM100F or HACM100 medium (as described in the General Materials and Experimental Methods) to support a suspension culture of hESCs was also examined. It should be noted that while the CM100F medium contains serum replacement, the HACM100 medium is serum or serum replacement-free and thus presents a well-defined culture, xeno-free culture medium.

Experimental Results

The CM100F, HA16, D1, D2 and HA19 media are suitable for culturing hESCs in suspension—hESCs were cultured in suspension using the newly developed TGFβ-containing medium types which are devoid of serum, serum replacement and albumin. To date, the highest passage of hESCs grown in suspension in the tested medium types were 3 passages in the D1 medium, 7 passages in the D2 medium, 10 passages in the HA19 medium and 17 passages in the CM100F medium. All hESCs exhibited undifferentiated morphology at these passages and can be further cultured in these media and maintain hESCs features. Histological sections of the hESCs clumps formed in the suspension cultures illustrated homogeneous cell population, of round cells with large nucleus (FIGS. 5a-g). In addition, when the cells were plated back on MEFs, they created colonies with typical hESCs morphology (FIGS. 5b-e), and if returned to suspension cultures, they continued proliferation as undifferentiated cells (data not shown). When hESCs were cultured in a suspension culture in the presence of the serum or serum replacement-free, IL6RIL6-containing HACM100 medium, the cells were expanded and maintained in the undifferentiated state for at least 1-2 passages (data not shown).

hESCs cultured in suspension in the presence of the D1, D2, HA19 or CM100F media express markers of undifferentiated hESCs—Cells cultured in suspension in the presence of the D2 medium for 3 passages as small clumps of 200-1500 cells expressed stem cells markers such as Oct 4 (FIG. 4a), TRA-1-60 (FIG. 4b), TRA-1-81 (FIG. 4c) and SSEA4 (data not shown). Similar results were obtained with the CM100F, D1 or D2 medium at passage 5 (p-5) (data not shown). When cultured in suspension culture in the presence of the CM100F or the HA19 medium the cells expressed high levels of typical stem cells markers such as Oct 4 (FIG. 6a), Rex1 (FIG. 6b), Sox2 (FIG. 6c), Nanog (FIG. 6d) and FGF4 (data not shown) as demonstrated by RT-PCR analysis.

ESCs cultured in suspension are capable of forming EBs—When removed from the D1, D2 or HA16 medium and transferred to EBs medium (80% DMEM/F12 supplemented with 20% FBSd and 1 mM L-glutamine), the cells formed EBs containing representative tissues of three embryonic germ layers (as evidenced by histological analysis, data not shown).

Rhesus ESCs can be also cultured in the suspension cultures of the present invention—Similar results with Rhesus ESCs (monkey embryonic stem cells, line R366.4, University of Wisconsin, primate center, Thomson lab, Madison, WI), which are regarded as good candidate for transgenic model to human diseases, were obtained when the Rhesus ESCs were cultured in suspension in the HA16, D1 and D2 TGFβ-containing culture media (data not shown).

Thus the new TGFβ-containing medium, which is devoid of serum, serum replacement and albumin, or the IL6RIL6-containing medium are capable of supporting the undifferentiated culture of hESCs, while maintaining hESCs characteristics, and provide methods for massive culture of these cells for industrial and clinical purposes.

Analysis and Discussion hESCs, like mouse ES cells, are traditionally cultured with MEFs, which may expose them to animal pathogens. In this study, the present inventors have demonstrated, for the first time, a defined animal, serum and feeder layer-free culture system for hESCs, based on the use of commercial medium supplemented with either $TGF\beta_3$ or $TGF\beta_1$ and bFGF, and human fibronectin matrix as substitute. This medium is designed for massive cultivation of cells in GMP for industrial or clinical purposes. All medium types of the present invention (with $TGF\beta_3$ or $TGF\beta_1$) support hESCs culture. When using the culture medium with TGFβ isoform 3 the results are better; less background differentiation. All media types of the present invention support the culture with feeders as good as with the regular serum containing media. Cells retained the same proliferation rates and the same background differentiation percentages as hESCs cultured with MEFs using traditional culture methods. Furthermore, the medium can also be used for massive suspended culture of undifferentiated hESCs.

Two isoforms of TGFβ, $TGF\beta_3$ and $TGF\beta_1$, were tested for their ability to maintain hESCs in an undifferentiated state using various culture conditions. $TGF\beta_3$ (D2 and HA16 media) was found to be the most suitable medium supplement, supporting undifferentiated culture of hESCs while using all the tested culture possibilities. All hESCs, from three different cell lines, continued to proliferate while retaining normal hESC features throughout the prolonged culture. Medium supplemented with $TGF\beta_1$ (D1 medium) on the contrary, was demonstrated to support undifferentiated hESC culture only while using feeder layer free culture systems.

Cells cultured while using these media (D1, D2, and HA16) maintained all the characteristics of ESCs. After prolonged culture of more than 20 passages, the cells remained undifferentiated, as demonstrated by the colony and single cell morphology, and by the expression of markers typical of undifferentiated primate ESCs [Thomson et al, 1995, 1996, 1998; Reubinoff et al, 2000]. In addition, while cultured in these conditions, hESCs expressed specific markers for the undifferentiated stage such as Oct 4, Sox 2, Rex1 and Nanog, as demonstrated by RT-PCR.

Karyotype analysis carried out on representative cell samples demonstrated that the hESCs' karyotype remained stable in the proposed conditions. None of the examined cells exhibited any karyotype abnormalities.

The cells' pluripotency was examined in vitro. Cells cultured in the tested culture systems for more than 10 passages, formed EBs similar to those created when grown on MEFs [Itskovitz-Eldor et al, 2000]. RT-PCR analysis demonstrated that cells within these EBs differentiated into different cell types representative of the three germ layers. Furthermore, following their injection to SCID-Beige mice, hESCs cultured in the presence of the D1 and D2 media formed teratomas containing a multitude of tissues types. hESCs cultured in the presence of the HA16 medium also formed teratomas and their histological evaluation is in process. The teratoma formation rates were identical to those of cells cultured with MEFs. Thus the pluripotency of the cells culture continuously in the tested culture methods remained intact.

Additionally, and most importantly, the same measurements were used to characterize cells cultured with the D1, D2 and HA16 media in suspension. Cell culture under these conditions for more than 7 passages, exhibit undifferentiated markers and when transferred to differentiation promoting conditions, demonstrated pluripotency. Thus these media can enable massive culture of undifferentiated hESCs, and facilitate to development of control bioprocesses in industrial bioreactors.

These results demonstrate that hESCs can be maintained as undifferentiated cells in the proposed defined animal- and serum-free medium combination, without any feeder cells (D1, D2 and HA16) or alternatively, with commonly used acceptable feeder layers (D2 and HA16). Thus, these media can facilitate hESCs culture for research, industrial and clinical purposes. Moreover, this novel culture media was found to support suspended culture of undifferentiated hESCs, the first and primary step in developing a massive culture system for their growth and scale-up, a crucial step for any industrial and clinical uses.

The mechanism by which hESCs self-maintain is still unclear. Accumulating data suggest the involvement of TGFβ family members in hESCs renewal [Amit et al, 2004; Ludwig et al, 2006; James et al, 2005; Chen et al, 2006, Valdimarsdottir & Mummery, 2006]. Further complementary research is required to explain the underlying mechanisms of action of TGFβ at the level of signal transduction, and the fact that $TGF\beta_3$ is more potent than $TGF\beta_1$.

Future clinical uses of hESCs will require a reproducible, well-defined and xeno-free culture system. The culture method described in this study which uses fibronectin as a feeder-free matrix and D1, D2 or HA16 medium and foreskins fibroblast meet these needs. The well-defined media demonstrated in the present study are suitable for culturing hESCs and may be advantageous for undertaking research on the mechanisms of ESC self-maintenance, especially of the possible roles of the TGFβ pathway. Other studies using hESCs, such as the research on differentiation pathways and mechanisms, will benefit from the availability of a well-defined and reproducible culture system.

Thus, the present invention discloses for the first time:

1. A culture system that allows hESC culturing in suspension as undifferentiated without carrier.
2. A scalable culture system, suitable for developing control bioprocesses in industrial bioreactors.
3. A xeno-free system suitable for both culture and derivation of hESCs. Derivation of new hESC lines directly in suspension.
4. Three defined medium combinations, highly effective in supporting hESCs culture in variety of culture conditions. Priority of TGFβ$_3$ over TGFβ$_1$. TGFβ$_3$ was never demonstrated to promote self-renewal of stem cells.

Example 3

Prolonged Culturing of Pluripotent, Undifferentiated Human ES Cells in Suspension in the Presence of the IL6RIL6 Chimera Materials and Experimental Methods
hESC Cultures hESC lines 1-3, 1-4 and 1-6 [Amit & Itskovitz-Eldor, 2002] were cultured with inactivated MEF for 54-89 passages as previously described [Amit et al, 2000]. The following culture medium combinations were tested for their ability to support the suspended culture of hESCs:

Basic culture medium—consisting of 85% DMEM/F12 (Biological Industries, Biet Haemek, Israel), containing 15% knockout serum replacement (SR), 2 mM L-glutamine, 0.1 mM β-mercaptoethanol, 1% non-essential amino acid stock, and 4 ng/ml bFGF (all but mentioned are Invitrogen Corporation products, Grand Island NY, USA). This basic culture medium was used for the routine culture of hESCs in 2D culture with MEFs as control.

CM100F medium—consisting of the basic culture medium supplemented with 100 ng/ml IL6RIL6 chimera [Chebath J, et al., 1997 and WO 99/02552 to Revel M., et al. SEQ ID NO:31].

CM6* medium—consisting of the basic culture medium with 100 ng/ml IL6 and 0.5 ng/ml IL6 soluble receptor (both from R&D Systems Minneapolis MN, USA).

CMLIF medium—consisting of the basic culture medium supplemented with 1000 units/ml human recombinant leukemia inhibitory factor (LIF) (R&D Systems Minneapolis MN, USA).

Culture in non-dynamic (static) suspension culture—The hESCs were removed from their culture dish using 1.5 mg/ml type IV collagenase (Worthington biochemical corporation, Lakewood, NJ, USA), further broken into small clumps using 200 μl Gilson pipette tips, and cultured in suspension in 58 mm Petri dishes (Greiner, Frickenhausen, Germany) in a cell density of 1×10$^6$-5×10$^6$ cells/plate. The medium in the suspension culture was changed daily, and the cells were passaged every 5-7 days either by manual cutting using 27 g needles or by gentle pippeting using 20 μl Gilson pipette tips.

Culture in Erlenmeyer (dynamic suspension culture)—Cells cultured in suspension for at least one passage were transferred to 125 ml Erlenmeyer (Corning Incorporated, Corning NY, USA) in 25 ml CM100F medium, and shaked continuously at 90 rpm using shaker (53.02.10L, ELMI ltd, Riga, Latvia). Medium was changed daily. Every 5-7 days the clumps were broken with gentle pippetation and split in a ratio of 1:2.

Immunohistochemistry—Undifferentiated hESCs grown in suspension or re-cultured on MEFs and differentiated cells dissociated using trypsin-EDTA from 10-day-old EBs were fixed with 4% paraformaldehyde and exposed to the primary antibodies overnight at 4° C. Cys 3 conjugated antibodies (Chemicon International, Temecula CA, USA) were used as secondary antibodies (1:200). The primary antibodies (1:50) include stage-specific embryonic antigen (SSEA) 1, 3 and 4 (Hybridoma Bank, IA, USA), tumor recognition antigen (TRA) 1-60 and TRA1-81 (Chemicon International, Temecula CA, USA), Oct4 (Santa Cruz Biotechnology, Santa Cruz, CA, USA), β-tubulin (Chemicon International, Temecula, CA, USA), troponin (Chemicon International, Temecula, CA, USA), PSA-NCAM (Chemicon International, Temecula, CA, USA).

Karyotype analysis—Karyotype analysis (G-banding) was performed on at least 10 cells from each sample, two samples per test, as previously described [Amit et al, 2003]. Karyotypes were analyzed and reported according to the "International System for Human Cytogenetic Nomenclature" (ISCN).

EB formation—For the formation of EBs, hESCs were passaged as described and transferred to 58 mm Petri dishes (Greiner, Frickenhausen, Germany). EBs were grown in medium consisting of 80% DMEM/F12 (Biological Industries, Biet Haemek, Israel), supplemented with 10% FBSd (HyClone, Utah, USA), 10% serum replacement (SR), 2 mM L-glutamine, 0.1 mM β-mercaptoethanol, and 1% non-essential amino acid stock (Invitrogen Corporation, Grand Island NY, USA). 10-14 day-old EBs were harvested for RNA isolation and histological examination. For staining they were plated on gelatin and cultured for 7-14 additional days. For histological analysis EBs were fixed in 10% neutral-buffered formalin, dehydrated in graduated alcohol (70%-100%) and embedded in paraffin. 1-5 μm sections were deparafined and stained with hematoxylin/eosin (H&E).

RT PCR—Total RNA was isolated from hESCs grown for 10, 15 and 20 passages in suspension and from 10-14 day-old EBs formed from cells grown in suspension or cells cultured on MEFs) using Tri-Reagent (Sigma, St. Louis MO, USA), according to the manufacturer's instructions. cDNA was synthesized from 1 μg total RNA using MMLV reverse transcriptase RNase H minus (Promega, Madison WI, USA). PCR reaction included denaturation for 5 minutes at 94° C. followed by repeated cycles of 94° C. for 30 seconds, annealing temperature (as shown in Table 1) for 30 seconds and extension at 72° C. for 30 seconds. PCR primers and reaction conditions were as described in Table 1 hereinabove, except that 30 cycles of amplifications were performed for the Nanog, Rex1, FGF4 and Sox2 PCR products. The PCR products were size-fractionated using 2% agarose gel electrophoresis. DNA markers were used to confirm the size of the resultant fragments.

Real time PCR—RNA was isolated from undifferentiated cells cultured on MEFs and from cells cultured in suspension for 10, 15 and 20 passages continuously. First-strand cDNA were synthesized as described above (RT-PCR). TaqMan Universal PCR Master Mix and Assay-on-Demand Agene Expression Probes (Applied Biosystems, Foster City, CA, USA) for Oct4 and I3-actin were used according to the manufacturer's guidelines. The reaction was performed with Applied Biosystems 7000 DNA Sequence Detection System (Applied Biosystems, Foster City, CA, USA) according to the manufacturer's instructions. The relative expression of Oct4 was normalized to the expression of β-actin for the same sample. The cDNA of cells cultured on MEFs were used as calibrators, and the relative expression of Oct4 was calculated accordingly by using the standard curve method described by the manufacturer. Three biological repeats were conducted for each sample.

Flow cytometry—The clumps of hESCs cultured in suspension were dissociated to single cells using triple-Express (Invitrogen Corporation products, Grand Island, NY, USA). The cells were stained with anti-h/mSSEA4 Ab conjugated to Phycoerythrin, Phycoerythrin conjugated Rat IgG2B were used as isotype control [both from R&D systems, Minneapolis, MN, USA]. The stained cells were then analyzed with FACScalibur flow cytometer (Becton Dickinson, San Jose, CA, USA) using CellQuest software according to the manufacturer's instructions.

Teratoma formation—Cells from four to six 58 mm dishes were harvested and injected into the hindlimb muscles of four week-old male of severe combined immunodeficiency (SCID)-beige mice. Ten weeks after the injection the resultant teratomas were harvested and prepared for histological analysis using the same method mentioned for EBs.

Western blot analysis—The cell pellets were lysed using RIPA buffer (Roche diagnostics, Penzberg, Germany) supplemented with phosphatase inhibitor cocktail (Sigma, St. Louis, MO, USA). Proteins were extracted from 13 ESCs cultured in suspension for 29 passages, from cells cultured on MEFs only, from cells that were cultured in suspension for 10 passages and then re-cultured on MEFs, and from cells of the trigger group experiment. Total protein was measured by Bradford Protein Assay (Bio-Rad laboratories, Hercules, CA, USA) according to the manufacturer's instructions. For Western blot analysis, the proteins were separated on 6-10% gradient sodium dodecyl sulfate (SDS)-polyacrylamide (SDS-page) mini gel electrophoresis (Sigma, St. Louis, MO, USA), and transferred to nitrocellulose membrane (Schleicher & Schuell, Dassel, Germany). After 1.5 hours blocking in 5% dry nonfat milk (Nestle carnation, Switzerland), the membrane was incubated with primary antibody for 2 hours at room temperature for β-actin (Sigma, St. Louis, MO, USA), and overnight at 4° C. for gp-130, p-STAT-3, and STAT-3 (All from Sigma, St. Louis, MO, USA). The membrane was washed thrice with Tween-TBS (T-TBS) for 10 minutes, then incubated for 1 hour with peroxidase-conjugated secondary antibody (Jackson Immuno research, Baltimore, PA, USA), followed by incubation for 3 minutes with chemiluminescent substrate HRP (Pierce, Rockford, IL, USA). Detection was performed using ECL western blotting analysis (Amersham Pharmacia Biotech, Piscataway, NJ, USA), and visualized by Image-Master VDS-CL (Amersham Pharmacia Biotech, Bucks, England).

Trigger experiments—Forty-eight hours post splitting, cells cultured in suspension were transferred into the culture medium (control; basic culture medium) without the addition of the IL6RIL6 chimera. 24 hours later, the chimera was added (at a concentration of 100 ng/ml) to the culture medium and cells were harvested immediately, after 30 minutes, after 3 hours and after 24 hours. Cells that were continuously cultured with the IL6RIL6 chimera were used as control.

Apoptosis analysis—Apoptosis levels were examined by In Situ Cell Death Detection Kit, AP (Roche Diagnostics GmbH, Mannheim, Germany) on the $2^{nd}$, $4^{th}$, $6^{th}$, $8^{th}$, $10^{th}$ and $14^{th}$ days of continuous growth without splitting. Apoptotic cells were detected by incubation for 3 minutes with Trypsin-EDTA (10×) (Invitrogen Corporation, Grand Island NY, USA) of 1 ml cells per pellet, treatment with 4 ml Hank's solution and fixation on the dry slide of the single cells before using the kit. Apoptotic cells were counted by inverted Zeiss Axiovert 200 fluorescent microscopy. At the same time, cell samples were harvested from the same culture, broken with trypsin using the same method, and stained with trypan-blue to evaluate the number of viable cells. Cells were counted by inverted Zeiss Axiovert 200 microscope.

Blocking of pg130 receptor experiments—Cells were cultured in suspension with CM100F medium. Increasing concentrations of anti-gp130 antibodies (Santa Crus Biotechnology, Santa Cruz, CA, USA) of 100 ng/ml, 250 ng/ml and 500 ng/ml, were added directly into the dishes on a daily basis. The number of differentiated clumps was counted 6 days later based on morphology using IX70 Olympus inverted microscope. Characteristics of differentiated clumps included cyst formation, and a ball like structures instead of disc like structures.

Experimental Results

The IL6RIL6 chimera, but not low concentrations of the IL6, soluble IL6 or LIF, are capable of maintaining hESCs in an undifferentiated state when cultured on fibronectin (2-D)—Three key cytokines of the IL6 family (LIF, IL6 and IL6RIL6 chimera) were tested for their ability to support the culture of undifferentiated hESCs in suspension. The ability of the various cytokines to maintain hESC self-renewal was first evaluated in the 2-D feeder layer-free culture system using fibronectin as a matrix. While the background differentiation of hESCs cultured in the presence of LIF or IL6 at the used concentrations (i.e., 1000 u/ml for LIF; 100 ng/ml for IL6 and 0.5 ng/ml for soluble IL6 receptor) was as high as 50%, it was only 22% on 2-D culture in the presence of the IL6RIL6 chimera (at concentration of 100 ng/ml IL6RIL6 chimera), mainly by creating "auto-feeders" as reported for other hESC feeder layer-free culture systems (data not shown, demonstrated by FACS analysis). Using 100 ng/ml of IL6RIL6 chimera and fibronectin as matrix it was possible to culture the hESCs continuously for over 40 passages, while maintaining stable karyotype, expression of undifferentiation markers and EB and teratoma formation. An example of the cells cultured on fibronectin in the presence of the CM100F medium is illustrated in FIG. 7a.

The IL6RIL6 chimera, but not low concentrations of the IL6 and soluble IL6, are capable of maintaining cultures of hESCs in suspension in an undifferentiated state—The cytokines' ability to support the culture of undifferentiated hESCs in suspension was then examined. With medium supplementation of 100 ng/ml IL6 and 0.5 ng/ml IL6 soluble receptor (medium CM6*) the cells formed either EBs or neurosphere-like structures within five to seven days of culture (data not shown). The neurosphere-like structures demonstrated round morphology when cultured in suspension, and several days after being plated on fibronectin neuron-like structures positively stained with either nestin or β-tubulin were observed (data not shown). With 100 ng/ml of IL6IL6 chimera (the CM100F medium), the cells created disc-like structures 24 hours after being cultured in suspension (FIG. 7c). Histological sections of these clumps revealed a homogenous population of small cells with large nuclei (FIG. 7d). The clumps were split every 5-7 days while maintaining their morphology for at least 54 passages (i.e., for at least a year of continuous culture). The three cell lines utilized for this experiment, I-3, I-4 and I-6 hESCs showed no morphological variability. When re-cultured on MEFs or fibronectin after 10 or 25 passages in suspension, 100% of the clumps adhered to the MEFs or the fibronectin and after 24-48 hours demonstrated typical hESC colony morphology, exhibiting high nucleus-to-cytoplasm ratio with a notable presence of one to three nucleoli and with typical spacing between the cells (FIGS. 7e and f). Differentiation background of the hESCs cultured in suspension in the presence of the CM100F medium consisted of up to 5% and included neurosphere-like structures as shown in FIG. 7b.

hESCs cultured in suspension in the presence of the IL6RIL6 chimera exhibit normal karyotype—Karyotype analyses by Giemsa banding was carried out on each cell line after 23, 18 and 36 passages in suspension, for 1-6, 1-3 and 1-4, respectively, and were found to be normal (data not shown). Similar results were obtained when the cells were re-cultured on MEFs; all samples but one of 1-3 (passage 12 on MEFs after 10 passages in suspension) demonstrated normal karyotype. The original culture of 1-3 that remained in suspension demonstrated normal karyotype. Thus the karyotype of the suspended cell culture remained stable.

hESCs cultured in suspension in the presence of the IL6RIL6 chimera exhibit expression pattern of undifferentiated state—Several surface markers typical of primate undifferentiated ESCs were examined using immunofluorescence staining [as described in Thomson et al, 1995, 1996, 1998]. Human ESCs cultured in suspension with CM100F medium for 42 and 43 passages were found to be strongly positive to surface markers SSEA4, TRA-1-60 and TRA-1-81 and Oct 4 (FIGS. 8a-d). As in other primate ESCs, staining with SSEA3 was weak and negative for SSEA1. Similar results were obtained for the cells cultured in suspension and returned to the MEFs. The former were further tested for typical undifferentiation markers using RT-PCR. Similarly to cells cultured with MEFs, cells cultured in suspension for 10, 15 and 20 passages expressed genetic markers of pluripotency Oct 4, Nanog, Sox2, Rex1, and FGF4 (FIG. 9) [Bhattacharya et al, 2004]. No difference was detected between cells cultured for various durations, nor between cells re-cultured on MEFs after continuous culture in suspension.

Flow cytometry analysis for SSEA4 revealed that 94.5% of 1-4 hESCs, at passage 30 in suspension (in the presence of the CM100F medium) and 94.7% of 1-6 hESCs at passage 20 in suspension (in the presence of the CM100F medium) were positive for SSEA4. For 1-3 hESCs, 87.8% of the cells at passage 34 in suspension (in the presence of the CM100F medium) were positive for SSEA4, demonstrating a slight increase in background differentiation (FIGS. 10a-c). When the background differentiation increased, differentiating clumps were removed using dissecting microscope based on their morphology, and a high expression level (>90%, e.g., >95%) of undifferentiation markers such as SSEA4, was restored (data not shown). Real time PCR analysis for the Oct4 gene expression level demonstrated no significant difference between cells cultured in suspension and those cultured on MEFs, and between different passages (10, 15, 20) of culture in suspension (FIGS. 11a-b).

hESCs cultured in suspension in the presence of the ILRIL6 chimera preserve their pluripotency as demonstrated by EBs' formation—The developmental potential of the cells after prolonged culture in suspension was examined in vitro by the formation of EBs. When cells cultured in suspension for over 20 passages were transferred to serum-containing medium where the Il6IL6 receptor chimera was removed, after a lag of 7-10 days, hESCs formed cystic EBs similar to those created by hESCs grown with MEFs (FIGS. 12a-b). Within these EBs, stem cells differentiated into cell types representative of the three embryonic germ layers [Itskovitz-Eldor et al, 2000]. Cells harvested from 21 day-old EBs expressed genes such as albumin (endoderm), α-cardiac actin, β-globulin and Flk1 (mesoderm), and AC133 and neurofilament (ectoderm) as demonstrated by RT-PCR (data not shown).

hESCs cultured in suspension in the presence of the ILRIL6 chimera preserve their pluripotency as demonstrated by teratoma formation—Cell pluripotency in vivo was demonstrated by teratoma formation. Cells cultured in the presence of the CM100F medium in suspension for 9, 10, 14 or 26 passages were injected into SCID Beige mice, representing the three tested cell lines, and after 10 weeks tumors formed in all four injected mice. Within these teratomas tissues representative of the three germ layers were observed (FIGS. 12a-b). Similar results were obtained when cells cultured for at least 10 passages in suspension were returned to the MEFs and cultured for additional 5-10 passages (data not shown).

Culture kinetics was tested by measuring the clumps' average size every second day during continuous culturing of 14 days. On day 7 the diameter increased from 150 μM to 300 μM, and on day 14 it was measured 500 μM (FIGS. 13a-d). Each of these clumps contained $2 \times 10^5$ live cells on day 2; $3.32 \times 10^5$ cells on the day of splitting (day 6); and $9 \times 10^5$ cells on day 14. Mechanical passaging resulted in an apoptosis level of 16% (FIG. 13e). During the next six days the average level of apoptosis dropped to 4.8% and increased again to 30% on day 14 of continuous culture (FIG. 13e). As expected, most of the apoptotic and necrotic cells were located at the center of the clump due to limited diffusion (FIGS. 13f-h). The cells' viability was found to be 90% until day 10, and 80% on day 14. The increase in the clumps' diameter and the low level of apoptosis indicate that days 5-7 are indeed the optimal time for splitting, as splitting of the cells at this time point prevents a great loss of cells for apoptosis and enables continuous cell proliferation.

Cells were cultured in suspension in the shaking Erlenmeyer for three months. An examination after one month showed that morphologically the clumps of disc-like, sphere structures remained similar to that of the cells cultured statically (FIG. 14a), although their size seemed more homogenous. The average sphere diameter in the dynamic system was 112±14.47 μM, each sphere containing $3.75 \times 10^4 \pm 3 \times 10^3$ cells. When re-cultured on MEFs the clumps re-attached, formed typical colonies of hESCs as occurred with cells that are cultured statically using Petri dishes (FIG. 14b), and were positively stained with undifferentiation markers (FIGS. 14c-e). Culturing of the spheres in Petri dishes with medium supplemented with serum without the Il6IL6 receptor chimera resulted in EB formation, and when the latter were re-plated on gelatin the cells were positively stained for troponin, PSA-NCAM, insulin and β-tubulin (FIGS. 14f-h). The karyotype of 13 hESCs cultured for one month in the Erlenmeyer was found to be normal. Finally, the cells' proliferation was tested to evaluate the suitability of this culture system for mass production of hESCs. The total sphere number increased from $1.33 \times 10^4 \pm 461$ on the seeding day to $3.5 \times 10^5 \pm 2.8 \times 10^4$ after 10-11 days in the dynamic culture, a 25-fold increase, and the total cell number increased from $5 \times 10^8$ to $1.31 \times 10^{10}$.

In order to gain insight into the possible contribution of the IL6RIL6 chimera to the self-maintenance mechanism of hESCs, trigger experiments were conducted. A clear increase in phosphorylated STAT3 levels could be noted three hours after re-adding the IL6RIL6 chimera, followed by an increase in gp130 receptor levels, as demonstrated by Western blot analysis (FIGS. 15a-d). The increase in phosphorylated STAT3 and gp-130 receptor levels could still be noted after 24 hours. Additional support for the IL6RIL6 chimera's involvement in the cells' self-maintenance was obtained from a competition experiment where anti-pg130 antibody was added to the culture medium with increasing concentrations. The level of background differentiation increased in parallel to the increased antibody concentration from 5% when no antibody was added, to 67% when 500 ng/ml antibody was added (FIG. 16). FIGS. 17a-b depict examples of differentiated (FIG. 17b) and undifferentiated (FIG. 17a) hESC clumps in the presence of the anti-gp 130 antibody.

Example 4

Testing Additional Media for Culturing Human Escs in Suspension

Materials and Experimental Methods
Culturing Media for Human ESCs in Suspension Cultures yFIL25+—85% DMEM/F12 (Biological Industries, Biet Haemek, Israel), containing 15% knockout serum replacement (SR), 2 mM L-glutamine, 0.1 mM β-mercaptoethanol, 1% non-essential amino acid stock, 4 ng/ml bFGF (all but mentioned are Invitrogen Corporation products, Grand Island NY, USA), 25 ng/ml IL6 and 25 ng/ml sIL6-R (R&D systems, Minneapolis, MN, USA).

yFL3—85% DMEM/F12 (Biological Industries, Biet Haemek, Israel), containing 15% knockout serum replacement (SR), 2 mM L-glutamine, 0.1 mM β-mercaptoethanol, 1% non-essential amino acid stock, 4 ng/ml bFGF (all but mentioned are Invitrogen Corporation products, Grand Island NY, USA), and 3000 u/ml human recombinant leukemia inhibitory factor (hrLIF) (R&D Systems Minneapolis Minn., USA).

yFL2—85% DMEM/F12 (Biological Industries, Biet Haemek, Israel), containing 15% knockout serum replacement (SR), 2 mM L-glutamine, 0.1 mM β-mercaptoethanol, 1% non-essential amino acid stock, 4 ng/ml bFGF (all but mentioned are Invitrogen Corporation products, Grand Island NY, USA), and 2000 u/ml hrLIF (R&D Systems Minneapolis MN, USA).

yFL1—85% DMEM/F12 (Biological Industries, Biet Haemek, Israel), containing 15% knockout serum replacement (SR), 2 mM L-glutamine, 0.1 mM β-mercaptoethanol, 1% non-essential amino acid stock, 4 ng/ml bFGF (all but mentioned are Invitrogen Corporation products, Grand Island NY, USA), and 1000 u/ml hrLIF (R&D Systems Minneapolis MN, USA).

TLF—85% DMEM/F12 (Biological Industries, Biet Haemek, Israel), containing 15% knockout serum replacement (SR), 2 mM L-glutamine, 0.1 mM β-mercaptoethanol, 1% non-essential amino acid stock, 4 ng/ml bFGF (all but mentioned are Invitrogen Corporation products, Grand Island NY, USA), 1000 u/ml hrLIF (R&D Systems Minneapolis MN, USA) and 0.12 ng/ml TGFβ$_1$ (R&D Systems Minneapolis MN, USA).

Experimental Results
New media combinations are suitable for culturing human ESCs in suspension culture—Four additional culture medium were tested for the ability to support suspension culture of hESCs; TLF, yFIL25+, yFL3 and yFL1. Using these culture media the human ESCs created spheres, or disc-like structures, 24 hours after being cultured in suspension using non-dynamic culture conditions (FIG. 18a-e). The clumps were split every 5-7 days while maintaining their morphology, and as of the day of writing this report reached 31, 19, 18 and 18 passages for TLF, yFIL25+, yFL3 and yFL1 respectively. Two lines of hESCs (13 and 14) were tested with each of the TLF, yFIL25+, yFL3 media, except for the yFL1 medium which was tested only with the 13 hESC line. When hESCs which were cultured for 10 passages in suspension with TLF or yFIL25+ media were re-cultured on MEFs or fibronectin, 100% of the clumps adhered to the MEFs or fibronectin and after 24-48 hours demonstrated typical hESC colony morphology, exhibiting high nucleus-to-cytoplasm ratio with a notable presence of one to three nucleoli and with typical spacing between the cells (FIG. 18c).

Human ESCs cultured in suspension in the presence of the TLF, yFIL25+, or yFL3 culture media exhibit normal karyotype—Karyotype analyses by Giemsa banding were carried out on each cell line after 18 passages in the TLF medium, 14 passages in the yFIL25+ medium and 14 passages in the yFL3 medium and were found to be normal.

Human ESCs cultured in suspension in the presence of the TLF, yFIL25+, yFL3 or yFL1 media exhibited undifferentiated state as evidenced by the expression of the surface markers SSEA4, TRA-1-60 and TRA-1-81 and Oct 4—Several surface markers typical of primate undifferentiated ESCs were examined using immunofluorescence staining according to the methods described elsewhere [Thomson et al, 1995, 1996, 1998]. Human ESCs cultured in suspension with TLF, yFIL25+, yFL3 and yFL1 medium for 31, 18, 18 and 18 passages, respectively, were found to be strongly positive to surface markers SSEA4, TRA-1-60 and TRA-1-81 and Oct 4 (FIGS. 19a-d).

Human ESCs cultured in suspension in the presence of the TLF, yFIL25+, yFL3 or yFL1 culture media express markers of pluripotency—Human ESCs cultured in suspension under non-dynamic culture conditions were further tested for typical undifferentiation markers using RT-PCR analysis. Similarly to cells cultured with MEFs, cells cultured in suspension for 18, 16, 16 or 18 passages in the presence of medium TLF, yFIL25+, yFL3 or yFL1, respectively, expressed genetic markers of pluripotency Oct 4, Nanog, Sox2, Rex1, and FGF4 (Data not shown).

Human ESCs cultured in suspension in the presence of the TLF, yFIL25+, yFL3 or yFL1 are capable of forming EBs which represent all three embryonic germ layers—The developmental potential of the cells after prolonged culture in suspension was examined in vitro by the formation of EBs. When cells cultured in suspension for over 10 passages were transferred to serum-containing medium where the growth factors were removed, after a lag of 7-10 days, hESCs formed cystic EBs (Data not shown). Within these EBs, stem cells differentiated into cell types representative of the three embryonic germ layers. Cells harvested from 21 day-old EBs expressed genes such as albumin (endoderm), α-cardiac actin, β-globulin and Flk1 (mesoderm), and AC133 and neurofilament (ectoderm) as demonstrated by RT-PCR (Data not shown).

Analysis and Discussion

Undifferentiated hESCs are traditionally cultured in 2D on either feeder-layer cells or on acellular matrix. This study demonstrates for the first time a method of culturing these cells as free floating spheres for prolonged periods in medium consisting of serum replacement, bFGF, and IL6RIL6 chimera.

Mouse ESCs can be cultured continuously without feeder layers provided that the culture medium is supplemented with leukemia inhibitory factor (LIF), which was found to be involved in the self-maintenance of mouse ESCs [Smith et al, 1988; Williams et al, 1988; Rose et al, 1994; Conover et al, 1993; Niwa et al, 1998]. Accumulating data regarding hESCs suggest that LIF has no effect on preventing hESC differentiation [Thomson et al, 1998; Reubinof et al, 2000]. Furthermore, activation of key proteins of the LIF cellular pathway, such as STAT3 was found to be weak or absent in hESCs [Daheron et al, 2004; Sato et al, 2004]. An additional candidate for hESC self-maintenance is the IL6RIL6 chimera. While LIF acts through the heteromeric complex of LIF-receptor and gp130, the IL6RIL6 chimera requires only gp130 to activate the intracellular pathway involving activation of JAK kinases and STAT transcription factors. In mouse cells, the IL6RIL6 chimera is known to be a potent inducer of the LIF/IL6 pathway, which results in a higher response compared with the effect caused by IL6 alone or even the chimera components added separately (IL6 and IL6 soluble receptors IL6R) (Chebath et al, 1997).

Furthermore, to date the only method for deriving new mouse ESC lines in feeder layer-free conditions is based on the addition of factors from the IL6 family [Nichols et al, 1994], or the combination of LIF and BMP4 when serum-free conditions are used [Ying Q L et al, 2003]. Of the IL6 family, the IL6RIL6 chimera was demonstrated as the most potent factor in supporting the feeder layer-free isolation of mouse ESC lines [Nichols et al, 1994]. The chimera has a much higher affinity for human gp130 than the mixture of IL6 and sIL6R [Kollet et al, 1999]. Nevertheless, a recent study demonstrated that although it activates the LIF/STAT pathway in hESCs, on its own the IL6RIL6 chimera is insufficient to maintain hESC pluripotency in adhesive two-dimensional (2D) feeder layer-free culture [Humphrey et al, 2004].

In the present study several cytokines of the IL-6 family (IL6RIL6 chimera, LIF and IL6) were tested for their ability to maintain hESCs in their undifferentiated state. Medium supplemented with 100 ng/ml of the IL6RIL6 chimera when used in conjunction with 4 ng/ml bFGF supported the culture of three hESC lines in suspension for over 40 passages and retained normal hESC features, including the expression of surface markers and genes typical of undifferentiated hESCs as detected by FACS, RT-PCR and immunostaining, normal karyotype and teratoma formation.

Similar results were obtained when the cells were transferred back onto the MEFs, including one group which was transferred to and from the MEFs and the suspension for four times and remained stable throughout.

The mechanism by which hESCs self-maintain is not entirely understood. In mouse ESCs the role of LIF and other members of the IL6 family, acting through gp130 and the JAK/STAT3 pathway, in maintaining prolonged culture of undifferentiated ESCs is well known [Smith et al, 1988; Williams et al, 1988; Rose et al, 1994; Conover et al, 1993; Niwa et al, 1998]. Previous studies did not demonstrate a significant effect of the IL6 family, including a fusion protein of portions of IL6 and the IL6 receptor, on the self-maintenance of undifferentiated hESCs [Daheron et al, 2004; Humphrey et al, 2004; Sato et al, 2004]. In this study the present inventors demonstrate that the IL6RIL6 chimera does support the culture of hESCs in suspension and to a lesser extent in adhesion culture with fibronectin serving as matrix. Trigger experiments demonstrate that IL6RIL6 chimera indeed increases the STAT3 phosphorylation levels in both suspension and 2D cultures (data not shown). Blocking the IL6RIL6 chimera effect by anti-gp130 antibody, increased the level of differentiation, further indicating that the IL6RIL6 chimera is involved in the self maintenance of the cells.

Further research is required to both elucidate the underlying mechanisms of action of the IL6RIL6 chimera at the level of signal transduction, its time course and intensity at which different pathways (JAK/STAT, PI-3 kinase, MAPK, see Hirano et al, 1997) are activated, and to understand why this pathway is less effective when undifferentiated cells are cultured in 2D.

The described culture system was also found to support hESCs proliferation. The size of each clump during passaging (5-7 days) was found to increase by 1.5 folds, and associated with low apoptosis levels and high viability rates. The number of cells in each sphere increased 1.66-fold during each passage (5-7 days). Taking together, the kinetic features of the newly developed culture system indicate that the system is as proficient as the 2D culture systems and could be used as a base for routine culture of undifferentiated hESCs.

An important requirement for clinical and industrial application of hESCs is a scalable culture system capable of generating masses of cells. The culture system presented here, can also be used as a base for the mass production of undifferentiated hESCs using dynamic systems such as spinner flasks and bioreactors.

Shifting undifferentiated hESCs from adhesion to suspension will facilitate the development of controlled scale-up processes. In addition, the methodology presented here requires Petri dishes and does not require enzymatic splitting, supportive cells nor conditioned media, making it a cost-effective system. Coupled with its simplicity, this approach is an attractive option for the routine culture of hESCs.

The present inventors' experience with the Erlenmeyer's dynamic system indicate that hESCs can be cultured continuously and maintain their typical features, while enabling a scale-up of 25 folds in 10 days. Although seeding concentrations and medium metabolites should still be optimized, the results presented here demonstrate that this system could serve as a basis for developing a controlled process for mass production of hESCs in bioreactors.

To date, only one publication reports a successful culture of mouse ESCs in a suspension system for one passage, which resulted in a 31 fold expansion in 5 days [Cormier J T., et al, 2006; Tissue Eng. 2006 Nov.; 12(11):3233-45]. The system was based on medium supplemented with calf serum and 1000 u/ml LIF. A more recent publication by the same group demonstrates that the same culture system could also be used for somewhat prolonged culture by splitting the cells with trypsin [Zur Nieden et al, 2007]. However, under these conditions, the mESCs exhibited a doubling time of 15 hours which may lead to chromosomal instability. Nevertheless, the authors did not show karyotype analysis of the cultured ESCs. As shown in several publications, mouse and human ESCs share only some of their features; they differ in the inability to culture hESCs in 2D using the traditional medium supplemented with calf serum and LIF without a feeder layer [Thomson et al, 1998]. The ability of the IL6RIL6 chimera to support the self-maintenance of hESCs in suspension illuminates once again the question of LIF-STAT3 pathway's possible role in hESC self-renewal.

Thus, this culture system presented herein is a further step forward toward creating the culture conditions that will make possible to fulfill the promise of hESCs.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES

Amit M, Carpenter M K, Inokuma M S, Chiu C-P, Harris C P, Waknitz M A, Itskovitz-Eldor J, Thomson J A. Clonally derived human embryonic stem cell lines maintain pluripotency and proliferative potential for prolonged periods of culture. Dev Biol 2000; 227:271-278.

Amit M. & Itskovitz-Eldor J. Derivation and spontaneous differentiation of human embryonic stem cells. J Anat. 2002; 200:225-232.

Amit M, Margulets V, Segev H, Shariki C, Laevsky I, Coleman R, and Itskovitz-Eldor J. Human feeder layers for human embryonic stem cells. Biol Reprod 2003; 68:2150-2156.

Amit M, Shariki K, Margulets V, and Itskovitz-Eldor J. "Feeder and serum-free culture system for human embryonic stem cells". Biol Reprod 70:837-845, 2004.

Bhattacharya B, Miura T, Brandenberg R, Mejido J, Luo Y, Yang A X, Joshi B H, Irene G, Thies R S, Amit M, Lyons I, Condie B G, Iskovitz-Eldor J, Rao M S, Puri R K. "Gene expression in human embryonic stem cell lines: unique molecular signature". Blood 15; 103(8):2956-64, 2004.

Cameron C M, Hu W S and Kaufman D S. (2006). Improved development of human embryonic stem cell-derived embryoid bodies by stirred vessel cultivation. Biotechnol Bioeng. 94(5): 938-948.

Chen S, Choo A, Chin A, Oh S K. TGF-beta2 allows pluripotent human embryonic stem cell proliferation on E6/E7 immortalized mouse embryonic fibroblasts. J Biotechnol. 2006, 122:341-361.

Chebath J, Fischer D, Kumar A, Oh J W, Kolett O, Lapidot T, Fischer M, Rose-John S, Nagler A, Slavin S, Revel M. Interleukin-6 receptor-interleukin-6 fusion proteins with enhanced interleukin-6 type pleiotropic activities. Eur Cytokine Netw. 1997; 8: 359-365.

Cheng, L., Hammond, H., Ye, Z., Zhan, X., Dravid, G. (2003). Human Adult Marrow Cells Support Prolonged Expansion of Human Embryonic Stem Cells in Culture. Stem Cells 21, 131-142.

Cormier J T, zur Nieden N I, Rancourt D E, Kallos M S. Expansion of undifferentiated murine embryonic stem cells as aggregates in suspension culture bioreactors. Tissue Eng. 2006 Nov.; 12(11):3233-45.

Conover J C, Ip N Y, Poueymirou W T, Bates B, Goldfarb M P, DeChiara™, Yancopoulos G D. Ciliary neurotrophic factor maintains the pluripotentiality of embryonic stem cells. Development. 1993 119(3):559-65.

Daheron L, Opitz S L, Zaehres H, Lensch W M, Andrews P W, Itskovitz-Eldor J, Daley G Q. LIF/STAT3 signaling fails to maintain self-renewal of human embryonic stem cells. Stem Cells. 2004; 22(5):770-8.

Gerecht-Nir S, Cohen S and Itskovitz-Eldor J. (2004) Bioreactor cultivation enhances the efficiency of human embryoid body (hEB) formation and differentiation. Biotechnol Bioeng. 86:493-502.

Hovatta O, Mikkola M, Gertow K, Stromberg A M, Inzunza J, Hreinsson J, Rozell B, Blennow E, Andang M, Ahrlund-Richter L. A culture system using human foreskin fibroblasts as feeder cells allows production of human embryonic stem cells. Hum Reprod. 2003 July; 18(7):1404-9.

Humphrey R K, Beattie G M, Lopez A D, Bucay N, King C C, Firpo M T, Rose-John S, Hayek A. Maintenance of pluripotency in human embryonic stem cells is STAT3 independent. Stem Cells. 2004; 22(4):522-30.

Itskovitz-Eldor J, Schuldiner M, Karsenti D, Eden A, Yanuka O, Amit M, Soreq H, Benvenisty N. Differentiation of human embryonic stem cells into embryoid bodies comprising the three embryonic germ layers. Mol Med 2000; 6:88-95.

James, D., Levine, A. J., Besser, D., Hemmati-Brivanlou, A. (2005). TGFbeta/activin/nodal signaling is necessary for the maintenance of pluripotency in human embryonic stem cells. Development. 132, 1273-1282.

Kollet O., Aviram R, Chebath J, ben-Hur H, Nagler A, Shultz L, Revel M and Lapidot T. The soluble Interleukin-6 (IL6) Receptor/IL6 fusion protein enhances in vitro maintenance and proliferation of human CD34+ CD38−/low cells capable of repopulating Severe Combined Immunodeficiency mice. BLOOD 1999; 94: 923-931.

Ludwig T E, Levenstein M E, Jones J M, Berggren W T, Mitchen E R, Frane J L, Crandall L J, Daigh C A, Conard K R, Piekarczyk M S, Llanas R A, Thomson J A. Derivation of human embryonic stem cells in defined conditions. Nat Biotechnol. 2006, 24, 185-187.

Nichols J, Chambers I, Smith A. Derivation of germline competent embryonic stem cells with a combination of interleukin-6 and soluble interleukin-6 receptor. Exp Cell Res. 1994 215(1):237-9.

Niwa H, Burdon T, Chambers I, Smith A. Self-renewal of pluripotent embryonic stem cells is mediated via activation of STAT3. Genes Dev. 1998 Jul. 1; 12(13):2048-60.

Ying Q L, Nichols J, Chambers I, Smith A. BMP induction of Id proteins suppresses differentiation and sustains embryonic stem cell self-renewal in collaboration with STAT3. 2003, Cell, 115(3):281-92.

Reubinoff B E, Pera M F, Fong C, Trounson A., Bongso A. Embryonic stem cell lines from human blastocysts: somatic differentiation in vitro. Nat Biotechnol 2000; 18:399-404.

Richards M, Fong C Y, Chan W K, Wong P C, Bongso A. Human feeders support prolonged undifferentiated growth of human inner cell masses and embryonic stem cells. Nat Biotechnol 2002; 20:933-936.

Rose T M, Weiford D M, Gunderson N L, Bruce A G. Oncostatin M (OSM) inhibits the differentiation of pluripotent embryonic stem cells in vitro. Cytokine. 1994 6(1):48-54.

Sato N, Meijer L, Skaltsounis L, Greengard P, Brivanlou A H. Maintenance of pluripotency in human and mouse embryonic stem cells through activation of Wnt signaling by a pharmacological GSK-3-specific inhibitor. Nat Med. 2004 Jan; 10(1):55-63.

Smith A G, Heath J K, Donaldson D D, Wong G G, Moreau J, Stahl M, Rogers D. Inhibition of pluripotential embryonic stem cell differentiation by purified polypeptides. Nature. 1988 336(6200):688-90.

Thomson J A, Kalishman J, Golos T G, Durning M, Harris C P, Becker R A, Hearn J P. Isolation of a primate embryonic stem cell line. Proc Natl Acad Sci USA 1995; 92:7844-7848.

Thomson J A, Kalishman J, Golos T G, Durning M, Harris C P, Hearn J P. Pluripotent cell lines derived from common marmoset (*Callithrix jacchus*) blastocysts. Biol Reprod 1996; 55: 254-259.

Thomson J A, Itskovitz-Eldor, J, Shapiro S S, Waknitz M A, Swiergiel J J, Marshall V S, Jones J M. Embryonic stem cell lines derived from human blastocysts. Science 1998; 282:1145-1147 [erratum in Science 1998; 282:1827].

Valdimarsdottir G, Mummery C. Functions of the TGFbeta superfamily in human embryonic stem cells. APMIS. 2005; 113:773-789.

Williams R, Hilton D, Pease S, Wilson T, Stewart C, Gearing D, Wagner E, Metcal, D, Nicola N, Gough N. Myeloid leukemia inhibitory factor maintains the developmental potential of embryonic stem cells. Nature 1988; 336:684-687.

Xu C, Inokuma M S, Denham J, Golds K, Kundu P, Gold J D, Carpenter M K. Feeder-free growth of undifferentiated human embryonic stem cells. Nat Biotechnol 2001, 19, 971-974.

Xu R H, Peck R M, Li D S, Feng X, Ludwig T, Thomson J A. Basic FGF and suppression of BMP signaling sustain undifferentiated proliferation of human E S cells. Nat Methods. 2005; 2(3):185-190.

Xu C, Rosler E, Jiang J, Lebkowski J S, Gold J D, O'Sullivan C, Delavan-Boorsma K, Mok M, Bronstein A, Carpenter M K. Basic fibroblast growth factor supports undifferentiated human embryonic stem cell growth without conditioned medium. Stem Cells. 2005, 23:315-23.

Zandstra P W, Bauwens C, Yin T, Liu Q, Schiller H, Zweigerdt R, Pasumarthi K B and Field L J. (2003) Scalable production of embryonic stem cell-derived cardiomyocytes. Tissue Eng. 9(4):767-78.

Zur Nieden N I, Cormier J T, Rancourt D E, Kallos M S. (2007). Embryonic stem cells remain highly pluripotent following long term expansion as aggregates in suspension bioreactors. J Biotechnol. 129(3):421-32.

What is claimed is:

1. A method of isolating lineage-specific cells from human pluripotent stem cells, comprising:
   (a) culturing the human pluripotent stem cells in a suspension culture without substrate adherence in the presence of a culture medium which allow expansion of the human pluripotent stem cells in the undifferentiated state for at least 5 passages, thereby obtaining expanded human pluripotent stem cells in an undifferentiated state,
   (b) differentiating said expanded human pluripotent stem cells in said undifferentiated state into embryoid bodies, and
   (c) isolating lineage specific cells from said embryoid bodies.

2. The method of claim 1, wherein said culturing without said substrate adherence is effected by culturing the human pluripotent stem cells in a culture vessel having an internal surface designed to prevent attachment or adherence of said pluripotent stem cells to said surface.

3. The method of claim 1, wherein said culturing is effected in the absence of components of extracellular matrix, a glass microcarrier or beads.

4. The method of claim 1, wherein said differentiating is effected by removing said culture medium from said expanded undifferentiated human pluripotent stem cells.

5. The method of claim 1, wherein said isolating is effected by sorting of cells of said embryoid bodies using a fluorescence activated cell sorter (FACS).

6. The method of claim 5, further comprising disaggregating said embryoid bodies prior to incubating cells of said embryoid bodies with a fluorescently-labeled antibody directed against a cell surface antigen characteristics to said lineage-specific cell.

7. The method of claim 1, wherein said lineage specific cells are differentiated from an embryonic endoderm of said embryoid bodies.

8. The method of claim 7, wherein said lineage-specific cells differentiated from said embryonic endoderm comprise hepatocytes and/or pancreatic cells.

9. The method of claim 1, wherein said lineage specific cells are differentiated from an embryonic mesoderm of said embryoid bodies.

10. The method of claim 9, wherein said lineage-specific cells differentiated from an embryonic mesoderm of said embryoid bodies comprise osseous cells, cartilaginous cells, elastic cells, fibrous connective tissue cells, myocytes, myocardial cells, bone marrow cells, vascular cells, and/or hematopoietic cells.

11. The method of claim 10, wherein said lineage-specific cells differentiated from an embryonic mesoderm of said embryoid bodies comprise cartilaginous cells, bone marrow cells, vascular cells, and/or hematopoietic cells.

12. The method of claim 1, wherein said lineage specific cells are differentiated from an embryonic ectoderm of said embryoid bodies.

13. The method of claim 12, wherein said lineage-specific cells differentiated from an embryonic ectoderm of said embryoid bodies comprise neural cells, retina cells and/or epidermal cells.

14. The method of claim 13, wherein said lineage-specific cells differentiated from an embryonic ectoderm of said embryoid bodies comprise neural cells and/or retina cells.

15. The method of claim 1, wherein said culturing is effected under xeno-free conditions.

16. The method of claim 1, wherein said pluripotent stem cells comprise embryonic stem cells.

17. The method of claim 1, wherein said pluripotent stem cells of step (a) remain in the undifferentiated state without adherence to said substrate for at least 5 passages.

18. The method of claim 1, wherein said pluripotent stem cells of step (a) express OCT4.

19. The method of claim 1, wherein said culture medium in step (a) is a serum-free culture medium selected from the group consisting of: a culture medium comprising a soluble interleukin-6 receptor (sIL6R) at a concentration of at least 10 nanogram per milliliter (ng/ml) and soluble interleukin-6 (IL6), a culture medium comprising at least 2000 units per milliliter (u/ml) leukemia inhibitor factor (LIF), a culture medium comprising an IL6RIL6 chimera and a culture medium which comprises a TGFb isoform.

* * * * *

```
                         SEQUENCE LISTING

<160> NUMBER OF SEQ ID NOS: 33

<210> SEQ ID NO 1
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 1
gagaacaatg agaaccttca gga                                                 23

<210> SEQ ID NO 2
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 2
ttctggcgcc ggttacagaa cca                                                 23

<210> SEQ ID NO 3
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 3
tgcttgaatg tgctgatgac aggg                                                24

<210> SEQ ID NO 4
<211> LENGTH: 24
<212> TYPE: DNA
<213> ORGANISM: Artificial sequence
```

```
<220> FEATURE:
<223> OTHER INFORMATION: Single strand DNA oligonucleotide

<400> SEQUENCE: 4
aaggcaagtc agcagccatc tcat                                              24

<210> SEQ ID NO 5
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 5
gctggattgt ctgcaggatg gggaa                                             25

<210> SEQ ID NO 6
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 6
tcccctgaag aaaattggtt aaaat                                             25

<210> SEQ ID NO 7
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 7
gagtgaaatg gcacgatacc ta                                                22

<210> SEQ ID NO 8
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 8
tttcctctcc ttcttcacct tc                                                22

<210> SEQ ID NO 9
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 9
ggagttatgg tgggtatggg tc                                                22

<210> SEQ ID NO 10
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 10
agtggtgaca aaggagtagc ca                                                22
```

<210> SEQ ID NO 11
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 11
atctggcacc acaccttcta caatgagctg cg                             32

<210> SEQ ID NO 12
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 12
cgtcatactc ctgcttgctg atccacatct gc                             32

<210> SEQ ID NO 13
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 13
cccccggcgg caatagca                                             18

<210> SEQ ID NO 14
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 14
tcggcgccgg ggagatacat                                           20

<210> SEQ ID NO 15
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 15
gcgtacgcaa attaaagtcc aga                                       23

<210> SEQ ID NO 16
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 16
cagcatccta aacagctcgc agaat                                     25

<210> SEQ ID NO 17
<211> LENGTH: 23
<212> TYPE: DNA
<213> ORGANISM: Artificial sequence
<220> FEATURE:
<223> OTHER INFORMATION: Single strand DNA oligonucleotide

```
<400> SEQUENCE: 17
taccatgcga ccagtggtgc gct                                          23

<210> SEQ ID NO 18
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 18
gaattctggt tatcatcggg gaa                                          23

<210> SEQ ID NO 19
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 19
ctacaacgcc tacgagtcct aca                                          23

<210> SEQ ID NO 20
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 20
gttgcaccag aaaagtcaga gttg                                         24

<210> SEQ ID NO 21
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 21
ctcagtgatc ctgatcagat gaacg                                        25

<210> SEQ ID NO 22
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 22
agtccctggc ggcaagatta tcaag                                        25

<210> SEQ ID NO 23
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 23
acctgactcc tgaggagaag tctgc                                        25

<210> SEQ ID NO 24
```

```
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 24
tagccacacc agccaccact ttctg                                           25

<210> SEQ ID NO 25
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 25
atgcacggca tctgggaatc                                                 20

<210> SEQ ID NO 26
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 26
gctactgtcc tgcaagttgc tgtc                                            24

<210> SEQ ID NO 27
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 27
cagtctgacc agcgtgaaaa                                                 20

<210> SEQ ID NO 28
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 28
ggccatccaa atctgtccta                                                 20

<210> SEQ ID NO 29
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 29
actaacatga gtgtggatcc                                                 20

<210> SEQ ID NO 30
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 30
```
tcatcttcac acgtcttcag    20

<210> SEQ ID NO 31
<211> LENGTH: 543
<212> TYPE: PRT
<213> ORGANISM: Artificial sequence
<220> FEATURE:
<223> OTHER INFORMATION: IL6R/IL6 chimeric protein

<400> SEQUENCE: 31

```
Met Leu Ala Val Gly Cys Ala Leu Leu Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
            340                 345                 350
```

-continued

```
Ser Leu Pro Val Glu Phe Met Pro Val Pro Gly Glu Asp Ser Lys
        355                 360                 365

Asp Val Ala Ala Pro His Arg Gln Pro Leu Thr Ser Ser Glu Arg Ile
370                 375                 380

Asp Lys Gln Ile Arg Tyr Ile Leu Asp Gly Ile Ser Ala Leu Arg Lys
385                 390                 395                 400

Glu Thr Cys Asn Lys Ser Asn Met Cys Glu Ser Ser Lys Glu Ala Leu
                405                 410                 415

Ala Glu Asn Asn Leu Asn Leu Pro Lys Met Ala Glu Lys Asp Gly Cys
            420                 425                 430

Phe Gln Ser Gly Phe Asn Glu Glu Thr Cys Leu Val Lys Ile Ile Thr
        435                 440                 445

Gly Leu Leu Glu Phe Glu Val Tyr Leu Glu Tyr Leu Gln Asn Arg Phe
    450                 455                 460

Glu Ser Ser Glu Glu Gln Ala Arg Ala Val Gln Met Ser Thr Lys Val
465                 470                 475                 480

Leu Ile Gln Phe Leu Gln Lys Lys Ala Lys Asn Leu Asp Ala Ile Thr
                485                 490                 495

Thr Pro Asp Pro Thr Thr Asn Ala Ser Leu Leu Thr Lys Leu Gln Ala
            500                 505                 510

Gln Asn Gln Trp Leu Gln Asp Met Thr Thr His Leu Ile Leu Arg Ser
        515                 520                 525

Phe Lys Glu Phe Leu Gln Ser Ser Leu Arg Ala Leu Arg Gln Met
    530                 535                 540

<210> SEQ ID NO 32
<211> LENGTH: 365
<212> TYPE: PRT
<213> ORGANISM: Homo sapiens

<400> SEQUENCE: 32

Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190
```

```
Cys Val Ala Ser Ser Val Gly Ser Lys Phe Ser Lys Thr Gln Thr Phe
        195                 200                 205

Gln Gly Cys Gly Ile Leu Gln Pro Asp Pro Ala Asn Ile Thr Val
210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
                260                 265                 270

Leu Gln His His Cys Val Ile His Asp Ala Trp Ser Gly Leu Arg His
                275                 280                 285

Val Val Gln Leu Arg Ala Gln Glu Glu Phe Gly Gln Gly Glu Trp Ser
290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
                340                 345                 350

Ser Leu Pro Gly Ser Arg Arg Gly Ser Cys Gly Leu
                355                 360                 365

<210> SEQ ID NO 33
<211> LENGTH: 244
<212> TYPE: PRT
<213> ORGANISM: Homo sapiens

<400> SEQUENCE: 33

Val Pro Pro Glu Glu Pro Gln Leu Ser Cys Phe Arg Lys Ser Pro Leu
1               5                   10                  15

Ser Asn Val Val Cys Glu Trp Gly Pro Arg Ser Thr Pro Ser Leu Thr
                20                  25                  30

Thr Lys Ala Val Leu Leu Val Arg Lys Phe Gln Asn Ser Pro Ala Glu
            35                  40                  45

Asp Phe Gln Glu Pro Cys Gln Tyr Ser Gln Glu Ser Gln Lys Phe Ser
        50                  55                  60

Cys Gln Leu Ala Val Pro Glu Gly Asp Ser Ser Phe Tyr Ile Val Ser
65                  70                  75                  80

Met Cys Val Ala Ser Ser Val Gly Ser Lys Phe Ser Lys Thr Gln Thr
                85                  90                  95

Phe Gln Gly Cys Gly Ile Leu Gln Pro Asp Pro Ala Asn Ile Thr
            100                 105                 110

Val Thr Ala Val Ala Arg Asn Pro Arg Trp Leu Ser Val Thr Trp Gln
        115                 120                 125

Asp Pro His Ser Trp Asn Ser Ser Phe Tyr Arg Leu Arg Phe Glu Leu
    130                 135                 140

Arg Tyr Arg Ala Glu Arg Ser Lys Thr Phe Thr Thr Trp Met Val Lys
145                 150                 155                 160

Asp Leu Gln His His Cys Val Ile His Asp Ala Trp Ser Gly Leu Arg
                165                 170                 175

His Val Val Gln Leu Arg Ala Gln Glu Glu Phe Gly Gln Gly Glu Trp
            180                 185                 190

Ser Glu Trp Ser Pro Glu Ala Met Gly Thr Pro Trp Thr Glu Ser Arg
```

-continued

```
            195                 200                 205
Ser Pro Pro Ala Glu Asn Glu Val Ser Thr Pro Met Gln Ala Leu Thr
    210                 215                 220

Thr Asn Lys Asp Asp Asp Asn Ile Leu Phe Arg Asp Ser Ala Asn Ala
225                 230                 235                 240

Thr Ser Leu Pro
```